US010316101B2

(12) United States Patent
Galetto

(10) Patent No.: US 10,316,101 B2
(45) Date of Patent: Jun. 11, 2019

(54) BCMA (CD269) SPECIFIC CHIMERIC ANTIGEN RECEPTORS FOR CANCER IMMUNOTHERAPY

(71) Applicant: CELLECTIS, Paris (FR)

(72) Inventor: Roman Galetto, Paris (FR)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 15/302,450

(22) PCT Filed: Apr. 13, 2015

(86) PCT No.: PCT/EP2015/057995
§ 371 (c)(1),
(2) Date: Oct. 6, 2016

(87) PCT Pub. No.: WO2015/158671
PCT Pub. Date: Oct. 22, 2015

(65) Prior Publication Data
US 2017/0183418 A1 Jun. 29, 2017

(30) Foreign Application Priority Data
Apr. 14, 2014 (DK) .................... 2014 70212

(51) Int. Cl.
| *A61K 35/17* | (2015.01) |
| *C07K 16/28* | (2006.01) |
| *C07K 14/725* | (2006.01) |
| *C07K 14/705* | (2006.01) |
| *C12N 5/0783* | (2010.01) |
| *A61K 35/12* | (2015.01) |
| *A61K 39/00* | (2006.01) |

(52) U.S. Cl.
CPC .......... *C07K 16/2878* (2013.01); *A61K 35/17* (2013.01); *C07K 14/7051* (2013.01); *C07K 14/70517* (2013.01); *C07K 14/70575* (2013.01); *C07K 14/70578* (2013.01); *C12N 5/0636* (2013.01); *A61K 2035/124* (2013.01); *A61K 2039/5156* (2013.01); *A61K 2039/585* (2013.01); *C07K 2317/24* (2013.01); *C07K 2317/53* (2013.01); *C07K 2317/565* (2013.01); *C07K 2317/622* (2013.01); *C07K 2317/70* (2013.01); *C07K 2317/73* (2013.01); *C07K 2319/02* (2013.01); *C07K 2319/03* (2013.01); *C07K 2319/33* (2013.01); *C07K 2319/74* (2013.01); *C12N 2501/599* (2013.01); *C12N 2510/00* (2013.01)

(58) Field of Classification Search
CPC ..................... C07K 16/2878; A61K 35/17
USPC ........................... 424/133.1, 93.21
See application file for complete search history.

(56) References Cited

U.S. PATENT DOCUMENTS

| 9,944,702 | B2 * | 4/2018 | Galetto | C07K 16/2803 |
| 2014/0134142 | A1 * | 5/2014 | Smith | A61K 35/17 |
| | | | | 424/93.21 |
| 2016/0046724 | A1 * | 2/2016 | Brogdon | A61K 35/12 |
| | | | | 424/134.1 |
| 2016/0184362 | A1 * | 6/2016 | Duchateau | A61K 35/17 |
| | | | | 435/456 |
| 2016/0237139 | A1 * | 8/2016 | Pule | A61K 35/17 |
| 2016/0297884 | A1 * | 10/2016 | Kuo | C07K 16/2878 |
| 2017/0073423 | A1 * | 3/2017 | Juillerat | C07K 16/30 |
| 2019/0002561 | A1 * | 1/2019 | Galetto | C07K 16/2803 |

FOREIGN PATENT DOCUMENTS

| CN | 105777911 | * | 7/2016 |
| WO | WO 2012/079000 A1 | | 6/2012 |
| WO | WO 2013/154760 A1 | | 10/2013 |

OTHER PUBLICATIONS

Boldajipour et al., ASH, 58th Annual Meeting & Exposition, "Preclinical Evaluation of Allogeneic Anti-Bcma Chimeric Antigen Receptor T Cells with Safety Switch Domains and Lymphodepletion Resistance for the Treatment of Multiple Myeloma" (Oral presentation, Sunday, Dec. 4, 2016: 12:30 PM).*
Poirot et al., Can. Res. Sep. 15, 2015;75(18):3853-64. doi: 10.1158/0008-5472.CAN-14-3321. Epub Jul. 16, 2015.*
Valton et al. Molecular Therapy vol. 23 No. 9, 1507-1518 Sep. 2015.*
Juillerat et al., Sci Rep. Jan. 11, 2016;6:18950. doi: 10.1038/srep18950.*
Juillerat et al., Sci Rep. Jan. 20, 2017;7:39833. doi: 10.1038/srep39833.*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*

(Continued)

*Primary Examiner* — Lynn A Bristol
(74) *Attorney, Agent, or Firm* — Casimir Jones, S.C.; Peter J. Schlueter

(57) ABSTRACT

The present invention relates to Chimeric Antigen Receptors (CAR) that are recombinant chimeric proteins able to redirect immune cell specificity and reactivity toward selected membrane antigens, and more particularly in which extracellular ligand binding is a scFV derived from a BCMA monoclonal antibody, conferring specific immunity against BCMA positive cells. The engineered immune cells endowed with such CARs are particularly suited for treating lymphomas, multiple myeloma and leukemia.

20 Claims, 6 Drawing Sheets
Specification includes a Sequence Listing.

(56) References Cited

OTHER PUBLICATIONS

Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410).*
Ormhoj et al., Curr Hematol Malig Rep. Feb. 23, 2017. doi: 10.1007/s11899-017-0373-2. [Epub ahead of print].*
Maus et al. Clin Cancer Res. Apr. 15, 2013; 19(8): 1917-1919. doi:10.1158/1078-0432.CCR-13/0168.*
Carpenter et al. Clin Cancer Res. Apr. 15, 2013; 19(8): 2048-2060. doi:10.1158/1078-0432.CCR-12.2422.*
Carpenter et al., "B-cell Maturation Antigen is a Promising Target for Adoptive T-cell Therapy of Multiple Myelorna," /Clin Cancer Res; vol. 19, Apr. 2013, pp. 2048-2060.
Finney et al., "Activation of Resting Human Primary T Cells with Chimeric Receptors: Costimulation from CD28, Inducible Costimulator, CD134, and CD137 in Series with Signals from the TCR Chain," The Journal of Immunology, 2004, pp. 104-113.
Garfall et al., "Immunotherapy with Chimeric Antigen Receptors for Multiple Myeloma," Discovery Medicine, vol. 17, Jan. 2014, pp. 37-46.
International Search Report issued in Danish Patent Application No. 201470212 dated Dec. 5, 2014.
Jensen et al., "Design and Implementation of Adoptive Therapy with Chimeric Antigen Receptor-modified T Cells," Immunological Reviews, vol. 257, 2014, pp. 137-144.
Porter et al., "Chimeric Antigen Receptor Therapy for B-cell Malignancies," Journal of Cancer, vol. 2, 2011, pp. 331-332.
Carpenter et al., "B-cell Maturation Antigen Is a Promising Target for Adoptive T-cell Therapy of Multiple Myeloma," Clinical Cancer Research, vol. 19(8), Apr. 2013, pp. 2048-2060.

* cited by examiner

SEQUENCE LISTING

```
<160> NUMBER OF SEQ ID NOS: 69

<210> SEQ ID NO 1
<211> LENGTH: 21
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: signal peptide

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 20
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: signal peptide

<400> SEQUENCE: 2

Met Glu Thr Asp Thr Leu Leu Leu Trp Val Leu Leu Leu Trp Val Pro
1               5                   10                  15

Gly Ser Thr Gly
            20

<210> SEQ ID NO 3
<211> LENGTH: 16
<212> TYPE: PRT
<213> ORGANISM: homo sapiens
<220> FEATURE:
<223> OTHER INFORMATION: FcgRIIIa hinge

<400> SEQUENCE: 3

Gly Leu Ala Val Ser Thr Ile Ser Ser Phe Phe Pro Pro Gly Tyr Gln
1               5                   10                  15

<210> SEQ ID NO 4
<211> LENGTH: 45
<212> TYPE: PRT
<213> ORGANISM: homo sapiens
```

<220> FEATURE:

<400> SEQUENCE: 4

Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp
        35                  40                  45

<210> SEQ ID NO 5
<211> LENGTH: 231
<212> TYPE: PRT
<213> ORGANISM: homo sapiens
<220> FEATURE:
<223> OTHER INFORMATION: IgG1 hinge

<400> SEQUENCE: 5

Glu Pro Lys Ser Pro Asp Lys Thr His Thr Cys Pro Pro Cys Pro Ala
1               5                   10                  15
Pro Pro Val Ala Gly Pro Ser Val Phe Leu Phe Pro Pro Lys Pro Lys
            20                  25                  30
Asp Thr Leu Met Ile Ala Arg Thr Pro Glu Val Thr Cys Val Val Val
            35                  40                  45
Asp Val Ser His Glu Asp Pro Glu Val Lys Phe Asn Trp Tyr Val Asp
    50                  55                  60
Gly Val Glu Val His Asn Ala Lys Thr Lys Pro Arg Glu Glu Gln Tyr
65                  70                  75                  80
Asn Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
            100                 105                 110
Pro Ala Pro Ile Glu Lys Thr Ile Ser Lys Ala Lys Gly Gln Pro Arg
        115                 120                 125
Glu Pro Gln Val Tyr Thr Leu Pro Pro Ser Arg Asp Glu Leu Thr Lys
    130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Lys
225                 230

<210> SEQ ID NO 6
<211> LENGTH: 24
<212> TYPE: PRT
<213> ORGANISM: homo sapiens
<220> FEATURE:
<223> OTHER INFORMATION: CD8alpha transmembrane domain

<400> SEQUENCE: 6

Ile Tyr Ile Trp Ala Pro Leu Ala Gly Thr Cys Gly Val Leu Leu Leu

```
                1               5                  10                 15
Ser Leu Val Ile Thr Leu Tyr Cys
            20

<210> SEQ ID NO 7
<211> LENGTH: 27
<212> TYPE: PRT
<213> ORGANISM: homo sapiens
<220> FEATURE:
<223> OTHER INFORMATION: 41BB transmembrane domain

<400> SEQUENCE: 7

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 8
<211> LENGTH: 42
<212> TYPE: PRT
<213> ORGANISM: homo sapiens
<220> FEATURE:
<223> OTHER INFORMATION: Fragment of 4-1BB (residues 214-255)

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 9
<211> LENGTH: 112
<212> TYPE: PRT
<213> ORGANISM: homo sapiens
<220> FEATURE:
<223> OTHER INFORMATION: fragment of T-cell surface glycoprotein CD3
      zeta chain

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 15
<212> TYPE: PRT
<213> ORGANISM: artificial sequence
<220> FEATURE:
<223> OTHER INFORMATION: description of artificial sequence: synthetic
```

```
                          oligopeptide
<220> FEATURE:
<223> OTHER INFORMATION: linker

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 119
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-50 heavy chain variable region

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
                20                  25                  30

Tyr Ile Asn Trp Val Arg Gln Ala Pro Gly Gln Gly Leu Glu Trp Met
            35                  40                  45

Gly Trp Ile Tyr Phe Ala Ser Gly Asn Ser Glu Tyr Asn Gln Lys Phe
        50                  55                  60

Thr Gly Arg Val Thr Met Thr Arg Asp Thr Ser Ile Asn Thr Ala Tyr
65                  70                  75                  80

Met Glu Leu Ser Ser Leu Thr Ser Glu Asp Thr Ala Val Tyr Phe Cys
                85                  90                  95

Ala Ser Leu Tyr Asp Tyr Asp Trp Tyr Phe Asp Val Trp Gly Gln Gly
                100                 105                 110

Thr Met Val Thr Val Ser Ser
            115

<210> SEQ ID NO 12
<211> LENGTH: 112
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-50 light chain variable region

<400> SEQUENCE: 12

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Ser Gln Ser
                85                  90                  95

Ser Ile Tyr Pro Trp Thr Phe Gly Gln Gly Thr Lys Leu Glu Ile Lys
                100                 105                 110
```

<210> SEQ ID NO 13
<211> LENGTH: 119
<212> TYPE: PRT
<213> ORGANISM: artificial sequence
<220> FEATURE:
<223> OTHER INFORMATION: description of artificial sequence: synthetic
    oligopeptide
<220> FEATURE:
<223> OTHER INFORMATION: BCMA-30 heavy chain variable region

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser
        115

<210> SEQ ID NO 14
<211> LENGTH: 112
<212> TYPE: PRT
<213> ORGANISM: artificial sequence
<220> FEATURE:
<223> OTHER INFORMATION: description of artificial sequence: synthetic
    oligopeptide
<220> FEATURE:
<223> OTHER INFORMATION: BCMA-30 light chain variable region

<400> SEQUENCE: 14

Asp Ile Val Met Thr Gln Thr Pro Leu Ser Leu Ser Val Thr Pro Gly
1               5                   10                  15

Glu Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Ala Asp Phe Thr Leu Lys Ile
65                  70                  75                  80

Ser Arg Val Glu Ala Glu Asp Val Gly Val Tyr Tyr Cys Ala Glu Thr
                85                  90                  95

Ser His Val Pro Trp Thr Phe Gly Gln Gly Thr Lys Leu Glu Ile Lys
            100                 105                 110

<210> SEQ ID NO 15
<211> LENGTH: 117
<212> TYPE: PRT
<213> ORGANISM: artificial sequence
<220> FEATURE:
<223> OTHER INFORMATION: description of artificial sequence: synthetic

```
<220> FEATURE:
<223> OTHER INFORMATION: C11D5.3 heavy chain variable region

<400> SEQUENCE: 15

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115

<210> SEQ ID NO 16
<211> LENGTH: 111
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: C11D5.3 light chain variable region

<400> SEQUENCE: 16

Asp Ile Val Leu Thr Gly Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 17
<211> LENGTH: 117
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: C13F12.1 heavy chain variable region

<400> SEQUENCE: 17

Gln Ile Gln Leu Val Gln Ser Gly Pro Glu Leu Lys Lys Pro Gly Glu
1               5                   10                  15
```

Thr Val Lys Ile Ser Cys Lys Ala Ser Gly Tyr Thr Phe Thr His Tyr
            20                  25                  30

Ser Met Asn Trp Val Lys Gln Ala Pro Gly Lys Gly Leu Lys Trp Met
            35                  40                  45

Gly Arg Ile Asn Thr Glu Thr Gly Glu Pro Leu Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Val Ile Asn Asn Leu Lys Asn Glu Asp Thr Ala Thr Phe Phe Cys
            85                  90                  95

Ser Asn Asp Tyr Leu Tyr Ser Cys Asp Tyr Trp Gly Arg Gly Thr Thr
            100                 105                 110

Leu Thr Val Ser Ser
            115

<210> SEQ ID NO 18
<211> LENGTH: 111
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: C13F12.1 light chain variable region

<400> SEQUENCE: 18

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Pro Pro
            35                  40                  45

Thr Leu Leu Ile Gln Leu Ala Ser Asn Val Gln Thr Gly Val Pro Ala
50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
            85                  90                  95

Thr Ile Pro Arg Thr Phe Gly Gly Gly Thr Lys Leu Glu Ile Lys
            100                 105                 110

<210> SEQ ID NO 19
<211> LENGTH: 436
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-50-1 polypeptide CAR sequence

<400> SEQUENCE: 19

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
            35                  40                  45

Gly Tyr Ile Tyr Pro Tyr Asn Gly Gly Thr Gly Tyr Asn Gln Lys Phe

```
                50                  55                  60
Lys Ser Lys Ala Thr Leu Thr Val Asp Asn Ser Ser Thr Ala Tyr
 65                  70                  75                  80

Met Asp Val Arg Ser Leu Thr Ser Glu Asp Ser Ala Val Tyr Cys
                     85                  90                  95

Ala Arg Gly Arg Pro Ala Met Asp Tyr Trp Gly Gln Gly Thr Ser Val
                    100                 105                 110

Thr Val Ser Ser Gly Gly Gly Gly Ser Gly Gly Gly Gly Ser Gly Gly
                115                 120                 125

Gly Gly Ser Asp Ile Val Leu Thr Gln Ser Pro Ala Ser Leu Ala Val
130                 135                 140

Ser Leu Gly Gln Arg Ala Thr Ile Ser Cys Arg Ala Ser Glu Ser Val
145                 150                 155                 160

Asp Asn Tyr Gly Ile Ser Phe Met Asn Trp Phe Gln Gln Lys Pro Gly
                165                 170                 175

Gln Pro Pro Lys Leu Leu Ile Tyr Ala Ala Ser Asn Gln Gly Ser Gly
                180                 185                 190

Val Pro Ala Arg Phe Ser Gly Ser Gly Ser Gly Thr Asp Phe Ser Leu
                195                 200                 205

Asn Ile His Pro Met Glu Glu Asp Asp Thr Ala Met Tyr Phe Cys Gln
210                 215                 220

Gln Ser Lys Glu Val Pro Trp Thr Phe Gly Gly Gly Thr Lys Leu Glu
225                 230                 235                 240

Ile Lys Gly Leu Ala Val Ser Thr Ile Ser Ser Phe Phe Pro Pro Gly
                245                 250                 255

Tyr Gln Ile Tyr Ile Trp Ala Pro Leu Ala Gly Thr Cys Gly Val Leu
                260                 265                 270

Leu Leu Ser Leu Val Ile Thr Leu Tyr Cys Lys Arg Gly Arg Lys Lys
                275                 280                 285

Leu Leu Tyr Ile Phe Lys Gln Pro Phe Met Arg Pro Val Gln Thr Thr
                290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
                340                 345                 350

Arg Glu Glu Tyr Asp Val Leu Asp Lys Arg Arg Gly Arg Asp Pro Glu
                355                 360                 365

Met Gly Gly Lys Pro Arg Arg Lys Asn Pro Gln Glu Gly Leu Tyr Asn
                370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
                420                 425                 430

Leu Pro Pro Arg
            435

<210> SEQ ID NO 20
<211> LENGTH: 439
<212> TYPE: PRT
<213> ORGANISM: artificial sequence
```

<220> FEATURE:
<223> OTHER INFORMATION: description of artificial sequence: synthetic
      oligopeptide
<220> FEATURE:
<223> OTHER INFORMATION: BCMA-50-2 polypeptide CAR sequence

<400> SEQUENCE: 20

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Leu Thr Val Asp Asn Ser Ser Thr Ala Tyr
65                  70                  75                  80

Met Asp Val Arg Ser Leu Thr Ser Glu Asp Ser Ala Val Tyr Tyr Cys
                85                  90                  95

Ala Arg Gly Arg Pro Ala Met Asp Tyr Trp Gly Gln Gly Thr Ser Val
            100                 105                 110

Thr Val Ser Ser Gly Gly Gly Ser Gly Gly Gly Ser Gly Gly
        115                 120                 125

Gly Gly Ser Asp Ile Val Leu Thr Gln Ser Pro Ala Ser Leu Ala Val
    130                 135                 140

Ser Leu Gly Gln Arg Ala Thr Ile Ser Cys Arg Ala Ser Glu Ser Val
145                 150                 155                 160

Asp Asn Tyr Gly Ile Ser Phe Met Asn Trp Phe Gln Gln Lys Pro Gly
                165                 170                 175

Gln Pro Pro Lys Leu Leu Ile Tyr Ala Ala Ser Asn Gln Gly Ser Gly
            180                 185                 190

Val Pro Ala Arg Phe Ser Gly Ser Gly Ser Gly Thr Asp Phe Ser Leu
        195                 200                 205

Asn Ile His Pro Met Glu Glu Asp Asp Thr Ala Met Tyr Phe Cys Gln
    210                 215                 220

Gln Ser Lys Glu Val Pro Trp Thr Phe Gly Gly Gly Thr Lys Leu Glu
225                 230                 235                 240

Ile Lys Gly Leu Ala Val Ser Thr Ile Ser Ser Phe Phe Pro Pro Gly
                245                 250                 255

Tyr Gln Ile Ile Ser Phe Phe Leu Ala Leu Thr Ser Thr Ala Leu Leu
            260                 265                 270

Phe Leu Leu Phe Phe Leu Thr Leu Arg Phe Ser Val Val Lys Arg Gly
        275                 280                 285

Arg Lys Lys Leu Leu Tyr Ile Phe Lys Gln Pro Phe Met Arg Pro Val
    290                 295                 300

Gln Thr Thr Gln Glu Glu Asp Gly Cys Ser Cys Arg Phe Pro Glu Glu
305                 310                 315                 320

Glu Glu Gly Gly Cys Glu Leu Arg Val Lys Phe Ser Arg Ser Ala Asp
                325                 330                 335

Ala Pro Ala Tyr Gln Gln Gly Gln Asn Gln Leu Tyr Asn Glu Leu Asn
            340                 345                 350

Leu Gly Arg Arg Glu Glu Tyr Asp Val Leu Asp Lys Arg Arg Gly Arg
        355                 360                 365

Asp Pro Glu Met Gly Gly Lys Pro Arg Arg Lys Asn Pro Gln Glu Gly
    370                 375                 380
```

```
Leu Tyr Asn Glu Leu Gln Lys Asp Lys Met Ala Glu Ala Tyr Ser Glu
385                 390                 395                 400

Ile Gly Met Lys Gly Glu Arg Arg Arg Gly Lys Gly His Asp Gly Leu
                405                 410                 415

Tyr Gln Gly Leu Ser Thr Ala Thr Lys Asp Thr Tyr Asp Ala Leu His
            420                 425                 430

Met Gln Ala Leu Pro Pro Arg
            435

<210> SEQ ID NO 21
<211> LENGTH: 465
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-50-3 polypeptide CAR sequence

<400> SEQUENCE: 21

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45

Gly Tyr Ile Tyr Pro Tyr Asn Gly Gly Thr Gly Tyr Asn Gln Lys Phe
        50                  55                  60

Lys Ser Lys Ala Thr Leu Thr Val Asp Asn Ser Ser Ser Thr Ala Tyr
65                  70                  75                  80

Met Asp Val Arg Ser Leu Thr Ser Glu Asp Ser Ala Val Tyr Tyr Cys
                85                  90                  95

Ala Arg Gly Arg Pro Ala Met Asp Tyr Trp Gly Gln Gly Thr Ser Val
            100                 105                 110

Thr Val Ser Ser Gly Gly Gly Ser Gly Gly Gly Ser Gly Gly
        115                 120                 125

Gly Gly Ser Asp Ile Val Leu Thr Gln Ser Pro Ala Ser Leu Ala Val
    130                 135                 140

Ser Leu Gly Gln Arg Ala Thr Ile Ser Cys Arg Ala Ser Glu Ser Val
145                 150                 155                 160

Asp Asn Tyr Gly Ile Ser Phe Met Asn Trp Phe Gln Gln Lys Pro Gly
                165                 170                 175

Gln Pro Pro Lys Leu Leu Ile Tyr Ala Ala Ser Asn Gln Gly Ser Gly
            180                 185                 190

Val Pro Ala Arg Phe Ser Gly Ser Gly Ser Gly Thr Asp Phe Ser Leu
        195                 200                 205

Asn Ile His Pro Met Glu Glu Asp Asp Thr Ala Met Tyr Phe Cys Gln
    210                 215                 220

Gln Ser Lys Glu Val Pro Trp Thr Phe Gly Gly Gly Thr Lys Leu Glu
225                 230                 235                 240

Ile Lys Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285
```

```
Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
                340                 345                 350

Leu Arg Val Lys Phe Ser Arg Ser Ala Asp Ala Pro Ala Tyr Gln Gln
                355                 360                 365

Gly Gln Asn Gln Leu Tyr Asn Glu Leu Asn Leu Gly Arg Arg Glu Glu
        370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
                420                 425                 430

Arg Arg Arg Gly Lys Gly His Asp Gly Leu Tyr Gln Gly Leu Ser Thr
                435                 440                 445

Ala Thr Lys Asp Thr Tyr Asp Ala Leu His Met Gln Ala Leu Pro Pro
        450                 455                 460

Arg
465

<210> SEQ ID NO 22
<211> LENGTH: 468
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-50-4 polypeptide CAR sequence

<400> SEQUENCE: 22

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45

Gly Tyr Ile Tyr Pro Tyr Asn Gly Gly Thr Gly Tyr Asn Gln Lys Phe
    50                  55                  60

Lys Ser Lys Ala Thr Leu Thr Val Asp Asn Ser Ser Thr Ala Tyr
65                  70                  75                  80

Met Asp Val Arg Ser Leu Thr Ser Glu Asp Ser Ala Val Tyr Tyr Cys
                85                  90                  95

Ala Arg Gly Arg Pro Ala Met Asp Tyr Trp Gly Gln Gly Thr Ser Val
                100                 105                 110

Thr Val Ser Ser Gly Gly Gly Gly Ser Gly Gly Gly Gly Ser Gly Gly
            115                 120                 125

Gly Gly Ser Asp Ile Val Leu Thr Gln Ser Pro Ala Ser Leu Ala Val
    130                 135                 140

Ser Leu Gly Gln Arg Ala Thr Ile Ser Cys Arg Ala Ser Glu Ser Val
145                 150                 155                 160
```

```
Asp Asn Tyr Gly Ile Ser Phe Met Asn Trp Phe Gln Gln Lys Pro Gly
                165                 170                 175

Gln Pro Pro Lys Leu Leu Ile Tyr Ala Ala Ser Asn Gln Gly Ser Gly
            180                 185                 190

Val Pro Ala Arg Phe Ser Gly Ser Gly Ser Gly Thr Asp Phe Ser Leu
        195                 200                 205

Asn Ile His Pro Met Glu Glu Asp Thr Ala Met Tyr Phe Cys Gln
    210                 215                 220

Gln Ser Lys Glu Val Pro Trp Thr Phe Gly Gly Gly Thr Lys Leu Glu
225                 230                 235                 240

Ile Lys Thr Thr Thr Pro Ala Pro Arg Pro Thr Pro Ala Pro Thr
                245                 250                 255

Ile Ala Ser Gln Pro Leu Ser Leu Arg Pro Glu Ala Cys Arg Pro Ala
                260                 265                 270

Ala Gly Gly Ala Val His Thr Arg Gly Leu Asp Phe Ala Cys Asp Ile
            275                 280                 285

Ile Ser Phe Phe Leu Ala Leu Thr Ser Thr Ala Leu Leu Phe Leu Leu
        290                 295                 300

Phe Phe Leu Thr Leu Arg Phe Ser Val Val Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
                420                 425                 430

Lys Gly Glu Arg Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
        450                 455                 460

Leu Pro Pro Arg
465

<210> SEQ ID NO 23
<211> LENGTH: 651
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-50-5 polypeptide CAR sequence

<400> SEQUENCE: 23

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30
```

-continued

```
Asn Met His Trp Val Lys Gln Ser His Gly Lys Ser Leu Glu Trp Ile
        35                  40                  45
Gly Tyr Ile Tyr Pro Tyr Asn Gly Gly Thr Gly Tyr Asn Gln Lys Phe
 50                  55                  60
Lys Ser Lys Ala Thr Leu Thr Val Asp Asn Ser Ser Thr Ala Tyr
 65                  70                  75                  80
Met Asp Val Arg Ser Leu Thr Ser Glu Asp Ser Ala Val Tyr Tyr Cys
                 85                  90                  95
Ala Arg Gly Arg Pro Ala Met Asp Tyr Trp Gly Gln Gly Thr Ser Val
             100                 105                 110
Thr Val Ser Ser Gly Gly Gly Gly Ser Gly Gly Gly Gly Ser Gly Gly
         115                 120                 125
Gly Gly Ser Asp Ile Val Leu Thr Gln Ser Pro Ala Ser Leu Ala Val
     130                 135                 140
Ser Leu Gly Gln Arg Ala Thr Ile Ser Cys Arg Ala Ser Glu Ser Val
145                 150                 155                 160
Asp Asn Tyr Gly Ile Ser Phe Met Asn Trp Phe Gln Lys Pro Gly
                 165                 170                 175
Gln Pro Pro Lys Leu Leu Ile Tyr Ala Ala Ser Asn Gln Gly Ser Gly
             180                 185                 190
Val Pro Ala Arg Phe Ser Gly Ser Gly Ser Gly Thr Asp Phe Ser Leu
         195                 200                 205
Asn Ile His Pro Met Glu Glu Asp Asp Thr Ala Met Tyr Phe Cys Gln
     210                 215                 220
Gln Ser Lys Glu Val Pro Trp Thr Phe Gly Gly Gly Thr Lys Leu Glu
225                 230                 235                 240
Ile Lys Glu Pro Lys Ser Pro Asp Lys Thr His Thr Cys Pro Pro Cys
                 245                 250                 255
Pro Ala Pro Pro Val Ala Gly Pro Ser Val Phe Leu Phe Pro Pro Lys
             260                 265                 270
Pro Lys Asp Thr Leu Met Ile Ala Arg Thr Pro Glu Val Thr Cys Val
         275                 280                 285
Val Val Asp Val Ser His Glu Asp Pro Glu Val Lys Phe Asn Trp Tyr
     290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                 325                 330                 335
Gln Asp Trp Leu Asn Gly Lys Glu Tyr Lys Cys Lys Val Ser Asn Lys
             340                 345                 350
Ala Leu Pro Ala Pro Ile Glu Lys Thr Ile Ser Lys Ala Lys Gly Gln
         355                 360                 365
Pro Arg Glu Pro Gln Val Tyr Thr Leu Pro Pro Ser Arg Asp Glu Leu
     370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                 405                 410                 415
Tyr Lys Thr Thr Pro Pro Val Leu Asp Ser Asp Gly Ser Phe Phe Leu
             420                 425                 430
Tyr Ser Lys Leu Thr Val Asp Lys Ser Arg Trp Gln Gln Gly Asn Val
         435                 440                 445
```

```
Phe Ser Cys Ser Val Met His Glu Ala Leu His Asn His Tyr Thr Gln
    450                 455                 460

Lys Ser Leu Ser Leu Ser Pro Gly Lys Ile Tyr Ile Trp Ala Pro Leu
465                 470                 475                 480

Ala Gly Thr Cys Gly Val Leu Leu Ser Leu Val Ile Thr Leu Tyr
            485                 490                 495

Cys Lys Arg Gly Arg Lys Lys Leu Leu Tyr Ile Phe Lys Gln Pro Phe
            500                 505                 510

Met Arg Pro Val Gln Thr Thr Gln Glu Glu Asp Gly Cys Ser Cys Arg
            515                 520                 525

Phe Pro Glu Glu Glu Glu Gly Gly Cys Glu Leu Arg Val Lys Phe Ser
530                 535                 540

Arg Ser Ala Asp Ala Pro Ala Tyr Gln Gln Gly Gln Asn Gln Leu Tyr
545                 550                 555                 560

Asn Glu Leu Asn Leu Gly Arg Arg Glu Glu Tyr Asp Val Leu Asp Lys
                565                 570                 575

Arg Arg Gly Arg Asp Pro Glu Met Gly Gly Lys Pro Arg Arg Lys Asn
            580                 585                 590

Pro Gln Glu Gly Leu Tyr Asn Glu Leu Gln Lys Asp Lys Met Ala Glu
            595                 600                 605

Ala Tyr Ser Glu Ile Gly Met Lys Gly Glu Arg Arg Arg Gly Lys Gly
610                 615                 620

His Asp Gly Leu Tyr Gln Gly Leu Ser Thr Ala Thr Lys Asp Thr Tyr
625                 630                 635                 640

Asp Ala Leu His Met Gln Ala Leu Pro Pro Arg
                645                 650

<210> SEQ ID NO 24
<211> LENGTH: 654
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-50-6 polypeptide CAR sequence

<400> SEQUENCE: 24

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Leu Thr Val Asp Asn Ser Ser Thr Ala Tyr
65                  70                  75                  80

Met Asp Val Arg Ser Leu Thr Ser Glu Asp Ser Ala Val Tyr Tyr Cys
                85                  90                  95

Ala Arg Gly Arg Pro Ala Met Asp Tyr Trp Gly Gln Gly Thr Ser Val
            100                 105                 110

Thr Val Ser Ser Gly Gly Gly Ser Gly Gly Gly Ser Gly Gly
        115                 120                 125

Gly Gly Ser Asp Ile Val Leu Thr Gln Ser Pro Ala Ser Leu Ala Val
    130                 135                 140
```

-continued

```
Ser Leu Gly Gln Arg Ala Thr Ile Ser Cys Arg Ala Ser Glu Ser Val
145                 150                 155                 160

Asp Asn Tyr Gly Ile Ser Phe Met Asn Trp Phe Gln Gln Lys Pro Gly
            165                 170                 175

Gln Pro Pro Lys Leu Leu Ile Tyr Ala Ala Ser Asn Gln Gly Ser Gly
            180                 185                 190

Val Pro Ala Arg Phe Ser Gly Ser Gly Ser Gly Thr Asp Phe Ser Leu
            195                 200                 205

Asn Ile His Pro Met Glu Glu Asp Thr Ala Met Tyr Phe Cys Gln
            210                 215                 220

Gln Ser Lys Glu Val Pro Trp Thr Phe Gly Gly Gly Thr Lys Leu Glu
225                 230                 235                 240

Ile Lys Glu Pro Lys Ser Pro Asp Lys Thr His Thr Cys Pro Pro Cys
            245                 250                 255

Pro Ala Pro Pro Val Ala Gly Pro Ser Val Phe Leu Phe Pro Pro Lys
            260                 265                 270

Pro Lys Asp Thr Leu Met Ile Ala Arg Thr Pro Glu Val Thr Cys Val
            275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
450                 455                 460

Lys Ser Leu Ser Leu Ser Pro Gly Lys Ile Ile Ser Phe Phe Leu Ala
465                 470                 475                 480

Leu Thr Ser Thr Ala Leu Leu Phe Leu Leu Phe Phe Leu Thr Leu Arg
            485                 490                 495

Phe Ser Val Val Lys Arg Gly Arg Lys Lys Leu Leu Tyr Ile Phe Lys
            500                 505                 510

Gln Pro Phe Met Arg Pro Val Gln Thr Thr Gln Glu Glu Asp Gly Cys
            515                 520                 525

Ser Cys Arg Phe Pro Glu Glu Glu Glu Gly Gly Cys Glu Leu Arg Val
            530                 535                 540

Lys Phe Ser Arg Ser Ala Asp Ala Pro Ala Tyr Gln Gln Gly Gln Asn
545                 550                 555                 560

Gln Leu Tyr Asn Glu Leu Asn Leu Gly Arg Arg Glu Glu Tyr Asp Val
```

```
                        565                 570                 575
Leu Asp Lys Arg Arg Gly Arg Asp Pro Glu Met Gly Lys Pro Arg
                580                 585                 590

Arg Lys Asn Pro Gln Glu Gly Leu Tyr Asn Glu Leu Gln Lys Asp Lys
            595                 600                 605

Met Ala Glu Ala Tyr Ser Glu Ile Gly Met Lys Gly Glu Arg Arg Arg
        610                 615                 620

Gly Lys Gly His Asp Gly Leu Tyr Gln Gly Leu Ser Thr Ala Thr Lys
625                 630                 635                 640

Asp Thr Tyr Asp Ala Leu His Met Gln Ala Leu Pro Pro Arg
                645                 650
```

<210> SEQ ID NO 25
<211> LENGTH: 434
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-30-1 polypeptide CAR sequence

<400> SEQUENCE: 25

```
Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Asp Ile Lys Met Thr Gln Ser Pro Ser Ser Met Tyr
    130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175

Lys Thr Leu Ile Tyr Arg Ala Asn Arg Leu Val Asp Gly Val Pro Ser
            180                 185                 190

Arg Phe Ser Gly Ser Gly Ser Gly Gln Asp Tyr Ser Leu Thr Ile Ser
        195                 200                 205

Ser Leu Glu Tyr Glu Asp Met Gly Ile Tyr Tyr Cys Leu Gln Tyr Asp
    210                 215                 220

Glu Phe Pro Leu Thr Phe Gly Ala Gly Thr Lys Leu Glu Leu Lys Arg
225                 230                 235                 240

Gly Leu Ala Val Ser Thr Ile Ser Ser Phe Phe Pro Pro Gly Tyr Gln
                245                 250                 255

Ile Tyr Ile Trp Ala Pro Leu Ala Gly Thr Cys Gly Val Leu Leu Leu
```

```
                    260                 265                 270
Ser Leu Val Ile Thr Leu Tyr Cys Lys Arg Gly Arg Lys Lys Leu Leu
                275                 280                 285

Tyr Ile Phe Lys Gln Pro Phe Met Arg Pro Val Gln Thr Thr Gln Glu
            290                 295                 300

Glu Asp Gly Cys Ser Cys Arg Phe Pro Glu Glu Glu Glu Gly Gly Cys
305                 310                 315                 320

Glu Leu Arg Val Lys Phe Ser Arg Ser Ala Asp Ala Pro Ala Tyr Gln
                325                 330                 335

Gln Gly Gln Asn Gln Leu Tyr Asn Glu Leu Asn Leu Gly Arg Arg Glu
            340                 345                 350

Glu Tyr Asp Val Leu Asp Lys Arg Arg Gly Arg Asp Pro Glu Met Gly
            355                 360                 365

Gly Lys Pro Arg Arg Lys Asn Pro Gln Glu Gly Leu Tyr Asn Glu Leu
            370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
            420                 425                 430

Pro Arg

<210> SEQ ID NO 26
<211> LENGTH: 437
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-30-2 polypeptide CAR sequence

<400> SEQUENCE: 26

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
                20                  25                  30

Asp Ile Asn Trp Val Asn Gln Arg Pro Gly Gln Gly Leu Glu Trp Ile
            35                  40                  45

Gly Trp Ile Tyr Pro Gly Asp Gly Ser Thr Lys Tyr Asn Glu Lys Phe
50                  55                  60

Lys Ala Lys Ala Thr Leu Thr Ala Asp Lys Ser Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Ser Gly Gly Gly Gly Ser Gly
            115                 120                 125

Gly Gly Gly Ser Asp Ile Lys Met Thr Gln Ser Pro Ser Ser Met Tyr
            130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175
```

```
Lys Thr Leu Ile Tyr Arg Ala Asn Arg Leu Val Asp Gly Val Pro Ser
            180                 185                 190

Arg Phe Ser Gly Ser Gly Ser Gly Gln Asp Tyr Ser Leu Thr Ile Ser
        195                 200                 205

Ser Leu Glu Tyr Glu Asp Met Gly Ile Tyr Tyr Cys Leu Gln Tyr Asp
210                 215                 220

Glu Phe Pro Leu Thr Phe Gly Ala Gly Thr Lys Leu Glu Leu Lys Arg
225                 230                 235                 240

Gly Leu Ala Val Ser Thr Ile Ser Ser Phe Phe Pro Pro Gly Tyr Gln
                245                 250                 255

Ile Ile Ser Phe Phe Leu Ala Leu Thr Ser Thr Ala Leu Leu Phe Leu
            260                 265                 270

Leu Phe Phe Leu Thr Leu Arg Phe Ser Val Val Lys Arg Gly Arg Lys
        275                 280                 285

Lys Leu Leu Tyr Ile Phe Lys Gln Pro Phe Met Arg Pro Val Gln Thr
            290                 295                 300

Thr Gln Glu Glu Asp Gly Cys Ser Cys Arg Phe Pro Glu Glu Glu Glu
305                 310                 315                 320

Gly Gly Cys Glu Leu Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
        355                 360                 365

Glu Met Gly Gly Lys Pro Arg Arg Lys Asn Pro Gln Glu Gly Leu Tyr
370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
            420                 425                 430

Ala Leu Pro Pro Arg
            435

<210> SEQ ID NO 27
<211> LENGTH: 463
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-30-3 polypeptide CAR sequence

<400> SEQUENCE: 27

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Ser Thr Ala Tyr
65                  70                  75                  80
```

```
Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Ser Gly Gly Gly Ser Gly
        115                 120                 125

Gly Gly Gly Ser Asp Ile Lys Met Thr Gln Ser Pro Ser Ser Met Tyr
        130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175

Lys Thr Leu Ile Tyr Arg Ala Asn Arg Leu Val Asp Gly Val Pro Ser
            180                 185                 190

Arg Phe Ser Gly Ser Gly Ser Gly Gln Asp Tyr Ser Leu Thr Ile Ser
            195                 200                 205

Ser Leu Glu Tyr Glu Asp Met Gly Ile Tyr Tyr Cys Leu Gln Tyr Asp
        210                 215                 220

Glu Phe Pro Leu Thr Phe Gly Ala Gly Thr Lys Leu Glu Leu Lys Arg
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
                260                 265                 270

Gly Ala Val His Thr Arg Gly Leu Asp Phe Ala Cys Asp Ile Tyr Ile
            275                 280                 285

Trp Ala Pro Leu Ala Gly Thr Cys Gly Val Leu Leu Leu Ser Leu Val
290                 295                 300

Ile Thr Leu Tyr Cys Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Glu Gly Gly Cys Glu Leu Arg
            340                 345                 350

Val Lys Phe Ser Arg Ser Ala Asp Ala Pro Ala Tyr Gln Gln Gly Gln
            355                 360                 365

Asn Gln Leu Tyr Asn Glu Leu Asn Leu Gly Arg Arg Glu Glu Tyr Asp
        370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
            435                 440                 445

Lys Asp Thr Tyr Asp Ala Leu His Met Gln Ala Leu Pro Pro Arg
        450                 455                 460

<210> SEQ ID NO 28
<211> LENGTH: 466
<212> TYPE: PRT
<213> ORGANISM: artificial sequence
<220> FEATURE:
```

<220> FEATURE:
<223> OTHER INFORMATION: description of artificial sequence: synthetic oligopeptide
<220> FEATURE:
<223> OTHER INFORMATION: BCMA-30-4 polypeptide CAR sequence

<400> SEQUENCE: 28

```
Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Ser Gly Gly Gly Ser Gly
        115                 120                 125

Gly Gly Gly Ser Asp Ile Lys Met Thr Gln Ser Pro Ser Ser Met Tyr
130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175

Lys Thr Leu Ile Tyr Arg Ala Asn Arg Leu Val Asp Gly Val Pro Ser
            180                 185                 190

Arg Phe Ser Gly Ser Gly Ser Gly Gln Asp Tyr Ser Leu Thr Ile Ser
        195                 200                 205

Ser Leu Glu Tyr Glu Asp Met Gly Ile Tyr Tyr Cys Leu Gln Tyr Asp
    210                 215                 220

Glu Phe Pro Leu Thr Phe Gly Ala Gly Thr Lys Leu Glu Leu Lys Arg
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Ile Ser
        275                 280                 285

Phe Phe Leu Ala Leu Thr Ser Thr Ala Leu Leu Phe Leu Leu Phe Phe
    290                 295                 300

Leu Thr Leu Arg Phe Ser Val Val Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380
```

```
Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
            405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465

<210> SEQ ID NO 29
<211> LENGTH: 649
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: BCMA-30-5 polypeptide CAR sequence

<400> SEQUENCE: 29

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
                20                  25                  30

Asp Ile Asn Trp Val Asn Gln Arg Pro Gly Gln Gly Leu Glu Trp Ile
            35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Asp Ile Lys Met Thr Gln Ser Pro Ser Ser Met Tyr
    130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175

Lys Thr Leu Ile Tyr Arg Ala Asn Arg Leu Val Asp Gly Val Pro Ser
            180                 185                 190

Arg Phe Ser Gly Ser Gly Ser Gly Gln Asp Tyr Ser Leu Thr Ile Ser
    195                 200                 205

Ser Leu Glu Tyr Glu Asp Met Gly Ile Tyr Tyr Cys Leu Gln Tyr Asp
210                 215                 220

Glu Phe Pro Leu Thr Phe Gly Ala Gly Thr Lys Leu Glu Leu Lys Arg
225                 230                 235                 240

Glu Pro Lys Ser Pro Asp Lys Thr His Thr Cys Pro Pro Cys Pro Ala
                245                 250                 255
```

Pro Pro Val Ala Gly Pro Ser Val Phe Leu Phe Pro Pro Lys Pro Lys
                260                 265                 270

Asp Thr Leu Met Ile Ala Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys Ile Tyr Ile Trp Ala Pro Leu Ala Gly
465                 470                 475                 480

Thr Cys Gly Val Leu Leu Leu Ser Leu Val Ile Thr Leu Tyr Cys Lys
                485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
        515                 520                 525

Glu Glu Glu Glu Gly Gly Cys Glu Leu Arg Val Lys Phe Ser Arg Ser
    530                 535                 540

Ala Asp Ala Pro Ala Tyr Gln Gln Gly Gln Asn Gln Leu Tyr Asn Glu
545                 550                 555                 560

Leu Asn Leu Gly Arg Arg Glu Glu Tyr Asp Val Leu Asp Lys Arg Arg
                565                 570                 575

Gly Arg Asp Pro Glu Met Gly Gly Lys Pro Arg Arg Lys Asn Pro Gln
            580                 585                 590

Glu Gly Leu Tyr Asn Glu Leu Gln Lys Asp Lys Met Ala Glu Ala Tyr
    595                 600                 605

Ser Glu Ile Gly Met Lys Gly Glu Arg Arg Arg Gly Lys Gly His Asp
610                 615                 620

Gly Leu Tyr Gln Gly Leu Ser Thr Ala Thr Lys Asp Thr Tyr Asp Ala
625                 630                 635                 640

Leu His Met Gln Ala Leu Pro Pro Arg
                645

<210> SEQ ID NO 30
<211> LENGTH: 652
<212> TYPE: PRT

<213> ORGANISM: artificial sequence
<220> FEATURE:
<223> OTHER INFORMATION: description of artificial sequence: synthetic oligopeptide
<220> FEATURE:
<223> OTHER INFORMATION: BCMA-30-6 polypeptide CAR sequence

<400> SEQUENCE: 30

```
Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
50                  55                  60

Lys Ala Lys Ala Thr Leu Thr Ala Asp Lys Ser Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Ser Gly Gly Gly Gly Ser Gly
        115                 120                 125

Gly Gly Gly Ser Asp Ile Lys Met Thr Gln Ser Pro Ser Ser Met Tyr
130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175

Lys Thr Leu Ile Tyr Arg Ala Asn Arg Leu Val Asp Gly Val Pro Ser
            180                 185                 190

Arg Phe Ser Gly Ser Gly Ser Gly Gln Asp Tyr Ser Leu Thr Ile Ser
        195                 200                 205

Ser Leu Glu Tyr Glu Asp Met Gly Ile Tyr Tyr Cys Leu Gln Tyr Asp
210                 215                 220

Glu Phe Pro Leu Thr Phe Gly Ala Gly Thr Lys Leu Glu Leu Lys Arg
225                 230                 235                 240

Glu Pro Lys Ser Pro Asp Lys Thr His Thr Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ala Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
```

```
                370                 375                 380
Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly Lys Ile Ile Ser Phe Phe Leu Ala Leu Thr
465                 470                 475                 480

Ser Thr Ala Leu Leu Phe Leu Leu Phe Phe Leu Thr Leu Arg Phe Ser
                485                 490                 495

Val Val Lys Arg Gly Arg Lys Lys Leu Leu Tyr Ile Phe Lys Gln Pro
                500                 505                 510

Phe Met Arg Pro Val Gln Thr Thr Gln Glu Glu Asp Gly Cys Ser Cys
                515                 520                 525

Arg Phe Pro Glu Glu Glu Glu Gly Gly Cys Glu Leu Arg Val Lys Phe
                530                 535                 540

Ser Arg Ser Ala Asp Ala Pro Ala Tyr Gln Gln Gly Gln Asn Gln Leu
545                 550                 555                 560

Tyr Asn Glu Leu Asn Leu Gly Arg Arg Glu Glu Tyr Asp Val Leu Asp
                565                 570                 575

Lys Arg Arg Gly Arg Asp Pro Glu Met Gly Gly Lys Pro Arg Arg Lys
                580                 585                 590

Asn Pro Gln Glu Gly Leu Tyr Asn Glu Leu Gln Lys Asp Lys Met Ala
                595                 600                 605

Glu Ala Tyr Ser Glu Ile Gly Met Lys Gly Glu Arg Arg Arg Gly Lys
                610                 615                 620

Gly His Asp Gly Leu Tyr Gln Gly Leu Ser Thr Ala Thr Lys Asp Thr
625                 630                 635                 640

Tyr Asp Ala Leu His Met Gln Ala Leu Pro Pro Arg
                645                 650
```

<210> SEQ ID NO 31
<211> LENGTH: 444
<212> TYPE: PRT
<213> ORGANISM: artificial sequence
<220> FEATURE:
<223> OTHER INFORMATION: description of artificial sequence: synthetic oligopeptide
<220> FEATURE:
<223> OTHER INFORMATION: C11D5.3-1 polypeptide CAR sequence

<400> SEQUENCE: 31

```
Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
                20                  25                  30

Val Val His Trp Leu Lys Gln Lys Pro Gly Gln Gly Leu Glu Trp Ile
                35                  40                  45

Gly Tyr Ile Asn Pro Tyr Asn Asp Gly Thr Lys Tyr Asn Glu Lys Phe
                50                  55                  60

Lys Gly Lys Ala Thr Leu Thr Ser Asp Lys Ser Ser Ser Thr Ala Tyr
```

```
            65                  70                  75                  80
Met Glu Val Ser Ser Leu Thr Ser Glu Asp Ser Ala Val Tyr Tyr Cys
                    85                  90                  95

Ala Arg Asp Tyr Arg Tyr Glu Val Tyr Gly Met Asp Tyr Trp Gly Gln
                100                 105                 110

Gly Thr Ser Val Thr Val Ser Ser Gly Gly Gly Gly Ser Gly Gly Gly
                115                 120                 125

Gly Ser Gly Gly Gly Gly Ser Asp Ile Val Leu Thr Gln Ser Pro Thr
        130                 135                 140

Ile Met Ser Ala Ser Pro Gly Glu Arg Val Thr Met Thr Cys Thr Ala
145                 150                 155                 160

Ser Ser Ser Val Asn Tyr Ile His Trp Tyr Gln Gln Lys Ser Gly Asp
                165                 170                 175

Ser Pro Leu Arg Trp Ile Phe Asp Thr Ser Lys Val Ala Ser Gly Val
                180                 185                 190

Pro Ala Arg Phe Ser Gly Ser Gly Ser Gly Thr Ser Tyr Ser Leu Thr
                195                 200                 205

Ile Ser Thr Met Glu Ala Glu Asp Ala Ala Thr Tyr Tyr Cys Gln Gln
        210                 215                 220

Trp Arg Ser Tyr Pro Leu Thr Phe Gly Asp Gly Thr Arg Leu Glu Leu
225                 230                 235                 240

Lys Arg Ala Asp Ala Ala Pro Thr Val Ser Gly Leu Ala Val Ser Thr
                245                 250                 255

Ile Ser Ser Phe Phe Pro Pro Gly Tyr Gln Ile Tyr Ile Trp Ala Pro
                260                 265                 270

Leu Ala Gly Thr Cys Gly Val Leu Leu Leu Ser Leu Val Ile Thr Leu
        275                 280                 285

Tyr Cys Lys Arg Gly Arg Lys Lys Leu Leu Tyr Ile Phe Lys Gln Pro
        290                 295                 300

Phe Met Arg Pro Val Gln Thr Thr Gln Glu Glu Asp Gly Cys Ser Cys
305                 310                 315                 320

Arg Phe Pro Glu Glu Glu Glu Gly Gly Cys Glu Leu Arg Val Lys Phe
                325                 330                 335

Ser Arg Ser Ala Asp Ala Pro Ala Tyr Gln Gln Gly Gln Asn Gln Leu
                340                 345                 350

Tyr Asn Glu Leu Asn Leu Gly Arg Arg Glu Glu Tyr Asp Val Leu Asp
                355                 360                 365

Lys Arg Arg Gly Arg Asp Pro Glu Met Gly Gly Lys Pro Arg Arg Lys
370                 375                 380

Asn Pro Gln Glu Gly Leu Tyr Asn Glu Leu Gln Lys Asp Lys Met Ala
385                 390                 395                 400

Glu Ala Tyr Ser Glu Ile Gly Met Lys Gly Glu Arg Arg Arg Gly Lys
                405                 410                 415

Gly His Asp Gly Leu Tyr Gln Gly Leu Ser Thr Ala Thr Lys Asp Thr
                420                 425                 430

Tyr Asp Ala Leu His Met Gln Ala Leu Pro Pro Arg
                435                 440

<210> SEQ ID NO 32
<211> LENGTH: 447
<212> TYPE: PRT
<213> ORGANISM: artificial sequence
<220> FEATURE:
<223> OTHER INFORMATION: description of artificial sequence: synthetic
      oligopeptide
```

<220> FEATURE:
<223> OTHER INFORMATION: C11D5.3-2 polypeptide CAR sequence

<400> SEQUENCE: 32

```
Glu Val Lys Leu Gln Glu Ser Gly Pro Glu Leu Val Lys Pro Gly Ala
1               5                   10                  15
Ser Val Lys Met Ser Cys Lys Ala Ser Gly Tyr Lys Phe Thr Asp Tyr
            20                  25                  30
Val Val His Trp Leu Lys Gln Lys Pro Gly Gln Gly Leu Glu Trp Ile
        35                  40                  45
Gly Tyr Ile Asn Pro Tyr Asn Asp Gly Thr Lys Tyr Asn Glu Lys Phe
    50                  55                  60
Lys Gly Lys Ala Thr Leu Thr Ser Asp Lys Ser Ser Thr Ala Tyr
65                  70                  75                  80
Met Glu Val Ser Ser Leu Thr Ser Glu Asp Ser Ala Val Tyr Tyr Cys
                85                  90                  95
Ala Arg Asp Tyr Arg Tyr Glu Val Tyr Gly Met Asp Tyr Trp Gly Gln
            100                 105                 110
Gly Thr Ser Val Thr Val Ser Ser Gly Gly Gly Ser Gly Gly Gly
        115                 120                 125
Gly Ser Gly Gly Gly Ser Asp Ile Val Leu Thr Gln Ser Pro Thr
    130                 135                 140
Ile Met Ser Ala Ser Pro Gly Glu Arg Val Thr Met Thr Cys Thr Ala
145                 150                 155                 160
Ser Ser Ser Val Asn Tyr Ile His Trp Tyr Gln Gln Lys Ser Gly Asp
                165                 170                 175
Ser Pro Leu Arg Trp Ile Phe Asp Thr Ser Lys Val Ala Ser Gly Val
            180                 185                 190
Pro Ala Arg Phe Ser Gly Ser Gly Ser Gly Thr Ser Tyr Ser Leu Thr
        195                 200                 205
Ile Ser Thr Met Glu Ala Glu Asp Ala Ala Thr Tyr Tyr Cys Gln Gln
    210                 215                 220
Trp Arg Ser Tyr Pro Leu Thr Phe Gly Asp Gly Thr Arg Leu Glu Leu
225                 230                 235                 240
Lys Arg Ala Asp Ala Ala Pro Thr Val Ser Gly Leu Ala Val Ser Thr
                245                 250                 255
Ile Ser Ser Phe Phe Pro Pro Gly Tyr Gln Ile Ile Ser Phe Phe Leu
            260                 265                 270
Ala Leu Thr Ser Thr Ala Leu Leu Phe Leu Leu Phe Phe Leu Thr Leu
        275                 280                 285
Arg Phe Ser Val Val Lys Arg Gly Arg Lys Lys Leu Leu Tyr Ile Phe
    290                 295                 300
Lys Gln Pro Phe Met Arg Pro Val Gln Thr Thr Gln Glu Glu Asp Gly
305                 310                 315                 320
Cys Ser Cys Arg Phe Pro Glu Glu Glu Glu Gly Gly Cys Glu Leu Arg
                325                 330                 335
Val Lys Phe Ser Arg Ser Ala Asp Ala Pro Ala Tyr Gln Gln Gly Gln
            340                 345                 350
Asn Gln Leu Tyr Asn Glu Leu Asn Leu Gly Arg Arg Glu Glu Tyr Asp
        355                 360                 365
Val Leu Asp Lys Arg Arg Gly Arg Asp Pro Glu Met Gly Gly Lys Pro
    370                 375                 380
Arg Arg Lys Asn Pro Gln Glu Gly Leu Tyr Asn Glu Leu Gln Lys Asp
385                 390                 395                 400
```

```
Lys Met Ala Glu Ala Tyr Ser Glu Ile Gly Met Lys Gly Glu Arg Arg
                405                 410                 415

Arg Gly Lys Gly His Asp Gly Leu Tyr Gln Gly Leu Ser Thr Ala Thr
            420                 425                 430

Lys Asp Thr Tyr Asp Ala Leu His Met Gln Ala Leu Pro Pro Arg
        435                 440                 445

<210> SEQ ID NO 33
<211> LENGTH: 473
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: C11D5.3-3 polypeptide CAR sequence

<400> SEQUENCE: 33

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30

Val Val His Trp Leu Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Gly Ser Asp Ile Val Leu Thr Gln Ser Pro Thr
    130                 135                 140

Ile Met Ser Ala Ser Pro Gly Glu Arg Val Thr Met Thr Cys Thr Ala
145                 150                 155                 160

Ser Ser Ser Val Asn Tyr Ile His Trp Tyr Gln Gln Lys Ser Gly Asp
                165                 170                 175

Ser Pro Leu Arg Trp Ile Phe Asp Thr Ser Lys Val Ala Ser Gly Val
            180                 185                 190

Pro Ala Arg Phe Ser Gly Ser Gly Ser Gly Thr Ser Tyr Ser Leu Thr
        195                 200                 205

Ile Ser Thr Met Glu Ala Glu Asp Ala Ala Thr Tyr Tyr Cys Gln Gln
    210                 215                 220

Trp Arg Ser Tyr Pro Leu Thr Phe Gly Asp Gly Thr Arg Leu Glu Leu
225                 230                 235                 240

Lys Arg Ala Asp Ala Ala Pro Thr Val Ser Thr Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
        275                 280                 285

Gly Leu Asp Phe Ala Cys Asp Ile Tyr Ile Trp Ala Pro Leu Ala Gly
    290                 295                 300
```

```
Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
                355                 360                 365

Ala Asp Ala Pro Ala Tyr Gln Gln Gly Gln Asn Gln Leu Tyr Asn Glu
370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
                420                 425                 430

Ser Glu Ile Gly Met Lys Gly Glu Arg Arg Arg Gly Lys Gly His Asp
                435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470

<210> SEQ ID NO 34
<211> LENGTH: 476
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: C11D5.3-4 polypeptide CAR sequence

<400> SEQUENCE: 34

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
                20                  25                  30

Val Val His Trp Leu Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
                100                 105                 110

Gly Thr Ser Val Thr Val Ser Ser Gly Gly Gly Ser Gly Gly Gly
            115                 120                 125

Gly Ser Gly Gly Gly Gly Ser Asp Ile Val Leu Thr Gln Ser Pro Thr
    130                 135                 140

Ile Met Ser Ala Ser Pro Gly Glu Arg Val Thr Met Thr Cys Thr Ala
145                 150                 155                 160

Ser Ser Ser Val Asn Tyr Ile His Trp Tyr Gln Gln Lys Ser Gly Asp
                165                 170                 175
```

```
Ser Pro Leu Arg Trp Ile Phe Asp Thr Ser Lys Val Ala Ser Gly Val
            180                 185                 190

Pro Ala Arg Phe Ser Gly Ser Gly Ser Gly Thr Ser Tyr Ser Leu Thr
            195                 200                 205

Ile Ser Thr Met Glu Ala Glu Asp Ala Ala Thr Tyr Tyr Cys Gln Gln
210                 215                 220

Trp Arg Ser Tyr Pro Leu Thr Phe Gly Asp Gly Thr Arg Leu Glu Leu
225                 230                 235                 240

Lys Arg Ala Asp Ala Ala Pro Thr Val Ser Thr Thr Pro Ala Pro
            245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
            275                 280                 285

Gly Leu Asp Phe Ala Cys Asp Ile Ile Ser Phe Phe Leu Ala Leu Thr
            290                 295                 300

Ser Thr Ala Leu Leu Phe Leu Leu Phe Phe Leu Thr Leu Arg Phe Ser
305                 310                 315                 320

Val Val Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
            340                 345                 350

Arg Phe Pro Glu Glu Glu Glu Gly Gly Cys Glu Leu Arg Val Lys Phe
            355                 360                 365

Ser Arg Ser Ala Asp Ala Pro Ala Tyr Gln Gln Gly Gln Asn Gln Leu
            370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
            435                 440                 445

Gly His Asp Gly Leu Tyr Gln Gly Leu Ser Thr Ala Thr Lys Asp Thr
            450                 455                 460

Tyr Asp Ala Leu His Met Gln Ala Leu Pro Pro Arg
465                 470                 475

<210> SEQ ID NO 35
<211> LENGTH: 659
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: C11D5.3-5 polypeptide CAR sequence

<400> SEQUENCE: 35

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30

Val Val His Trp Leu Lys Gln Lys Pro Gly Gln Gly Leu Glu Trp Ile
        35                  40                  45
```

-continued

```
Gly Tyr Ile Asn Pro Tyr Asn Asp Gly Thr Lys Tyr Asn Glu Lys Phe
     50                  55                  60

Lys Gly Lys Ala Thr Leu Thr Ser Asp Lys Ser Ser Thr Ala Tyr
 65                  70                  75                  80

Met Glu Val Ser Ser Leu Thr Ser Glu Asp Ser Ala Val Tyr Tyr Cys
                 85                  90                  95

Ala Arg Asp Tyr Arg Tyr Glu Val Tyr Gly Met Asp Tyr Trp Gly Gln
                100                 105                 110

Gly Thr Ser Val Thr Val Ser Ser Gly Gly Gly Ser Gly Gly
                115                 120                 125

Gly Ser Gly Gly Gly Ser Asp Ile Val Leu Thr Gln Ser Pro Thr
    130                 135                 140

Ile Met Ser Ala Ser Pro Gly Glu Arg Val Thr Met Thr Cys Thr Ala
145                 150                 155                 160

Ser Ser Ser Val Asn Tyr Ile His Trp Tyr Gln Gln Lys Ser Gly Asp
                165                 170                 175

Ser Pro Leu Arg Trp Ile Phe Asp Thr Ser Lys Val Ala Ser Gly Val
            180                 185                 190

Pro Ala Arg Phe Ser Gly Ser Gly Ser Gly Thr Ser Tyr Ser Leu Thr
        195                 200                 205

Ile Ser Thr Met Glu Ala Glu Asp Ala Ala Thr Tyr Tyr Cys Gln Gln
210                 215                 220

Trp Arg Ser Tyr Pro Leu Thr Phe Gly Asp Gly Thr Arg Leu Glu Leu
225                 230                 235                 240

Lys Arg Ala Asp Ala Ala Pro Thr Val Ser Glu Pro Lys Ser Pro Asp
                245                 250                 255

Lys Thr His Thr Cys Pro Pro Cys Pro Ala Pro Pro Val Ala Gly Pro
                260                 265                 270

Ser Val Phe Leu Phe Pro Pro Lys Pro Lys Asp Thr Leu Met Ile Ala
            275                 280                 285

Arg Thr Pro Glu Val Thr Cys Val Val Val Asp Val Ser His Glu Asp
        290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460
```

```
Ala Leu His Asn His Tyr Thr Gln Lys Ser Leu Ser Leu Ser Pro Gly
465                 470                 475                 480

Lys Ile Tyr Ile Trp Ala Pro Leu Ala Gly Thr Cys Gly Val Leu Leu
            485                 490                 495

Leu Ser Leu Val Ile Thr Leu Tyr Cys Lys Arg Gly Arg Lys Lys Leu
        500                 505                 510

Leu Tyr Ile Phe Lys Gln Pro Phe Met Arg Pro Val Gln Thr Thr Gln
    515                 520                 525

Glu Glu Asp Gly Cys Ser Cys Arg Phe Pro Glu Glu Glu Gly Gly
530                 535                 540

Cys Glu Leu Arg Val Lys Phe Ser Arg Ser Ala Asp Ala Pro Ala Tyr
545                 550                 555                 560

Gln Gln Gly Gln Asn Gln Leu Tyr Asn Glu Leu Asn Leu Gly Arg Arg
                565                 570                 575

Glu Glu Tyr Asp Val Leu Asp Lys Arg Arg Gly Arg Asp Pro Glu Met
            580                 585                 590

Gly Gly Lys Pro Arg Arg Lys Asn Pro Gln Glu Gly Leu Tyr Asn Glu
        595                 600                 605

Leu Gln Lys Asp Lys Met Ala Glu Ala Tyr Ser Glu Ile Gly Met Lys
    610                 615                 620

Gly Glu Arg Arg Arg Gly Lys Gly His Asp Gly Leu Tyr Gln Gly Leu
625                 630                 635                 640

Ser Thr Ala Thr Lys Asp Thr Tyr Asp Ala Leu His Met Gln Ala Leu
                645                 650                 655

Pro Pro Arg

<210> SEQ ID NO 36
<211> LENGTH: 662
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: C11D5.3-6 polypeptide CAR sequence

<400> SEQUENCE: 36

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30

Val Val His Trp Leu Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Val Leu Thr Gln Ser Pro Thr
    130                 135                 140

Ile Met Ser Ala Ser Pro Gly Glu Arg Val Thr Met Thr Cys Thr Ala
```

```
            145                 150                 155                 160
        Ser Ser Ser Val Asn Tyr Ile His Trp Tyr Gln Gln Lys Ser Gly Asp
                        165                 170                 175

Ser Pro Leu Arg Trp Ile Phe Asp Thr Ser Lys Val Ala Ser Gly Val
                        180                 185                 190

Pro Ala Arg Phe Ser Gly Ser Gly Ser Gly Thr Ser Tyr Ser Leu Thr
                        195                 200                 205

Ile Ser Thr Met Glu Ala Glu Asp Ala Ala Thr Tyr Tyr Cys Gln Gln
                        210                 215                 220

Trp Arg Ser Tyr Pro Leu Thr Phe Gly Asp Gly Thr Arg Leu Glu Leu
        225                 230                 235                 240

Lys Arg Ala Asp Ala Ala Pro Thr Val Ser Glu Pro Lys Ser Pro Asp
                        245                 250                 255

Lys Thr His Thr Cys Pro Pro Cys Pro Ala Pro Pro Val Ala Gly Pro
                        260                 265                 270

Ser Val Phe Leu Phe Pro Pro Lys Pro Lys Asp Thr Leu Met Ile Ala
                        275                 280                 285

Arg Thr Pro Glu Val Thr Cys Val Val Val Asp Val Ser His Glu Asp
                        290                 295                 300

Pro Glu Val Lys Phe Asn Trp Tyr Val Asp Gly Val Glu Val His Asn
        305                 310                 315                 320

Ala Lys Thr Lys Pro Arg Glu Glu Gln Tyr Asn Ser Thr Tyr Arg Val
                        325                 330                 335

Val Ser Val Leu Thr Val Leu His Gln Asp Trp Leu Asn Gly Lys Glu
                        340                 345                 350

Tyr Lys Cys Lys Val Ser Asn Lys Ala Leu Pro Ala Pro Ile Glu Lys
                        355                 360                 365

Thr Ile Ser Lys Ala Lys Gly Gln Pro Arg Glu Pro Gln Val Tyr Thr
                        370                 375                 380

Leu Pro Pro Ser Arg Asp Glu Leu Thr Lys Asn Gln Val Ser Leu Thr
        385                 390                 395                 400

Cys Leu Val Lys Gly Phe Tyr Pro Ser Asp Ile Ala Val Glu Trp Glu
                        405                 410                 415

Ser Asn Gly Gln Pro Glu Asn Asn Tyr Lys Thr Thr Pro Pro Val Leu
                        420                 425                 430

Asp Ser Asp Gly Ser Phe Phe Leu Tyr Ser Lys Leu Thr Val Asp Lys
                        435                 440                 445

Ser Arg Trp Gln Gln Gly Asn Val Phe Ser Cys Ser Val Met His Glu
                        450                 455                 460

Ala Leu His Asn His Tyr Thr Gln Lys Ser Leu Ser Leu Ser Pro Gly
        465                 470                 475                 480

Lys Ile Ile Ser Phe Phe Leu Ala Leu Thr Ser Thr Ala Leu Leu Phe
                        485                 490                 495

Leu Leu Phe Phe Leu Thr Leu Arg Phe Ser Val Val Lys Arg Gly Arg
                        500                 505                 510

Lys Lys Leu Leu Tyr Ile Phe Lys Gln Pro Phe Met Arg Pro Val Gln
                        515                 520                 525

Thr Thr Gln Glu Glu Asp Gly Cys Ser Cys Arg Phe Pro Glu Glu Glu
                        530                 535                 540

Glu Gly Gly Cys Glu Leu Arg Val Lys Phe Ser Arg Ser Ala Asp Ala
        545                 550                 555                 560

Pro Ala Tyr Gln Gln Gly Gln Asn Gln Leu Tyr Asn Glu Leu Asn Leu
                        565                 570                 575
```

```
Gly Arg Arg Glu Glu Tyr Asp Val Leu Asp Lys Arg Gly Arg Asp
            580                 585                 590

Pro Glu Met Gly Gly Lys Pro Arg Arg Lys Asn Pro Gln Glu Gly Leu
            595                 600                 605

Tyr Asn Glu Leu Gln Lys Asp Lys Met Ala Glu Ala Tyr Ser Glu Ile
            610                 615                 620

Gly Met Lys Gly Glu Arg Arg Arg Gly Lys Gly His Asp Gly Leu Tyr
625                 630                 635                 640

Gln Gly Leu Ser Thr Ala Thr Lys Asp Thr Tyr Asp Ala Leu His Met
            645                 650                 655

Gln Ala Leu Pro Pro Arg
            660

<210> SEQ ID NO 37
<211> LENGTH: 440
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: C13F12-1 polypeptide CAR sequence

<400> SEQUENCE: 37

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Ser Gly Gly Gly Gly Ser
        115                 120                 125

Gly Gly Gly Gly Ser Asn Ile Met Leu Thr Gln Ser Pro Ser Ser Leu
    130                 135                 140

Ala Val Ser Ala Gly Glu Lys Val Thr Met Ser Cys Lys Ser Ser Gln
145                 150                 155                 160

Ser Val Phe Phe Ser Ser Ser Gln Lys Asn Tyr Leu Ala Trp Tyr Gln
                165                 170                 175

Gln Ile Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ser Glu Asp Leu Ala Ile
    210                 215                 220

Tyr Tyr Cys His Gln Tyr Leu Ser Ser Arg Thr Phe Gly Gly Gly Thr
225                 230                 235                 240

Lys Leu Glu Ile Lys Arg Gly Leu Ala Val Ser Thr Ile Ser Ser Phe
                245                 250                 255
```

```
Phe Pro Pro Gly Tyr Gln Ile Tyr Ile Trp Ala Pro Leu Ala Gly Thr
            260                 265                 270

Cys Gly Val Leu Leu Ser Leu Val Ile Thr Leu Tyr Cys Lys Arg
        275                 280                 285

Gly Arg Lys Lys Leu Leu Tyr Ile Phe Lys Gln Pro Phe Met Arg Pro
        290                 295                 300

Val Gln Thr Thr Gln Glu Glu Asp Gly Cys Ser Cys Arg Phe Pro Glu
305                 310                 315                 320

Glu Glu Glu Gly Gly Cys Glu Leu Arg Val Lys Phe Ser Arg Ser Ala
            325                 330                 335

Asp Ala Pro Ala Tyr Gln Gln Gly Gln Asn Gln Leu Tyr Asn Glu Leu
            340                 345                 350

Asn Leu Gly Arg Arg Glu Glu Tyr Asp Val Leu Asp Lys Arg Arg Gly
            355                 360                 365

Arg Asp Pro Glu Met Gly Gly Lys Pro Arg Arg Lys Asn Pro Gln Glu
        370                 375                 380

Gly Leu Tyr Asn Glu Leu Gln Lys Asp Lys Met Ala Glu Ala Tyr Ser
385                 390                 395                 400

Glu Ile Gly Met Lys Gly Glu Arg Arg Arg Gly Lys Gly His Asp Gly
            405                 410                 415

Leu Tyr Gln Gly Leu Ser Thr Ala Thr Lys Asp Thr Tyr Asp Ala Leu
            420                 425                 430

His Met Gln Ala Leu Pro Pro Arg
        435                 440

<210> SEQ ID NO 38
<211> LENGTH: 443
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: C13F12-2 polypeptide CAR sequence

<400> SEQUENCE: 38

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Ser Gly Gly Gly Gly Ser
        115                 120                 125

Gly Gly Gly Gly Ser Asn Ile Met Leu Thr Gln Ser Pro Ser Ser Leu
    130                 135                 140

Ala Val Ser Ala Gly Glu Lys Val Thr Met Ser Cys Lys Ser Ser Gln
145                 150                 155                 160
```

-continued

Ser Val Phe Phe Ser Ser Gln Lys Asn Tyr Leu Ala Trp Tyr Gln
            165                 170                 175

Gln Ile Pro Gly Gln Ser Pro Lys Leu Leu Ile Tyr Trp Ala Ser Thr
        180                 185                 190

Arg Glu Ser Gly Val Pro Asp Arg Phe Thr Gly Ser Gly Ser Gly Thr
    195                 200                 205

Asp Phe Thr Leu Thr Ile Ser Ser Val Gln Ser Glu Asp Leu Ala Ile
    210                 215                 220

Tyr Tyr Cys His Gln Tyr Leu Ser Ser Arg Thr Phe Gly Gly Gly Thr
225                 230                 235                 240

Lys Leu Glu Ile Lys Arg Gly Leu Ala Val Ser Thr Ile Ser Ser Phe
                245                 250                 255

Phe Pro Pro Gly Tyr Gln Ile Ile Ser Phe Phe Leu Ala Leu Thr Ser
            260                 265                 270

Thr Ala Leu Leu Phe Leu Leu Phe Phe Leu Thr Leu Arg Phe Ser Val
        275                 280                 285

Val Lys Arg Gly Arg Lys Lys Leu Leu Tyr Ile Phe Lys Gln Pro Phe
    290                 295                 300

Met Arg Pro Val Gln Thr Thr Gln Glu Glu Asp Gly Cys Ser Cys Arg
305                 310                 315                 320

Phe Pro Glu Glu Glu Glu Gly Gly Cys Glu Leu Arg Val Lys Phe Ser
                325                 330                 335

Arg Ser Ala Asp Ala Pro Ala Tyr Gln Gln Gly Gln Asn Gln Leu Tyr
            340                 345                 350

Asn Glu Leu Asn Leu Gly Arg Arg Glu Glu Tyr Asp Val Leu Asp Lys
        355                 360                 365

Arg Arg Gly Arg Asp Pro Glu Met Gly Gly Lys Pro Arg Arg Lys Asn
    370                 375                 380

Pro Gln Glu Gly Leu Tyr Asn Glu Leu Gln Lys Asp Lys Met Ala Glu
385                 390                 395                 400

Ala Tyr Ser Glu Ile Gly Met Lys Gly Glu Arg Arg Arg Gly Lys Gly
                405                 410                 415

His Asp Gly Leu Tyr Gln Gly Leu Ser Thr Ala Thr Lys Asp Thr Tyr
            420                 425                 430

Asp Ala Leu His Met Gln Ala Leu Pro Pro Arg
        435                 440

<210> SEQ ID NO 39
<211> LENGTH: 469
<212> TYPE: PRT
<213> ORGANISM: artificial sequence
<220> FEATURE:
<223> OTHER INFORMATION: description of artificial sequence: synthetic
     oligopeptide
<220> FEATURE:
<223> OTHER INFORMATION: C13F12-3 polypeptide CAR sequence

<400> SEQUENCE: 39

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

```
Lys Gly Lys Ala Thr Leu Thr Ala Asp Lys Ser Thr Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Val Arg Leu Arg Tyr Phe Asp Val Trp Gly Ala Gly Thr
             100                 105                 110

Thr Val Thr Val Ser Ser Gly Gly Gly Gly Ser Gly Gly Gly Gly Ser
             115                 120                 125

Gly Gly Gly Gly Ser Asn Ile Met Leu Thr Gln Ser Pro Ser Ser Leu
         130                 135                 140

Ala Val Ser Ala Gly Glu Lys Val Thr Met Ser Cys Lys Ser Ser Gln
145                 150                 155                 160

Ser Val Phe Phe Ser Ser Gln Lys Asn Tyr Leu Ala Trp Tyr Gln
                 165                 170                 175

Gln Ile Pro Gly Gln Ser Pro Lys Leu Leu Ile Tyr Trp Ala Ser Thr
             180                 185                 190

Arg Glu Ser Gly Val Pro Asp Arg Phe Thr Gly Ser Gly Ser Gly Thr
             195                 200                 205

Asp Phe Thr Leu Thr Ile Ser Ser Val Gln Ser Glu Asp Leu Ala Ile
             210                 215                 220

Tyr Tyr Cys His Gln Tyr Leu Ser Ser Arg Thr Phe Gly Gly Gly Thr
225                 230                 235                 240

Lys Leu Glu Ile Lys Arg Thr Thr Thr Pro Ala Pro Arg Pro Pro Thr
             245                 250                 255

Pro Ala Pro Thr Ile Ala Ser Gln Pro Leu Ser Leu Arg Pro Glu Ala
             260                 265                 270

Cys Arg Pro Ala Ala Gly Gly Ala Val His Thr Arg Gly Leu Asp Phe
         275                 280                 285

Ala Cys Asp Ile Tyr Ile Trp Ala Pro Leu Ala Gly Thr Cys Gly Val
         290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
             325                 330                 335

Thr Gln Glu Glu Asp Gly Cys Ser Cys Arg Phe Pro Glu Glu Glu Glu
             340                 345                 350

Gly Gly Cys Glu Leu Arg Val Lys Phe Ser Arg Ser Ala Asp Ala Pro
         355                 360                 365

Ala Tyr Gln Gln Gly Gln Asn Gln Leu Tyr Asn Glu Leu Asn Leu Gly
         370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
             405                 410                 415

Asn Glu Leu Gln Lys Asp Lys Met Ala Glu Ala Tyr Ser Glu Ile Gly
             420                 425                 430

Met Lys Gly Glu Arg Arg Arg Gly Lys Gly His Asp Gly Leu Tyr Gln
             435                 440                 445

Gly Leu Ser Thr Ala Thr Lys Asp Thr Tyr Asp Ala Leu His Met Gln
         450                 455                 460

Ala Leu Pro Pro Arg
465
```

<210> SEQ ID NO 40
<211> LENGTH: 472
<212> TYPE: PRT
<213> ORGANISM: artificial sequence
<220> FEATURE:
<223> OTHER INFORMATION: description of artificial sequence: synthetic oligopeptide
<220> FEATURE:
<223> OTHER INFORMATION: C13F12-4 polypeptide CAR sequence

<400> SEQUENCE: 40

```
Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Gly Ser Gly Gly Gly Gly Ser
        115                 120                 125

Gly Gly Gly Gly Ser Asn Ile Met Leu Thr Gln Ser Pro Ser Ser Leu
    130                 135                 140

Ala Val Ser Ala Gly Glu Lys Val Thr Met Ser Cys Lys Ser Ser Gln
145                 150                 155                 160

Ser Val Phe Phe Ser Ser Gln Lys Asn Tyr Leu Ala Trp Tyr Gln
                165                 170                 175

Gln Ile Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ser Glu Asp Leu Ala Ile
    210                 215                 220

Tyr Tyr Cys His Gln Tyr Leu Ser Ser Arg Thr Phe Gly Gly Gly Thr
225                 230                 235                 240

Lys Leu Glu Ile Lys Arg Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Ile Ser Phe Phe Leu Ala Leu Thr Ser Thr Ala Leu
    290                 295                 300

Leu Phe Leu Leu Phe Phe Leu Thr Leu Arg Phe Ser Val Val Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350
```

```
Glu Glu Glu Gly Gly Cys Glu Leu Arg Val Lys Phe Ser Arg Ser Ala
            355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
            435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470
```

<210> SEQ ID NO 41  
<211> LENGTH: 655  
<212> TYPE: PRT  
<213> ORGANISM: artificial sequence  
<220> FEATURE:  
<223> OTHER INFORMATION: description of artificial sequence: synthetic oligopeptide  
<220> FEATURE:  
<223> OTHER INFORMATION: C13F12-5 polypeptide CAR sequence

<400> SEQUENCE: 41

```
Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Gly Ser Gly Gly Gly Gly Ser
        115                 120                 125

Gly Gly Gly Gly Ser Asn Ile Met Leu Thr Gln Ser Pro Ser Ser Leu
    130                 135                 140

Ala Val Ser Ala Gly Glu Lys Val Thr Met Ser Cys Lys Ser Ser Gln
145                 150                 155                 160

Ser Val Phe Phe Ser Ser Ser Gln Lys Asn Tyr Leu Ala Trp Tyr Gln
                165                 170                 175

Gln Ile Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ser Glu Asp Leu Ala Ile
    210                 215                 220
```

Tyr Tyr Cys His Gln Tyr Leu Ser Ser Arg Thr Phe Gly Gly Gly Thr
225                 230                 235                 240

Lys Leu Glu Ile Lys Arg Glu Pro Lys Ser Pro Asp Lys Thr His Thr
            245                 250                 255

Cys Pro Pro Cys Pro Ala Pro Pro Val Ala Gly Pro Ser Val Phe Leu
        260                 265                 270

Phe Pro Pro Lys Pro Lys Asp Thr Leu Met Ile Ala Arg Thr Pro Glu
    275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
                340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Ile Tyr Ile
465                 470                 475                 480

Trp Ala Pro Leu Ala Gly Thr Cys Gly Val Leu Leu Leu Ser Leu Val
                485                 490                 495

Ile Thr Leu Tyr Cys Lys Arg Gly Arg Lys Lys Leu Leu Tyr Ile Phe
                500                 505                 510

Lys Gln Pro Phe Met Arg Pro Val Gln Thr Thr Gln Glu Glu Asp Gly
            515                 520                 525

Cys Ser Cys Arg Phe Pro Glu Glu Glu Glu Gly Gly Cys Glu Leu Arg
530                 535                 540

Val Lys Phe Ser Arg Ser Ala Asp Ala Pro Ala Tyr Gln Gln Gly Gln
545                 550                 555                 560

Asn Gln Leu Tyr Asn Glu Leu Asn Leu Gly Arg Arg Glu Glu Tyr Asp
                565                 570                 575

Val Leu Asp Lys Arg Arg Gly Arg Asp Pro Glu Met Gly Gly Lys Pro
            580                 585                 590

Arg Arg Lys Asn Pro Gln Glu Gly Leu Tyr Asn Glu Leu Gln Lys Asp
            595                 600                 605

Lys Met Ala Glu Ala Tyr Ser Glu Ile Gly Met Lys Gly Glu Arg Arg
            610                 615                 620

Arg Gly Lys Gly His Asp Gly Leu Tyr Gln Gly Leu Ser Thr Ala Thr
625                 630                 635                 640

Lys Asp Thr Tyr Asp Ala Leu His Met Gln Ala Leu Pro Pro Arg 645        650        655

<210> SEQ ID NO 42
<211> LENGTH: 658
<212> TYPE: PRT
<213> ORGANISM: artificial sequence
<220> FEATURE:
<223> OTHER INFORMATION: description of artificial sequence: synthetic
   oligopeptide
<220> FEATURE:
<223> OTHER INFORMATION: C13F12-6 polypeptide CAR sequence

<400> SEQUENCE: 42

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Ser Gly Gly Gly Gly Ser
        115                 120                 125

Gly Gly Gly Gly Ser Asn Ile Met Leu Thr Gln Ser Pro Ser Ser Leu
    130                 135                 140

Ala Val Ser Ala Gly Glu Lys Val Thr Met Ser Cys Lys Ser Ser Gln
145                 150                 155                 160

Ser Val Phe Phe Ser Ser Ser Gln Lys Asn Tyr Leu Ala Trp Tyr Gln
                165                 170                 175

Gln Ile Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ser Glu Asp Leu Ala Ile
    210                 215                 220

Tyr Tyr Cys His Gln Tyr Leu Ser Ser Arg Thr Phe Gly Gly Gly Thr
225                 230                 235                 240

Lys Leu Glu Ile Lys Arg Glu Pro Lys Ser Pro Asp Lys Thr His Thr
                245                 250                 255

Cys Pro Pro Cys Pro Ala Pro Pro Val Ala Gly Pro Ser Val Phe Leu
            260                 265                 270

Phe Pro Pro Lys Pro Lys Asp Thr Leu Met Ile Ala Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys

```
            340                 345                 350
Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
        370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Ile Ile Ser
465                 470                 475                 480

Phe Phe Leu Ala Leu Thr Ser Thr Ala Leu Leu Phe Leu Leu Phe Phe
                485                 490                 495

Leu Thr Leu Arg Phe Ser Val Val Lys Arg Gly Arg Lys Lys Leu Leu
            500                 505                 510

Tyr Ile Phe Lys Gln Pro Phe Met Arg Pro Val Gln Thr Thr Gln Glu
        515                 520                 525

Glu Asp Gly Cys Ser Cys Arg Phe Pro Glu Glu Glu Glu Gly Gly Cys
    530                 535                 540

Glu Leu Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
                565                 570                 575

Glu Tyr Asp Val Leu Asp Lys Arg Arg Gly Arg Asp Pro Glu Met Gly
            580                 585                 590

Gly Lys Pro Arg Arg Lys Asn Pro Gln Glu Gly Leu Tyr Asn Glu Leu
        595                 600                 605

Gln Lys Asp Lys Met Ala Glu Ala Tyr Ser Glu Ile Gly Met Lys Gly
    610                 615                 620

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
                645                 650                 655

Pro Arg

<210> SEQ ID NO 43
<211> LENGTH: 49
<212> TYPE: PRT
<213> ORGANISM: Artificial sequence
<220> FEATURE:
<223> OTHER INFORMATION: description of artificial sequence: synthetic
      oligopeptide
<220> FEATURE:
<223> OTHER INFORMATION: Target TALEN TRAC_T01

<400> SEQUENCE: 43

Thr Thr Gly Thr Cys Cys Cys Ala Cys Ala Gly Ala Thr Ala Thr Cys
1               5                   10                  15

Cys Ala Gly Ala Ala Cys Cys Cys Thr Gly Ala Cys Cys Cys Thr Gly
            20                  25                  30
```

-continued

Cys Cys Gly Thr Gly Thr Ala Cys Cys Ala Gly Cys Thr Gly Ala Gly
         35                  40                  45

Ala

<210> SEQ ID NO 44
<211> LENGTH: 530
<212> TYPE: PRT
<213> ORGANISM: Artificial sequence
<220> FEATURE:
<223> OTHER INFORMATION: description of artificial sequence: synthetic
      oligopeptide
<220> FEATURE:
<223> OTHER INFORMATION: TAL binding domain  TRAC_T01-L

<400> SEQUENCE: 44

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

```
Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Gln Gln Val Val Ala Ile Ala
            370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
            435                 440                 445

Val Ala Ile Ala Ser Asn Gly Gly Gly Lys Gln Ala Leu Glu Thr Val
            450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
            485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 45
<211> LENGTH: 530
<212> TYPE: PRT
<213> ORGANISM: Artificial sequence
<220> FEATURE:
<223> OTHER INFORMATION: description of artificial sequence: synthetic
      oligopeptide
<220> FEATURE:
<223> OTHER INFORMATION: TAL binding domain TRAC_T01-R

<400> SEQUENCE: 45

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
            35                  40                  45

Gly Lys Gln Ala Leu Glu Thr Val Gln Arg Leu Leu Pro Val Leu Cys
            50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
            85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
            115                 120                 125
```

```
Pro Val Leu Cys Gln Ala His Gly Leu Thr Pro Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
530
```

| <210> SEQ ID NO 46 | |
|---|---|
| <211> LENGTH: 2814 | |
| <212> TYPE: DNA | |
| <213> ORGANISM: Artificial sequence | |
| <220> FEATURE: | |
| <223> OTHER INFORMATION: description of artificial sequence: synthetic polynucleotide | |
| <220> FEATURE: | |
| <223> OTHER INFORMATION: polynucleotide encoding TRAC_T01-L TALEN | |

<400> SEQUENCE: 46

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa caccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgacccccc agcaggtggt ggccatcgcc agcaatggcg gtggcaagca ggcgctggag | 540 |
| acggtccagc ggctgttgcc ggtgctgtgc caggcccacg gcttgacccc ccagcaggtg | 600 |
| gtggccatcg ccagcaataa tggtggcaag caggcgctgg agacggtcca gcggctgttg | 660 |
| ccggtgctgt gccaggccca cggcttgacc cccagcagg tggtggccat cgccagcaat | 720 |
| ggcggtggca agcaggcgct ggagacggtc agcggctgt tgccggtgct gtgccaggcc | 780 |
| cacggcttga ccccggagca ggtggtggcc atcgccagcc acgatggcgg caagcaggcg | 840 |
| ctggagacgg tccagcggct gttgccggtg ctgtgccagg cccacggctt gaccccggag | 900 |
| caggtggtgg ccatcgccag ccacgatggc ggcaagcagg cgctggagac ggtccagcgg | 960 |
| ctgttgccgg tgctgtgcca ggcccacggc ttgaccccgg agcaggtggt ggccatcgcc | 1020 |
| agccacgatg cggcaagca ggcgctggag acggtccagc ggctgttgcc ggtgctgtgc | 1080 |
| caggcccacg gcttgacccc ggagcaggtg gtggccatcg ccagcaatat tggtggcaag | 1140 |
| caggcgctgg agacggtgca ggcgctgttg ccggtgctgt gccaggccca cggcttgacc | 1200 |
| ccggagcagg tggtggccat cgccagccac gatggcggca agcaggcgct ggagacggtc | 1260 |
| cagcggctgt tgccggtgct gtgccaggcc cacggcttga ccccggagca ggtggtggcc | 1320 |
| atcgccagca atattggtgg caagcaggcg ctggagacgg tgcaggcgct gttgccggtg | 1380 |
| ctgtgccagg cccacggctt gaccccccag caggtggtgg ccatcgccag caataatggt | 1440 |
| ggcaagcagg cgctggagac ggtccagcgg ctgttgccgg tgctgtgcca ggcccacggc | 1500 |
| ttgaccccgg agcaggtggt ggccatcgcc agcaatattg gtggcaagca ggcgctggag | 1560 |
| acggtgcagg cgctgttgcc ggtgctgtgc caggcccacg gcttgacccc ccagcaggtg | 1620 |
| gtggccatcg ccagcaatgg cggtggcaag caggcgctgg agacggtcca gcggctgttg | 1680 |
| ccggtgctgt gccaggccca cggcttgacc ccggagcagg tggtggccat cgccagcaat | 1740 |
| attggtggca agcaggcgct ggagacggtc agcggctgt tgccggtgct gtgccaggcc | 1800 |
| cacggcttga cccccagca ggtggtggcc atcgccagca atggcggtgg caagcaggcg | 1860 |
| ctggagacgg tccagcggct gttgccggtg ctgtgccagg cccacggctt gaccccggag | 1920 |
| caggtggtgg ccatcgccag ccacgatggc ggcaagcagg cgctggagac ggtccagcgg | 1980 |
| ctgttgccgg tgctgtgcca ggcccacggc ttgaccccctc agcaggtggt ggccatcgcc | 2040 |

```
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg gccaggccga cgaaatgcag    2520
aggtacgtgg aggagaacca gaccaggaac aagcacatca accccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814

<210> SEQ ID NO 47
<211> LENGTH: 2832
<212> TYPE: DNA
<213> ORGANISM: Artificial sequence
<220> FEATURE:
<223> OTHER INFORMATION: description of artificial sequence: synthetic
      polynucleotide
<220> FEATURE:
<223> OTHER INFORMATION: polynucleotide encoding TRAC_T01-R TALEN

<400> SEQUENCE: 47
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccc tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gacccccgag caggtggtgg ccatcgccag ccacgatggc     540
ggcaagcagg cgctggagac ggtccagcgg ctgttgccgg tgctgtgcca ggcccacggc     600 ttgaccccc agcaggtggt ggccatcgcc agcaatggcg gtggcaagca ggcgctggag     660
acggtccagc ggctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc ccggagcagg tggtggccat cgccagcaat     840
attggtggca gcaggcgct ggagacggtg caggcgctgt gccggtgct gtgccaggcc      900 cacggcttga ccccccagca ggtggtggcc atcgccagca ataatggtgg caagcaggcg     960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgaccccc agcaggtggt ggccatcgcc    1140
agcaatggcg gtggcaagca ggcgctggag acggtccagc ggctgttgcc ggtgctgtgc    1200
```

```
caggcccacg gcttgacccc ccagcaggtg gtggccatcg ccagcaataa tggtggcaag    1260
caggcgctgg agacggtcca gcggctgttg ccggtgctgt gccaggccca cggcttgacc    1320
ccccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860
gatggcggca agcaggcgct ggagacggtc agcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacagggc    2400 aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760 ggcacctga ccctggagga ggtgaggagg aagttcaaca acggcgagat caacttcgcg    2820
gccgactgat aa                                                       2832
```

<210> SEQ ID NO 48  
<211> LENGTH: 461  
<212> TYPE: PRT  
<213> ORGANISM: Artificial sequence  
<220> FEATURE:  
<223> OTHER INFORMATION: BCMA-BC50 V1 polypeptide CAR sequence

<400> SEQUENCE: 48

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Ser Phe Pro Asp Tyr Tyr Ile Asn Trp Val Arg Gln Ala Pro Gly Gln
        50                  55                  60

```
Gly Leu Glu Trp Met Gly Trp Ile Tyr Phe Ala Ser Gly Asn Ser Glu
 65                  70                  75                  80

Tyr Asn Gln Lys Phe Thr Gly Arg Val Thr Met Thr Arg Asp Thr Ser
             85                   90                  95

Ile Asn Thr Ala Tyr Met Glu Leu Ser Ser Leu Thr Ser Glu Asp Thr
            100                 105                 110

Ala Val Tyr Phe Cys Ala Ser Leu Tyr Asp Tyr Asp Trp Tyr Phe Asp
        115                 120                 125

Val Trp Gly Gln Gly Thr Met Val Thr Val Ser Ser Gly Gly Gly Gly
130                 135                 140

Ser Gly Gly Gly Gly Ser Gly Gly Gly Ser Asp Ile Val Met Thr
145                 150                 155                 160

Gln Thr Pro Leu Ser Leu Ser Val Thr Pro Gly Gln Pro Ala Ser Ile
                165                 170                 175

Ser Cys Lys Ser Ser Gln Ser Leu Val His Ser Asn Gly Asn Thr Tyr
            180                 185                 190

Leu His Trp Tyr Leu Gln Lys Pro Gly Gln Ser Pro Gln Leu Leu Ile
        195                 200                 205

Tyr Lys Val Ser Asn Arg Phe Ser Gly Val Pro Asp Arg Phe Ser Gly
210                 215                 220

Ser Gly Ser Gly Thr Asp Phe Thr Leu Lys Ile Ser Arg Val Glu Ala
225                 230                 235                 240

Glu Asp Val Gly Ile Tyr Tyr Cys Ser Gln Ser Ser Ile Tyr Pro Trp
                245                 250                 255

Thr Phe Gly Gln Gly Thr Lys Leu Glu Ile Lys Gly Leu Ala Val Ser
            260                 265                 270

Thr Ile Ser Ser Phe Phe Pro Pro Gly Tyr Gln Ile Tyr Ile Trp Ala
        275                 280                 285

Pro Leu Ala Gly Thr Cys Gly Val Leu Leu Leu Ser Leu Val Ile Thr
290                 295                 300

Leu Tyr Cys Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
450                 455                 460

<210> SEQ ID NO 49
<211> LENGTH: 464
<212> TYPE: PRT
```

<213> ORGANISM: Artificial sequence
<220> FEATURE:
<223> OTHER INFORMATION: BCMA-BC50 V2 polypeptide CAR sequence

<400> SEQUENCE: 49

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Ser Phe Pro Asp Tyr Tyr Ile Asn Trp Val Arg Gln Ala Pro Gly Gln
    50                  55                  60

Gly Leu Glu Trp Met Gly Trp Ile Tyr Phe Ala Ser Gly Asn Ser Glu
65                  70                  75                  80

Tyr Asn Gln Lys Phe Thr Gly Arg Val Thr Met Thr Arg Asp Thr Ser
                85                  90                  95

Ile Asn Thr Ala Tyr Met Glu Leu Ser Ser Leu Thr Ser Glu Asp Thr
            100                 105                 110

Ala Val Tyr Phe Cys Ala Ser Leu Tyr Asp Tyr Asp Trp Tyr Phe Asp
        115                 120                 125

Val Trp Gly Gln Gly Thr Met Val Thr Val Ser Ser Gly Gly Gly Gly
    130                 135                 140

Ser Gly Gly Gly Gly Ser Gly Gly Gly Ser Asp Ile Val Met Thr
145                 150                 155                 160

Gln Thr Pro Leu Ser Leu Ser Val Thr Pro Gly Gln Pro Ala Ser Ile
                165                 170                 175

Ser Cys Lys Ser Ser Gln Ser Leu Val His Ser Asn Gly Asn Thr Tyr
            180                 185                 190

Leu His Trp Tyr Leu Gln Lys Pro Gly Gln Ser Pro Gln Leu Leu Ile
        195                 200                 205

Tyr Lys Val Ser Asn Arg Phe Ser Gly Val Pro Asp Arg Phe Ser Gly
    210                 215                 220

Ser Gly Ser Gly Thr Asp Phe Thr Leu Lys Ile Ser Arg Val Glu Ala
225                 230                 235                 240

Glu Asp Val Gly Ile Tyr Tyr Cys Ser Gln Ser Ser Ile Tyr Pro Trp
                245                 250                 255

Thr Phe Gly Gln Gly Thr Lys Leu Glu Ile Lys Gly Leu Ala Val Ser
            260                 265                 270

Thr Ile Ser Ser Phe Phe Pro Pro Gly Tyr Gln Ile Ile Ser Phe Phe
        275                 280                 285

Leu Ala Leu Thr Ser Thr Ala Leu Leu Phe Leu Leu Phe Phe Leu Thr
    290                 295                 300

Leu Arg Phe Ser Val Val Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
```

```
            385                 390                 395                 400
Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
                420                 425                 430

Arg Arg Gly Lys Gly His Asp Gly Leu Tyr Gln Gly Leu Ser Thr Ala
                435                 440                 445

Thr Lys Asp Thr Tyr Asp Ala Leu His Met Gln Ala Leu Pro Pro Arg
                450                 455                 460

<210> SEQ ID NO 50
<211> LENGTH: 490
<212> TYPE: PRT
<213> ORGANISM: Artificial sequence
<220> FEATURE:
<223> OTHER INFORMATION: BCMA-BC50 V3 polypeptide CAR sequence

<400> SEQUENCE: 50

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
                35                  40                  45

Ser Phe Pro Asp Tyr Tyr Ile Asn Trp Val Arg Gln Ala Pro Gly Gln
        50                  55                  60

Gly Leu Glu Trp Met Gly Trp Ile Tyr Phe Ala Ser Gly Asn Ser Glu
65              70                  75                  80

Tyr Asn Gln Lys Phe Thr Gly Arg Val Thr Met Thr Arg Asp Thr Ser
                85                  90                  95

Ile Asn Thr Ala Tyr Met Glu Leu Ser Ser Leu Thr Ser Glu Asp Thr
                100                 105                 110

Ala Val Tyr Phe Cys Ala Ser Leu Tyr Asp Tyr Asp Trp Tyr Phe Asp
                115                 120                 125

Val Trp Gly Gln Gly Thr Met Val Thr Val Ser Ser Gly Gly Gly Gly
        130                 135                 140

Ser Gly Gly Gly Gly Ser Gly Gly Gly Gly Ser Asp Ile Val Met Thr
145                 150                 155                 160

Gln Thr Pro Leu Ser Leu Ser Val Thr Pro Gly Gln Pro Ala Ser Ile
                165                 170                 175

Ser Cys Lys Ser Ser Gln Ser Leu Val His Ser Asn Gly Asn Thr Tyr
                180                 185                 190

Leu His Trp Tyr Leu Gln Lys Pro Gly Gln Ser Pro Gln Leu Leu Ile
        195                 200                 205

Tyr Lys Val Ser Asn Arg Phe Ser Gly Val Pro Asp Arg Phe Ser Gly
        210                 215                 220

Ser Gly Ser Gly Thr Asp Phe Thr Leu Lys Ile Ser Arg Val Glu Ala
225                 230                 235                 240

Glu Asp Val Gly Ile Tyr Tyr Cys Ser Gln Ser Ser Ile Tyr Pro Trp
                245                 250                 255

Thr Phe Gly Gln Gly Thr Lys Leu Glu Ile Lys Thr Thr Thr Pro Ala
                260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
```

```
                290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
                450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 51
<211> LENGTH: 493
<212> TYPE: PRT
<213> ORGANISM: Artificial sequence
<220> FEATURE:
<223> OTHER INFORMATION: BCMA-BC50 V4 polypeptide CAR sequence

<400> SEQUENCE: 51

Met Ala Leu Pro Val Thr Ala Leu Leu Leu Pro Leu Ala Leu Leu Leu
1                   5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Ser Phe Pro Asp Tyr Tyr Ile Asn Trp Val Arg Gln Ala Pro Gly Gln
        50                  55                  60

Gly Leu Glu Trp Met Gly Trp Ile Tyr Phe Ala Ser Gly Asn Ser Glu
65                  70                  75                  80

Tyr Asn Gln Lys Phe Thr Gly Arg Val Thr Met Thr Arg Asp Thr Ser
                85                  90                  95

Ile Asn Thr Ala Tyr Met Glu Leu Ser Ser Leu Thr Ser Glu Asp Thr
            100                 105                 110

Ala Val Tyr Phe Cys Ala Ser Leu Tyr Asp Tyr Asp Trp Tyr Phe Asp
        115                 120                 125

Val Trp Gly Gln Gly Thr Met Val Thr Val Ser Ser Gly Gly Gly Gly
    130                 135                 140

Ser Gly Gly Gly Gly Ser Gly Gly Gly Gly Ser Asp Ile Val Met Thr
145                 150                 155                 160

Gln Thr Pro Leu Ser Leu Ser Val Thr Pro Gly Gln Pro Ala Ser Ile
```

```
                165                 170                 175
Ser Cys Lys Ser Ser Gln Ser Leu Val His Ser Asn Gly Asn Thr Tyr
            180                 185                 190

Leu His Trp Tyr Leu Gln Lys Pro Gly Gln Ser Pro Gln Leu Leu Ile
            195                 200                 205

Tyr Lys Val Ser Asn Arg Phe Ser Gly Val Pro Asp Arg Phe Ser Gly
            210                 215                 220

Ser Gly Ser Gly Thr Asp Phe Thr Leu Lys Ile Ser Arg Val Glu Ala
225                 230                 235                 240

Glu Asp Val Gly Ile Tyr Tyr Cys Ser Gln Ser Ser Ile Tyr Pro Trp
                245                 250                 255

Thr Phe Gly Gln Gly Thr Lys Leu Glu Ile Lys Thr Thr Pro Ala
                260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
            290                 295                 300

Arg Gly Leu Asp Phe Ala Cys Asp Ile Ile Ser Phe Phe Leu Ala Leu
305                 310                 315                 320

Thr Ser Thr Ala Leu Leu Phe Leu Leu Phe Phe Leu Thr Leu Arg Phe
                325                 330                 335

Ser Val Val Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 52
<211> LENGTH: 676
<212> TYPE: PRT
<213> ORGANISM: Artificial sequence
<220> FEATURE:
<223> OTHER INFORMATION: BCMA-BC50 V5 polypeptide CAR sequence

<400> SEQUENCE: 52

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
```

```
            35                  40                  45
Ser Phe Pro Asp Tyr Tyr Ile Asn Trp Val Arg Gln Ala Pro Gly Gln
 50                  55                  60
Gly Leu Glu Trp Met Gly Trp Ile Tyr Phe Ala Ser Gly Asn Ser Glu
 65                  70                  75                  80
Tyr Asn Gln Lys Phe Thr Gly Arg Val Thr Met Thr Arg Asp Thr Ser
                 85                  90                  95
Ile Asn Thr Ala Tyr Met Glu Leu Ser Ser Leu Thr Ser Glu Asp Thr
                100                 105                 110
Ala Val Tyr Phe Cys Ala Ser Leu Tyr Asp Tyr Asp Trp Tyr Phe Asp
            115                 120                 125
Val Trp Gly Gln Gly Thr Met Val Thr Val Ser Ser Gly Gly Gly Gly
130                 135                 140
Ser Gly Gly Gly Gly Ser Gly Gly Gly Ser Asp Ile Val Met Thr
145                 150                 155                 160
Gln Thr Pro Leu Ser Leu Ser Val Thr Pro Gly Gln Pro Ala Ser Ile
                165                 170                 175
Ser Cys Lys Ser Ser Gln Ser Leu Val His Ser Asn Gly Asn Thr Tyr
            180                 185                 190
Leu His Trp Tyr Leu Gln Lys Pro Gly Gln Ser Pro Gln Leu Leu Ile
            195                 200                 205
Tyr Lys Val Ser Asn Arg Phe Ser Gly Val Pro Asp Arg Phe Ser Gly
210                 215                 220
Ser Gly Ser Gly Thr Asp Phe Thr Leu Lys Ile Ser Arg Val Glu Ala
225                 230                 235                 240
Glu Asp Val Gly Ile Tyr Tyr Cys Ser Gln Ser Ser Ile Tyr Pro Trp
                245                 250                 255
Thr Phe Gly Gln Gly Thr Lys Leu Glu Ile Lys Glu Pro Lys Ser Pro
            260                 265                 270
Asp Lys Thr His Thr Cys Pro Pro Cys Pro Ala Pro Pro Val Ala Gly
            275                 280                 285
Pro Ser Val Phe Leu Phe Pro Pro Lys Pro Lys Asp Thr Leu Met Ile
290                 295                 300
Ala Arg Thr Pro Glu Val Thr Cys Val Val Val Asp Val Ser His Glu
305                 310                 315                 320
Asp Pro Glu Val Lys Phe Asn Trp Tyr Val Asp Gly Val Glu Val His
                325                 330                 335
Asn Ala Lys Thr Lys Pro Arg Glu Glu Gln Tyr Asn Ser Thr Tyr Arg
            340                 345                 350
Val Val Ser Val Leu Thr Val Leu His Gln Asp Trp Leu Asn Gly Lys
            355                 360                 365
Glu Tyr Lys Cys Lys Val Ser Asn Lys Ala Leu Pro Ala Pro Ile Glu
            370                 375                 380
Lys Thr Ile Ser Lys Ala Lys Gly Gln Pro Arg Glu Pro Gln Val Tyr
385                 390                 395                 400
Thr Leu Pro Pro Ser Arg Asp Glu Leu Thr Lys Asn Gln Val Ser Leu
                405                 410                 415
Thr Cys Leu Val Lys Gly Phe Tyr Pro Ser Asp Ile Ala Val Glu Trp
            420                 425                 430
Glu Ser Asn Gly Gln Pro Glu Asn Asn Tyr Lys Thr Thr Pro Pro Val
            435                 440                 445
Leu Asp Ser Asp Gly Ser Phe Phe Leu Tyr Ser Lys Leu Thr Val Asp
            450                 455                 460
```

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Ile Tyr Ile Trp Ala Pro Leu Ala Gly Thr Cys Gly Val Leu
            500                 505                 510

Leu Leu Ser Leu Val Ile Thr Leu Tyr Cys Lys Arg Gly Arg Lys Lys
        515                 520                 525

Leu Leu Tyr Ile Phe Lys Gln Pro Phe Met Arg Pro Val Gln Thr Thr
    530                 535                 540

Gln Glu Glu Asp Gly Cys Ser Cys Arg Phe Pro Glu Glu Glu Glu Gly
545                 550                 555                 560

Gly Cys Glu Leu Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
        595                 600                 605

Met Gly Gly Lys Pro Arg Arg Lys Asn Pro Gln Glu Gly Leu Tyr Asn
    610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
                645                 650                 655

Leu Ser Thr Ala Thr Lys Asp Thr Tyr Asp Ala Leu His Met Gln Ala
            660                 665                 670

Leu Pro Pro Arg
        675

<210> SEQ ID NO 53
<211> LENGTH: 679
<212> TYPE: PRT
<213> ORGANISM: Artificial sequence
<220> FEATURE:
<223> OTHER INFORMATION: BCMA-BC50 V6 polypeptide CAR sequence

<400> SEQUENCE: 53

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Ser Phe Pro Asp Tyr Tyr Ile Asn Trp Val Arg Gln Ala Pro Gly Gln
    50                  55                  60

Gly Leu Glu Trp Met Gly Trp Ile Tyr Phe Ala Ser Gly Asn Ser Glu
65                  70                  75                  80

Tyr Asn Gln Lys Phe Thr Gly Arg Val Thr Met Thr Arg Asp Thr Ser
                85                  90                  95

Ile Asn Thr Ala Tyr Met Glu Leu Ser Ser Leu Thr Ser Glu Asp Thr
            100                 105                 110

Ala Val Tyr Phe Cys Ala Ser Leu Tyr Asp Tyr Asp Trp Tyr Phe Asp
        115                 120                 125

Val Trp Gly Gln Gly Thr Met Val Thr Val Ser Ser Gly Gly Gly Gly
    130                 135                 140

```
Ser Gly Gly Gly Gly Ser Gly Gly Gly Ser Asp Ile Val Met Thr
145                 150                 155                 160

Gln Thr Pro Leu Ser Leu Ser Val Thr Pro Gly Gln Pro Ala Ser Ile
                165                 170                 175

Ser Cys Lys Ser Ser Gln Ser Leu Val His Ser Asn Gly Asn Thr Tyr
            180                 185                 190

Leu His Trp Tyr Leu Gln Lys Pro Gly Gln Ser Pro Gln Leu Leu Ile
        195                 200                 205

Tyr Lys Val Ser Asn Arg Phe Ser Gly Val Pro Asp Arg Phe Ser Gly
    210                 215                 220

Ser Gly Ser Gly Thr Asp Phe Thr Leu Lys Ile Ser Arg Val Glu Ala
225                 230                 235                 240

Glu Asp Val Gly Ile Tyr Tyr Cys Ser Gln Ser Ser Ile Tyr Pro Trp
                245                 250                 255

Thr Phe Gly Gln Gly Thr Lys Leu Glu Ile Lys Glu Pro Lys Ser Pro
            260                 265                 270

Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ala Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Ile Ile Ser Phe Phe Leu Ala Leu Thr Ser Thr Ala Leu Leu
            500                 505                 510

Phe Leu Leu Phe Phe Leu Thr Leu Arg Phe Ser Val Val Lys Arg Gly
        515                 520                 525

Arg Lys Lys Leu Leu Tyr Ile Phe Lys Gln Pro Phe Met Arg Pro Val
    530                 535                 540

Gln Thr Thr Gln Glu Glu Asp Gly Cys Ser Cys Arg Phe Pro Glu Glu
545                 550                 555                 560
```

```
Glu Glu Gly Gly Cys Glu Leu Arg Val Lys Phe Ser Arg Ser Ala Asp
            565                 570                 575

Ala Pro Ala Tyr Gln Gln Gly Gln Asn Gln Leu Tyr Asn Glu Leu Asn
        580                 585                 590

Leu Gly Arg Arg Glu Glu Tyr Asp Val Leu Asp Lys Arg Arg Gly Arg
        595                 600                 605

Asp Pro Glu Met Gly Gly Lys Pro Arg Arg Lys Asn Pro Gln Glu Gly
        610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
                660                 665                 670

Met Gln Ala Leu Pro Pro Arg
            675

<210> SEQ ID NO 54
<211> LENGTH: 461
<212> TYPE: PRT
<213> ORGANISM: Artificial sequence
<220> FEATURE:
<223> OTHER INFORMATION: BCMA-BC30 V1 polypeptide CAR sequence

<400> SEQUENCE: 54

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Ser Phe Pro Asp Tyr Tyr Ile Asn Trp Val Arg Gln Ala Pro Gly Gln
    50                  55                  60

Gly Leu Glu Trp Met Gly Trp Ile Tyr Phe Ala Ser Gly Asn Ser Glu
65                  70                  75                  80

Tyr Asn Gln Lys Phe Thr Gly Arg Val Thr Met Thr Arg Asp Thr Ser
                85                  90                  95

Ser Ser Thr Ala Tyr Met Glu Leu Ser Ser Leu Arg Ser Glu Asp Thr
            100                 105                 110

Ala Val Tyr Phe Cys Ala Ser Leu Tyr Asp Tyr Asp Trp Tyr Phe Asp
        115                 120                 125

Val Trp Gly Gln Gly Thr Met Val Thr Val Ser Ser Gly Gly Gly Gly
    130                 135                 140

Ser Gly Gly Gly Gly Ser Gly Gly Gly Ser Asp Ile Val Met Thr
145                 150                 155                 160

Gln Thr Pro Leu Ser Leu Ser Val Thr Pro Gly Glu Pro Ala Ser Ile
                165                 170                 175

Ser Cys Lys Ser Ser Gln Ser Leu Val His Ser Asn Gly Asn Thr Tyr
            180                 185                 190

Leu His Trp Tyr Leu Gln Lys Pro Gly Gln Ser Pro Gln Leu Leu Ile
        195                 200                 205

Tyr Lys Val Ser Asn Arg Phe Ser Gly Val Pro Asp Arg Phe Ser Gly
    210                 215                 220

Ser Gly Ser Gly Ala Asp Phe Thr Leu Lys Ile Ser Arg Val Glu Ala
225                 230                 235                 240
```

```
Glu Asp Val Gly Val Tyr Tyr Cys Ala Glu Thr Ser His Val Pro Trp
            245                 250                 255

Thr Phe Gly Gln Gly Thr Lys Leu Glu Ile Lys Gly Leu Ala Val Ser
        260                 265                 270

Thr Ile Ser Ser Phe Phe Pro Pro Gly Tyr Gln Ile Tyr Ile Trp Ala
        275                 280                 285

Pro Leu Ala Gly Thr Cys Gly Val Leu Leu Leu Ser Leu Val Ile Thr
        290                 295                 300

Leu Tyr Cys Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
                340                 345                 350

Phe Ser Arg Ser Ala Asp Ala Pro Ala Tyr Gln Gln Gly Gln Asn Gln
            355                 360                 365

Leu Tyr Asn Glu Leu Asn Leu Gly Arg Arg Glu Glu Tyr Asp Val Leu
370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
450                 455                 460

<210> SEQ ID NO 55
<211> LENGTH: 464
<212> TYPE: PRT
<213> ORGANISM: Artificial sequence
<220> FEATURE:
<223> OTHER INFORMATION: BCMA-BC30 V2 polypeptide CAR sequence

<400> SEQUENCE: 55

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Ser Phe Pro Asp Tyr Tyr Ile Asn Trp Val Arg Gln Ala Pro Gly Gln
        50                  55                  60

Gly Leu Glu Trp Met Gly Trp Ile Tyr Phe Ala Ser Gly Asn Ser Glu
65                  70                  75                  80

Tyr Asn Gln Lys Phe Thr Gly Arg Val Thr Met Thr Arg Asp Thr Ser
                85                  90                  95

Ser Ser Thr Ala Tyr Met Glu Leu Ser Ser Leu Arg Ser Glu Asp Thr
            100                 105                 110

Ala Val Tyr Phe Cys Ala Ser Leu Tyr Asp Tyr Asp Trp Tyr Phe Asp
        115                 120                 125

Val Trp Gly Gln Gly Thr Met Val Thr Val Ser Ser Gly Gly Gly Gly
        130                 135                 140
```

```
Ser Gly Gly Gly Gly Ser Gly Gly Gly Ser Asp Ile Val Met Thr
145                 150                 155                 160

Gln Thr Pro Leu Ser Leu Ser Val Thr Pro Gly Glu Pro Ala Ser Ile
                165                 170                 175

Ser Cys Lys Ser Ser Gln Ser Leu Val His Ser Asn Gly Asn Thr Tyr
            180                 185                 190

Leu His Trp Tyr Leu Gln Lys Pro Gly Gln Ser Pro Gln Leu Leu Ile
        195                 200                 205

Tyr Lys Val Ser Asn Arg Phe Ser Gly Val Pro Asp Arg Phe Ser Gly
    210                 215                 220

Ser Gly Ser Gly Ala Asp Phe Thr Leu Lys Ile Ser Arg Val Glu Ala
225                 230                 235                 240

Glu Asp Val Gly Val Tyr Tyr Cys Ala Glu Thr Ser His Val Pro Trp
                245                 250                 255

Thr Phe Gly Gln Gly Thr Lys Leu Glu Ile Lys Gly Leu Ala Val Ser
                260                 265                 270

Thr Ile Ser Ser Phe Phe Pro Pro Gly Tyr Gln Ile Ile Ser Phe Phe
            275                 280                 285

Leu Ala Leu Thr Ser Thr Ala Leu Leu Phe Leu Leu Phe Phe Leu Thr
        290                 295                 300

Leu Arg Phe Ser Val Val Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460

<210> SEQ ID NO 56
<211> LENGTH: 490
<212> TYPE: PRT
<213> ORGANISM: Artificial sequence
<220> FEATURE:
<223> OTHER INFORMATION: BCMA-BC30 V3 polypeptide CAR sequence

<400> SEQUENCE: 56

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45
```

```
Ser Phe Pro Asp Tyr Tyr Ile Asn Trp Val Arg Gln Ala Pro Gly Gln
    50                  55                  60

Gly Leu Glu Trp Met Gly Trp Ile Tyr Phe Ala Ser Gly Asn Ser Glu
 65              70                  75                  80

Tyr Asn Gln Lys Phe Thr Gly Arg Val Thr Met Thr Arg Asp Thr Ser
                 85                  90                  95

Ser Ser Thr Ala Tyr Met Glu Leu Ser Ser Leu Arg Ser Glu Asp Thr
            100                 105                 110

Ala Val Tyr Phe Cys Ala Ser Leu Tyr Asp Tyr Asp Trp Tyr Phe Asp
            115                 120                 125

Val Trp Gly Gln Gly Thr Met Val Thr Val Ser Ser Gly Gly Gly Gly
    130                 135                 140

Ser Gly Gly Gly Gly Ser Gly Gly Gly Ser Asp Ile Val Met Thr
145                 150                 155                 160

Gln Thr Pro Leu Ser Leu Ser Val Thr Pro Gly Glu Pro Ala Ser Ile
                165                 170                 175

Ser Cys Lys Ser Ser Gln Ser Leu Val His Ser Asn Gly Asn Thr Tyr
            180                 185                 190

Leu His Trp Tyr Leu Gln Lys Pro Gly Gln Ser Pro Gln Leu Leu Ile
    195                 200                 205

Tyr Lys Val Ser Asn Arg Phe Ser Gly Val Pro Asp Arg Phe Ser Gly
    210                 215                 220

Ser Gly Ser Gly Ala Asp Phe Thr Leu Lys Ile Ser Arg Val Glu Ala
225                 230                 235                 240

Glu Asp Val Gly Val Tyr Tyr Cys Ala Glu Thr Ser His Val Pro Trp
            245                 250                 255

Thr Phe Gly Gln Gly Thr Lys Leu Glu Ile Lys Thr Thr Pro Ala
                260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
            325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Gly Lys Gly His
    450                 455                 460

Asp Gly Leu Tyr Gln Gly Leu Ser Thr Ala Thr Lys Asp Thr Tyr Asp
```

Ala Leu His Met Gln Ala Leu Pro Pro Arg
            485                 490

<210> SEQ ID NO 57
<211> LENGTH: 493
<212> TYPE: PRT
<213> ORGANISM: Artificial sequence
<220> FEATURE:
<223> OTHER INFORMATION: BCMA-BC30 V4 polypeptide CAR sequence

<400> SEQUENCE: 57

Met Ala Leu Pro Val Thr Ala Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
            35                  40                  45

Ser Phe Pro Asp Tyr Tyr Ile Asn Trp Val Arg Gln Ala Pro Gly Gln
    50                  55                  60

Gly Leu Glu Trp Met Gly Trp Ile Tyr Phe Ala Ser Gly Asn Ser Glu
65                  70                  75                  80

Tyr Asn Gln Lys Phe Thr Gly Arg Val Thr Met Thr Arg Asp Thr Ser
                85                  90                  95

Ser Ser Thr Ala Tyr Met Glu Leu Ser Ser Leu Arg Ser Glu Asp Thr
            100                 105                 110

Ala Val Tyr Phe Cys Ala Ser Leu Tyr Asp Tyr Asp Trp Tyr Phe Asp
            115                 120                 125

Val Trp Gly Gln Gly Thr Met Val Thr Val Ser Ser Gly Gly Gly Gly
    130                 135                 140

Ser Gly Gly Gly Gly Ser Gly Gly Gly Ser Asp Ile Val Met Thr
145                 150                 155                 160

Gln Thr Pro Leu Ser Leu Ser Val Thr Pro Gly Glu Pro Ala Ser Ile
                165                 170                 175

Ser Cys Lys Ser Ser Gln Ser Leu Val His Ser Asn Gly Asn Thr Tyr
            180                 185                 190

Leu His Trp Tyr Leu Gln Lys Pro Gly Gln Ser Pro Gln Leu Leu Ile
            195                 200                 205

Tyr Lys Val Ser Asn Arg Phe Ser Gly Val Pro Asp Arg Phe Ser Gly
        210                 215                 220

Ser Gly Ser Gly Ala Asp Phe Thr Leu Lys Ile Ser Arg Val Glu Ala
225                 230                 235                 240

Glu Asp Val Gly Val Tyr Tyr Cys Ala Glu Thr Ser His Val Pro Trp
                245                 250                 255

Thr Phe Gly Gln Gly Thr Lys Leu Glu Ile Lys Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Ile Ser Phe Phe Leu Ala Leu
305                 310                 315                 320

Thr Ser Thr Ala Leu Leu Phe Leu Leu Phe Phe Leu Thr Leu Arg Phe
                325                 330                 335

Ser Val Val Lys Arg Gly Arg Lys Lys Leu Leu Tyr Ile Phe Lys Gln

```
            340                 345                 350
Pro Phe Met Arg Pro Val Gln Thr Thr Gln Glu Glu Asp Gly Cys Ser
            355                 360                 365
Cys Arg Phe Pro Glu Glu Glu Gly Gly Cys Glu Leu Arg Val Lys
370                 375                 380
Phe Ser Arg Ser Ala Asp Ala Pro Ala Tyr Gln Gln Gly Gln Asn Gln
385                 390                 395                 400
Leu Tyr Asn Glu Leu Asn Leu Gly Arg Arg Glu Glu Tyr Asp Val Leu
                405                 410                 415
Asp Lys Arg Arg Gly Arg Asp Pro Glu Met Gly Gly Lys Pro Arg Arg
                420                 425                 430
Lys Asn Pro Gln Glu Gly Leu Tyr Asn Glu Leu Gln Lys Asp Lys Met
                435                 440                 445
Ala Glu Ala Tyr Ser Glu Ile Gly Met Lys Gly Glu Arg Arg Arg Gly
                450                 455                 460
Lys Gly His Asp Gly Leu Tyr Gln Gly Leu Ser Thr Ala Thr Lys Asp
465                 470                 475                 480
Thr Tyr Asp Ala Leu His Met Gln Ala Leu Pro Pro Arg
                485                 490

<210> SEQ ID NO 58
<211> LENGTH: 676
<212> TYPE: PRT
<213> ORGANISM: Artificial sequence
<220> FEATURE:
<223> OTHER INFORMATION: BCMA-BC30 V5 polypeptide CAR sequence

<400> SEQUENCE: 58

Met Ala Leu Pro Val Thr Ala Leu Leu Leu Pro Leu Ala Leu Leu Leu
1               5                   10                  15
His Ala Ala Arg Pro Gln Val Gln Leu Val Gln Ser Gly Ala Glu Val
                20                  25                  30
Lys Lys Pro Gly Ala Ser Val Lys Val Ser Cys Lys Ala Ser Gly Tyr
            35                  40                  45
Ser Phe Pro Asp Tyr Tyr Ile Asn Trp Val Arg Gln Ala Pro Gly Gln
        50                  55                  60
Gly Leu Glu Trp Met Gly Trp Ile Tyr Phe Ala Ser Gly Asn Ser Glu
65                  70                  75                  80
Tyr Asn Gln Lys Phe Thr Gly Arg Val Thr Met Thr Arg Asp Thr Ser
                85                  90                  95
Ser Ser Thr Ala Tyr Met Glu Leu Ser Ser Leu Arg Ser Glu Asp Thr
                100                 105                 110
Ala Val Tyr Phe Cys Ala Ser Leu Tyr Asp Tyr Asp Trp Tyr Phe Asp
            115                 120                 125
Val Trp Gly Gln Gly Thr Met Val Thr Val Ser Ser Gly Gly Gly Gly
        130                 135                 140
Ser Gly Gly Gly Gly Ser Gly Gly Gly Gly Ser Asp Ile Val Met Thr
145                 150                 155                 160
Gln Thr Pro Leu Ser Leu Ser Val Thr Pro Gly Glu Pro Ala Ser Ile
                165                 170                 175
Ser Cys Lys Ser Ser Gln Ser Leu Val His Ser Asn Gly Asn Thr Tyr
                180                 185                 190
Leu His Trp Tyr Leu Gln Lys Pro Gly Gln Ser Pro Gln Leu Leu Ile
            195                 200                 205
Tyr Lys Val Ser Asn Arg Phe Ser Gly Val Pro Asp Arg Phe Ser Gly
```

```
            210                 215                 220
Ser Gly Ser Gly Ala Asp Phe Thr Leu Lys Ile Ser Arg Val Glu Ala
225                 230                 235                 240

Glu Asp Val Gly Val Tyr Tyr Cys Ala Glu Thr Ser His Val Pro Trp
                245                 250                 255

Thr Phe Gly Gln Gly Thr Lys Leu Glu Ile Lys Glu Pro Lys Ser Pro
                260                 265                 270

Asp Lys Thr His Thr Cys Pro Pro Cys Pro Ala Pro Pro Val Ala Gly
                275                 280                 285

Pro Ser Val Phe Leu Phe Pro Pro Lys Pro Lys Asp Thr Leu Met Ile
        290                 295                 300

Ala Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
                340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
        370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415

Thr Cys Leu Val Lys Gly Phe Tyr Pro Ser Asp Ile Ala Val Glu Trp
                420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
        450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Ile Tyr Ile Trp Ala Pro Leu Ala Gly Thr Cys Gly Val Leu
                500                 505                 510

Leu Leu Ser Leu Val Ile Thr Leu Tyr Cys Lys Arg Gly Arg Lys Lys
        515                 520                 525

Leu Leu Tyr Ile Phe Lys Gln Pro Phe Met Arg Pro Val Gln Thr Thr
        530                 535                 540

Gln Glu Glu Asp Gly Cys Ser Cys Arg Phe Pro Glu Glu Glu Glu Gly
545                 550                 555                 560

Gly Cys Glu Leu Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
                580                 585                 590

Arg Glu Glu Tyr Asp Val Leu Asp Lys Arg Arg Gly Arg Asp Pro Glu
        595                 600                 605

Met Gly Gly Lys Pro Arg Arg Lys Asn Pro Gln Glu Gly Leu Tyr Asn
        610                 615                 620

Glu Leu Gln Lys Asp Lys Met Ala Glu Ala Tyr Ser Glu Ile Gly Met
625                 630                 635                 640
```

```
Lys Gly Glu Arg Arg Arg Gly Lys Gly His Asp Gly Leu Tyr Gln Gly
                    645                 650                 655

Leu Ser Thr Ala Thr Lys Asp Thr Tyr Asp Ala Leu His Met Gln Ala
                660                 665                 670

Leu Pro Pro Arg
        675

<210> SEQ ID NO 59
<211> LENGTH: 679
<212> TYPE: PRT
<213> ORGANISM: Artificial sequence
<220> FEATURE:
<223> OTHER INFORMATION: BCMA-BC30 V6 polypeptide CAR sequence

<400> SEQUENCE: 59

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Ser Phe Pro Asp Tyr Tyr Ile Asn Trp Val Arg Gln Ala Pro Gly Gln
        50                  55                  60

Gly Leu Glu Trp Met Gly Trp Ile Tyr Phe Ala Ser Gly Asn Ser Glu
65                  70                  75                  80

Tyr Asn Gln Lys Phe Thr Gly Arg Val Thr Met Thr Arg Asp Thr Ser
                85                  90                  95

Ser Ser Thr Ala Tyr Met Glu Leu Ser Ser Leu Arg Ser Glu Asp Thr
                100                 105                 110

Ala Val Tyr Phe Cys Ala Ser Leu Tyr Asp Tyr Asp Trp Tyr Phe Asp
            115                 120                 125

Val Trp Gly Gln Gly Thr Met Val Thr Val Ser Ser Gly Gly Gly Gly
        130                 135                 140

Ser Gly Gly Gly Gly Ser Gly Gly Gly Gly Ser Asp Ile Val Met Thr
145                 150                 155                 160

Gln Thr Pro Leu Ser Leu Ser Val Thr Pro Gly Glu Pro Ala Ser Ile
                165                 170                 175

Ser Cys Lys Ser Ser Gln Ser Leu Val His Ser Asn Gly Asn Thr Tyr
            180                 185                 190

Leu His Trp Tyr Leu Gln Lys Pro Gly Gln Ser Pro Gln Leu Leu Ile
        195                 200                 205

Tyr Lys Val Ser Asn Arg Phe Ser Gly Val Pro Asp Arg Phe Ser Gly
    210                 215                 220

Ser Gly Ser Gly Ala Asp Phe Thr Leu Lys Ile Ser Arg Val Glu Ala
225                 230                 235                 240

Glu Asp Val Gly Val Tyr Tyr Cys Ala Glu Thr Ser His Val Pro Trp
                245                 250                 255

Thr Phe Gly Gln Gly Thr Lys Leu Glu Ile Lys Glu Pro Lys Ser Pro
            260                 265                 270

Asp Lys Thr His Thr Cys Pro Pro Cys Pro Ala Pro Val Ala Gly
        275                 280                 285

Pro Ser Val Phe Leu Phe Pro Pro Lys Pro Lys Asp Thr Leu Met Ile
    290                 295                 300

Ala Arg Thr Pro Glu Val Thr Cys Val Val Val Asp Val Ser His Glu
305                 310                 315                 320
```

Asp Pro Glu Val Lys Phe Asn Trp Tyr Val Asp Gly Val Glu Val His
            325                 330                 335

Asn Ala Lys Thr Lys Pro Arg Glu Glu Gln Tyr Asn Ser Thr Tyr Arg
        340                 345                 350

Val Val Ser Val Leu Thr Val Leu His Gln Asp Trp Leu Asn Gly Lys
    355                 360                 365

Glu Tyr Lys Cys Lys Val Ser Asn Lys Ala Leu Pro Ala Pro Ile Glu
370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Ile Ile Ser Phe Phe Leu Ala Leu Thr Ser Thr Ala Leu Leu
            500                 505                 510

Phe Leu Leu Phe Phe Leu Thr Leu Arg Phe Ser Val Val Lys Arg Gly
        515                 520                 525

Arg Lys Lys Leu Leu Tyr Ile Phe Lys Gln Pro Phe Met Arg Pro Val
    530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Arg Val Lys Phe Ser Arg Ser Ala Asp
                565                 570                 575

Ala Pro Ala Tyr Gln Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
        595                 600                 605

Asp Pro Glu Met Gly Gly Lys Pro Arg Arg Lys Asn Pro Gln Glu Gly
    610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
            660                 665                 670

Met Gln Ala Leu Pro Pro Arg
            675

<210> SEQ ID NO 60
<211> LENGTH: 135
<212> TYPE: PRT
<213> ORGANISM: Artificial sequence
<220> FEATURE:
<223> OTHER INFORMATION: Suicide RQR8

<400> SEQUENCE: 60

```
Cys Pro Tyr Ser Asn Pro Ser Leu Cys Ser Gly Gly Gly Ser Glu
1               5                   10                  15

Leu Pro Thr Gln Gly Thr Phe Ser Asn Val Ser Thr Asn Val Ser Pro
                20                  25                  30

Ala Lys Pro Thr Thr Thr Ala Cys Pro Tyr Ser Asn Pro Ser Leu Cys
        35                  40                  45

Ser Gly Gly Gly Ser Pro Ala Pro Arg Pro Thr Pro Ala Pro
    50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
                100                 105                 110

Ser Leu Val Ile Thr Leu Tyr Cys Asn His Arg Asn Arg Arg Val
        115                 120                 125

Cys Lys Cys Pro Arg Pro Trp
    130                 135
```

<210> SEQ ID NO 61
<211> LENGTH: 5
<212> TYPE: PRT
<213> ORGANISM: Artificial sequence
<220> FEATURE:
<223> OTHER INFORMATION: CDR1 VH

<400> SEQUENCE: 61

```
Asp Tyr Tyr Ile Asn
1               5
```

<210> SEQ ID NO 62
<211> LENGTH: 17
<212> TYPE: PRT
<213> ORGANISM: Artificial sequence
<220> FEATURE:
<223> OTHER INFORMATION: CDR2 VH

<400> SEQUENCE: 62

```
Trp Ile Tyr Phe Ala Ser Gly Asn Ser Glu Tyr Asn Gln Lys Phe Thr
1               5                   10                  15

Gly
```

<210> SEQ ID NO 63
<211> LENGTH: 10
<212> TYPE: PRT
<213> ORGANISM: Artificial sequence
<220> FEATURE:
<223> OTHER INFORMATION: CDR3 VH

<400> SEQUENCE: 63

```
Leu Tyr Asp Tyr Asp Trp Tyr Phe Asp Val
1               5                   10
```

<210> SEQ ID NO 64
<211> LENGTH: 16
<212> TYPE: PRT
<213> ORGANISM: Artificial sequence
<220> FEATURE:
<223> OTHER INFORMATION: CDR1 VL

<400> SEQUENCE: 64

Lys Ser Ser Gln Ser Leu Val His Ser Asn Gly Asn Thr Tyr Leu His
1               5                   10                  15

<210> SEQ ID NO 65
<211> LENGTH: 7
<212> TYPE: PRT
<213> ORGANISM: Artificial sequence
<220> FEATURE:
<223> OTHER INFORMATION: CDR2 VL

<400> SEQUENCE: 65

Lys Val Ser Asn Arg Phe Ser
1               5

<210> SEQ ID NO 66
<211> LENGTH: 9
<212> TYPE: PRT
<213> ORGANISM: Artificial sequence
<220> FEATURE:
<223> OTHER INFORMATION: CDR3 VL-1

<400> SEQUENCE: 66

Ala Glu Thr Ser His Val Pro Trp Thr
1               5

<210> SEQ ID NO 67
<211> LENGTH: 9
<212> TYPE: PRT
<213> ORGANISM: Artificial sequence
<220> FEATURE:
<223> OTHER INFORMATION: CDR3 VL-2

<400> SEQUENCE: 67

Ser Gln Ser Ser Ile Tyr Pro Trp Thr
1               5

<210> SEQ ID NO 68
<211> LENGTH: 119
<212> TYPE: PRT
<213> ORGANISM: Artificial sequence
<220> FEATURE:
<223> OTHER INFORMATION: VH
<220> FEATURE:
<221> NAME/KEY: VARIANT
<222> LOCATION: 1-30, 36-49, 67-98, 109-119
<223> OTHER INFORMATION: Xaa denotes any amino acid residue

<400> SEQUENCE: 68

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Asp Tyr
            20                  25                  30

Tyr Ile Asn Xaa Xaa Xaa Xaa Xaa Xaa Xaa Xaa Xaa Xaa Xaa Xaa Xaa
            35                  40                  45

Xaa Trp Ile Tyr Phe Ala Ser Gly Asn Ser Glu Tyr Asn Gln Lys Phe
    50                  55                  60

Thr Gly Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Leu Tyr Asp Tyr Asp Trp Tyr Phe Asp Val Xaa Xaa Xaa Xaa
            100                 105                 110

Xaa Xaa Xaa Xaa Xaa Xaa Xaa
            115

```
<210> SEQ ID NO 69
<211> LENGTH: 112
<212> TYPE: PRT
<213> ORGANISM: Artificial sequence
<220> FEATURE:
<223> OTHER INFORMATION: VL
<220> FEATURE:
<221> NAME/KEY: VARIANT
<222> LOCATION: 1-23, 40-54, 62-93, 103-112
<223> OTHER INFORMATION: Xaa denotes any amino acid residue

<400> SEQUENCE: 69

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Lys Ser Ser Gln Ser Leu Val His Ser
            20                  25                  30

Asn Gly Asn Thr Tyr Leu His Xaa Xaa Xaa Xaa Xaa Xaa Xaa Xaa Xaa
        35                  40                  45

Xaa Xaa Xaa Xaa Xaa Xaa Lys Val Ser Asn Arg Phe Ser Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Ser Gln Ser
                85                  90                  95

Ser Ile Tyr Pro Trp Thr Xaa Xaa Xaa Xaa Xaa Xaa Xaa Xaa Xaa Xaa
            100                 105                 110
```

BCMA (CD269) SPECIFIC CHIMERIC ANTIGEN RECEPTORS FOR CANCER IMMUNOTHERAPY

CROSS REFERENCE TO RELATED APPLICATION

This application is a 35 U.S.C. 371 National Phase of PCT Application No. PCT/EP2015/057995 filed Apr. 13, 2015, which claims priority to Danish Patent Application No. PA201470212, filed Apr. 14, 2014. The disclosure of these prior applications are hereby incorporated in their entirety by reference.

FIELD OF THE INVENTION

The present invention relates to Chimeric Antigen Receptors (CAR) that are recombinant chimeric proteins able to redirect immune cell specificity and reactivity toward BCMA, a cell surface glycoprotein found on most myeloid cells and used to diagnose acute myeloid Leukemia (AML) in patients. The CARs according to the invention are particularly useful to treat malignant cells bearing BCMA antigen, when expressed in T-cells or NK cells. The resulting engineered immune cells display high level of specificity toward malignant cells, conferring safety and efficiency for immunotherapy.

The invention provides a chimeric antigen receptor (CAR) that specifically binds to BCMA (e.g., human BCMA) (CAR, BCMA CAR or anti-BCMA CAR) and an immune cell comprising said CAR, preferably T cells and more preferably a BCMA CAR T cells wherein the expression of a TCR is inhibited and/or which is resistant to at least one drug, even more preferably further comprising a suicide gene. The invention also provides polynucleotides encoding said CAR, compositions comprising said CAR-T cells and methods of making and using said CAR and CAR-T cells. The invention provides said CAR as a medicament, a method for treating a pathological condition associated with BCMA expression in a subject, such as cancer.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T-cell cytotoxicity. However, they failed to provide prolonged expansion and anti-tumor activity in vivo. Signaling domains from co-stimulatory molecules, as well as transmembrane and hinge domains have been added to form CARs of second and third generations, leading to some successful therapeutic trials in humans, where T-cells could be redirected against malignant cells expressing CD19 (June et al., 2011). However, the particular combination of signaling domains, transmembrane and co-stimulatory domains used with respect to CD19 ScFv, was rather antigen-specific and cannot be expanded to any antigen markers.

Multiple myeloma is a malignancy characterized by an accumulation of clonal plasma cells. Current therapies for multiple myeloma often cause remissions, but nearly all patients eventually relapse and die (Lionel S., et al. 2011). There is substantial evidence of an immune-mediated elimination of myeloma cells in the setting of allogeneic hematopoietic stem cell transplantation; however, the toxicity of this approach is high, and few patients are cured. Although some monoclonal antibodies have shown promise for treating multiple myeloma in preclinical studies and early clinical trials, consistent clinical efficacy of any monoclonal antibody therapy for multiple myeloma has not been conclusively shown (Van De Donk, N. W. C J., et al., 2012). Moreover, some monoclonal antibodies induce side effects such as hypercytokinemia, a well-known toxicity stemming from the large release of cytokines from activated immune cells. This may be observed during therapy with immune cells expressing CARs.

There is clearly a great need for new immunotherapies for multiple myeloma, and developing an effective and safe antigen-specific adoptive T-cell therapy for this disease would be a major advance In particular, developing an effective antigen-specific adoptive T-cell therapy for such diseases inducing no or moderate hypercytokinemia would be of interest.

One candidate antigen of immunotherapies for multiple myeloma is B-cell maturation antigen (BCMA) also referred as CD269 (SwissProt/Uniprot reference Q02223). This antigen is encoded by the gene TNFRSF17. BCMA RNA was detected universally in multiple myeloma cells, and BCMA protein was detected on the surface of plasma cells from patients with multiple myeloma by several investigators (Novak A. J. et al., 2004). BCMA is a member of the TNF receptor superfamily. BCMA binds B-cell activating factor (BAFF) and a proliferation-inducing ligand (APRIL). Among nonmalignant cells, BCMA has been reported to be expressed mostly by plasma cells and subsets of mature B cells, but not by T cells and NK cells. It thus represents an appropriate target antigen for treating multiple myeloma, especially using CAR-expressing T cells.

As an alternative to the previous strategies, WO 2013/154760 proposed a BCMA CAR derived from C11 D5.3 and from C12A3.2.

As improved strategies, the present invention provides with BCMA specific CARs, which can be expressed in immune cells to target BCMA malignant cells with significant clinical advantage. In particular, the present invention provides a BCMA specific CAR, which can be expressed at the surface of immune cells, binds to BCMA and exhibit an activity towards BCMA expressing cells, in particular against BCMA expressing cancer cells, preferably said activity is a cytolytic activity against target BCMA expressing cancer cells and more preferably a cytolytic activity against target BCMA expressing cancer cells and a moderate (50% decrease) to low (70% or more decrease) expression of cytokine There is a need to provide BCMA CARs T cells well tolerated by hosts and having the capacity to survive in the presence of drugs and target selectively BCMA expressing cells, in particular in the presence of drugs used to treat cancer, in particular cytotoxic chemotherapy agents affecting cell survival (anti-cancer chemotherapy).

Several cytotoxic agents such as anti-metabolites, alkylating agents, anthracyclines, DNA methyltransferase inhibitors, platinum compounds and spindle poisons have been developed to kill cancer cells, in particular cancer cells expressing BCMA.

These chemotherapy agents can be detrimental to the establishment of robust anti-tumor immunocompetent cells due to their non-specific toxicity. Small molecule-based therapies targeting cell proliferation pathways may also hamper the establishment of anti-tumor immunity.

Thus, there is also a need of developing well tolerated T cells targeting BCMA that would be specific and compatible with the use of drugs, in particular of anti-cancer chemotherapies, such as those affecting cell proliferation.

Thus, to use "off-the-shelf" allogeneic therapeutic cells in conjunction with chemotherapy, the inventors develop a method of engineering BCMA expressing CAR T cells that are less allogeneic, in particular cells that are less allogenic and resistant to chemotherapeutic agents and can be optionally destroyed thanks to a suicide gene.

The therapeutic benefits afforded by this strategy should be enhanced by the synergistic effects between chemotherapy and immunotherapy. Moreover, drug resistance can also benefit from the ability to selectively expand the engineered T-cell thereby avoiding the problems due to inefficient gene transfer to these cells.

SUMMARY OF THE INVENTION

The inventors have generated BCMA specific CARs having different structure and comprising different scFV derived from different BCMA specific antibodies.

The present invention provides a BCMA (CD269) specific chimeric antigen receptor (CAR) having at least 80% identity with one of the polypeptide structure selected from V1 to V6, preferably having a polypeptide structure selected from V1, V3 or V5, said structure comprising:
(a) an extra cellular ligand binding-domain comprising VH and VL from a monoclonal anti-BCMA antibody,
(b) a hinge selected from a FcRIIIα, hinge, a CD8α hinge and an IgG1 hinge,
(c) a CD8α transmembrane domain and
(d) a cytoplasmic domain including a CD3 zeta signaling domain and a co-stimulatory domain from 4-1BB.

In a preferred embodiment the present invention provides the present invention provides a BCMA (CD269) specific chimeric antigen receptor (CAR) having at least 80% identity with one of the polypeptide structure selected from V1, V3 or V5, said structure comprising:
(a) an extra cellular ligand binding-domain comprising VH and VL from a monoclonal anti-BCMA antibody,
(b) a hinge selected from a FcRIIIα, hinge, a CD8α hinge and an IgG1 hinge,
(c) a CD8α transmembrane domain and
(d) a cytoplasmic domain including a CD3 zeta signaling domain and a co-stimulatory domain from 4-1BB.

In one embodiment the present invention provides a BCMA (CD269) specific chimeric antigen receptor (CAR) as above, said polypeptide structure comprising an extra cellular ligand binding-domain comprising a VH and a VL from a monoclonal anti-BCMA antibody comprising the following CDR sequences: DYYIN (SEQ ID NO. 61), WIYFASGNSEYNQKFTG (SEQ ID NO. 62), and LYDYDWYFDV (SEQ ID NO. 63), and KSSQSLVHSNGNTYLH (SEQ ID NO. 64), KVSNRFS (SEQ ID NO. 65), and AETSHVPWT (SEQ ID NO. 66) or SQSSIYPWT (SEQ ID NO. 67), a hinge selected from a FcγRIIIα hinge, a CD8α hinge, an IgG1 hinge, preferably a CD8α hinge or an IgG1 hinge, a transmembrane domain from CD8α and a cytoplasmic domain including a CD3 zeta signaling domain and a co-stimulatory domain from 4-1BB.

The present invention provides a BCMA specific chimeric antigen receptor according to the above, wherein said extra cellular ligand binding-domain VH and VL from a monoclonal anti-BCMA antibody comprises the following sequence:

```
                                        (SEQ ID NO. 68)
XXXXXXXXXXXXXXXXXXXXXXXXXXXXXDYYINXXXXXXXXXXXXXXW

IYFASGNSEYNQKFTGXXXXXXXXXXXXXXXXXXXXXXXXXXXXXXLY

DYDWYFDVXXXXXXXXXXX
```
and/or
```
                                        (SEQ ID NO. 69)
XXXXXXXXXXXXXXXXXXXXXXXXXKSSQSLVHSNGNTYLHXXXXXXXXXXXX

XXXXKVSNRFSXXXXXXXXXXXXXXXXXXXXXXXXXXXXXXSQSSIYP

WTXXXXXXXXXX
```
wherein X is an amino acid.

The present invention provides a BCMA (CD269) specific CAR according to the above, wherein said VH and VL have at least 80% identity with a polypeptide sequence selected from SEQ ID NO. 11 to 14.

The present invention provides a BCMA (CD269) specific chimeric antigen receptor (CAR) according to the above wherein said extra cellular ligand binding-domain comprising a VH from a monoclonal anti-BCMA antibody is selected from a sequence having at least 80% identity with SEQ ID NO 11 and SEQ ID NO 13 and said VL from a monoclonal anti-BCMA antibody is selected from a sequence having at least 80% identity with SEQ ID NO 12 and SEQ ID NO 14.

The present invention provides a BCMA specific chimeric antigen receptor according to the above, wherein said extra cellular ligand binding-domain comprising VH and VL from a monoclonal anti-BCMA antibody is humanized.

In one embodiment the present invention provides a BCMA specific CAR according to any one of the above, wherein said structure V1 comprises a FcγRIIIα hinge and CD8α transmembrane domain.

The present invention provides a BCMA specific CAR according to any one of the above, wherein said FcγRIIIα hinge has at least 80% identity with SEQ ID NO.3.

The present invention provides a BCMA specific CAR of structure V1 according any one of the above, which comprises a polypeptide sequence having at least 80% identity with SEQ ID NO. 19 or SEQ ID NO.25.

The present invention provides a BCMA specific CAR according to the above, wherein said structure V3 comprises a CD8α hinge and a CD8α transmembrane domain.

The present invention provides a BCMA specific CAR according to the above appropriate, wherein said CD8α hinge has at least 80% identity with SEQ ID NO.4.

The present invention provides a BCMA specific CAR of structure V3 according to any one of the above appropriate which comprises a polypeptide sequence having at least 80% identity with SEQ ID NO. 21 or SEQ ID NO.27.

In one embodiment the present invention provides a BCMA specific CAR according to any one of the above appropriate, wherein said structure V5 comprises an IgG1 hinge and a CD8α transmembrane domain.

The present invention provides a BCMA specific CAR according to any one of the above appropriate wherein said IgG1 hinge has at least 80% identity with SEQ ID NO.5.

The present invention provides a BCMA specific CAR of structure V5 according to any one of the above appropriate, which comprises a polypeptide sequence having at least 80% identity with SEQ ID NO. 23 or SEQ ID NO.35.

The present invention provides a BCMA specific CAR according to any one of the above, wherein co-stimulatory domain from 4-1BB has at least 80% identity with SEQ ID NO.8.

The present invention provides a BCMA specific CAR according to any one of the above, wherein said CD3 zeta signaling domain has at least 80% identity with SEQ ID NO. 9.

The present invention provides a BCMA specific CAR according to any one of the above, wherein said CD8α transmembrane domain has at least 80% identity with SEQ ID NO.6.

The present invention provides a BCMA specific CAR according to any one of the above, further comprising a signal peptide.

The present invention provides a BCMA specific CAR according to the above, wherein said signal peptide has at least 80% sequence identity with SEQ ID NO.1 or SEQ ID NO.2.

The present invention provides a BCMA specific CAR according to any one of the above further comprising another extracellular ligand binding domain which is not specific for BCMA.

The present invention provides a BCMA specific CAR according to any one of the above which is humanized.

In one aspect, the present invention provides a polynucleotide encoding a BCMA specific CAR according to any one of the above.

In one aspect, the present invention provides an expression vector comprising a polynucleotide encoding a BCMA specific CAR according to the above In another aspect, the present invention provides an engineered immune cell expressing at the cell surface membrane a BCMA specific chimeric antigen receptor according to the above.

The present invention provides an engineered immune cell according to the above, wherein expression of at least one MHC protein is suppressed, preferably a MHC associated β2 m protein.

The present invention provides an engineered immune cell according to any one of the above, wherein said cell is modified to become resistant to at least one immune suppressive drug or at least one chemotherapy drug, preferably said cell is modified to become resistant to at least one immune suppressive drug or a chemotherapy drug and further comprising a suicide gene.

The present invention provides an engineered immune cell according to any one of the above, derived from inflammatory T-lymphocytes, cytotoxic T-lymphocytes, regulatory T-lymphocytes or helper T-lymphocytes.

The present invention provides an engineered immune cell according to any one of the above, which is a TCR KO engineered immune T cell.

The present invention provides an engineered immune cell according to the above, which is further resistant to at one anti-cancer or anti-inflammatory disease chemotherapy.

In a preferred embodiment said engineered immune cell according to the above, is further resistant to at least one drug (chemotherapy) used against Multiple Myeloma or an-inflammatory disease.

In another aspect, the present invention provides an engineered immune cell according to the above for use in therapy.

The present invention provides an engineered immune cell for use in therapy according to the above, for the treatment of a pathological condition, wherein said pathological condition is a pre-malignant or malignant cancer condition related to BCMA-expressing cells.

The present invention provides an engineered immune cell for use in therapy according to the above, wherein the pathological condition is a condition which is characterized by an overabundance of BCMA-expressing cells.

The present invention provides an engineered immune cell according for use in therapy according to any one of the above, wherein the pathological condition is a haematological cancer condition.

The present invention provides an engineered immune cell for use in therapy according the above, wherein the haematological cancer condition is a leukemia.

The present invention provides an engineered immune cell for use in therapy according to the above embodiments, wherein the haematological cancer condition is multiple myeloma (MM).

The present invention provides an engineered cell for use in therapy according to the above, wherein said hematologic cancer is a malignant lymphoproliferative disorder.

The present invention provides an engineered cell for use in therapy according to the above, wherein said leukemia is selected from the group consisting of acute myelogenous leukemia, chronic myelogenous leukemia and myelodysplastic syndrome.

The present invention provides a method of impairing a hematologic cancer cell comprising contacting said cell with an engineered cell according to the above in an amount effective to cause impairment of said cancer cell.

The present invention provides a method of engineering an immune cell comprising:
(a) Providing an immune cell, optionally a TCR KO immune cell further resistant to at least one anti-cancer chemotherapy, (b) Expressing at the surface of said cell at least one BCMA specific chimeric antigen receptor according to any one of the above.

The present invention provides a method of engineering an immune cell as above comprising:
(a) Providing an immune cell, optionally a TCR KO immune cell further resistant to at least one anti-cancer chemotherapy
(b) Introducing into said cell at least one polynucleotide encoding said BCMA specific chimeric antigen receptor,
(c) Expressing said polynucleotide into said cell.

The present invention provides a method of engineering an immune cell as above comprising:
(a) Providing an immune cell, optionally a TCR KO immune cell further resistant to at least one anti-cancer chemotherapy
(b) Introducing into said cell at least one polynucleotide encoding said BCMA specific chimeric antigen receptor,
(c) Introducing at least one other chimeric antigen receptor which is not specific for BCMA.

The present invention provides a method of treating a subject in need thereof comprising:
(a) Providing an immune cell expressing at the surface a BCMA specific Chimeric Antigen Receptor according to the above; optionally a TCR KO immune cell further resistant to at least one anti-cancer chemotherapy
(b) Administrating said immune cells to said patient.

The present invention provides a method as above wherein said immune cell is provided from a donor.

The present invention provides a method as above, wherein said immune cell is provided from the patient himself.

Preferred CAR polypeptides of the invention comprise an amino acid sequence selected from SEQ ID NO.19 to 42.

In one embodiment, the present invention provides a composition for its use in the treatment of a BCMA expressing cells-mediated disease, in particular a BCMA expressing cells—mediated hematologic cancer, said composition comprising said anti-BCMA CAR expressing T cell of the invention, preferably said anti-BCMA CAR is of SEQ ID NO. 50 or of SEQ ID NO. 56.

In one embodiment, the invention provides a BCMA CAR comprising an amino acid sequence selected from SEQ ID NO.19, SEQ ID NO.21, SEQ ID NO.23, SEQ ID NO.25, SEQ ID NO.27 and SEQ ID NO.29, preferably SEQ ID NO.21, SEQ ID NO.23, SEQ ID NO.27, SEQ ID NO.29, more preferably SEQ ID NO.21 or SEQ ID NO.27.

More preferred CAR of the invention comprise an amino acid sequence having at least 80% identity with an amino acid sequence selected from SEQ ID NO.19, SEQ ID NO.21, SEQ ID NO.23, SEQ ID NO.25, SEQ ID NO.27, SEQ ID NO.29.

Even more preferred CAR of the invention comprise an amino acid sequence having at least 80% identity with an amino acid sequence selected from SEQ ID NO.21, SEQ ID NO.23, SEQ ID NO.27, SEQ ID NO.29 and even more preferred having at least 80% identity with SEQ ID NO.21 or SEQ ID NO.27.

In one embodiment, preferred CAR of the invention comprise an amino acid sequence having at least 80% identity with an amino acid sequence selected from SEQ ID NO. 48, SEQ ID NO. 50, SEQ ID NO. 52, SEQ ID NO. 54, SEQ ID NO. 56 and SEQ ID NO. 58. More preferred CAR of the invention comprise an amino acid sequence having at least 80% identity with an amino acid sequence selected from SEQ ID NO. 50, SEQ ID NO. 52, SEQ ID NO. 56 and SEQ ID NO. 58.

In another embodiment, CAR of the invention comprises an amino acid sequence selected from SEQ ID NO. 48, SEQ ID NO. 50, SEQ ID NO. 52, SEQ ID NO. 54, SEQ ID NO. 56 and SEQ ID NO. 58. More preferred CAR of the invention comprise an amino acid sequence selected from SEQ ID NO. 50, SEQ ID NO. 52 SEQ ID NO. 56 and SEQ ID NO. 58.

In other embodiment, the present invention provides a composition for its use in the treatment of a BCMA expressing cells-mediated disease, in particular a BCMA expressing cells—mediated hematologic cancer, said composition comprising said anti-BCMA CAR expressing T cell of the invention, as those described just below.

Following non-specific activation in vitro (e.g. with anti CD3/CD28 coated beads and recombinant IL2), T-cells from donors have been transformed with polynucleotides expressing these CARs using viral transduction. In certain instances, the T-cells were further engineered to create non-alloreactive T-cells, more especially by disruption of a component of TCR (αβ—Cell receptors) to prevent Graft versus host reaction. In a preferred embodiment, the T-cells were further engineered by disruption of TCR (αβ—T-Cell receptors) and by modifying at least one gene to confer said engineered T cells resistance to at least one drug, for example a drug used against cancer.

A CAR expressing immune T cell targeting BCMA according to the invention can be used in combination with cytotoxic chemotherapy agents as a treatment usually employed as anti-cancer treatments. The resulting engineered T-cells displayed reactivity in-vitro against BCMA positive cells to various extend, showing that the CARs of the present invention contribute to antigen dependent activation, and also proliferation, of the T-cells, making them useful for immunotherapy.

In addition, the resulting engineered T-cells display increased selectivity in vitro and increased cytolytic activity under particular and specific conditions as compared to engineered T-cells expressing a BCMA CAR derived from C11D5.3.

The polypeptides and polynucleotide sequences encoding the CARs of the present invention are detailed in the present specification.

The engineered immune cells of the present invention are particularly useful for therapeutic applications, such as for treating multiple myeloma.

TABLE 1

Sequence of the different CAR components

Figure 1:
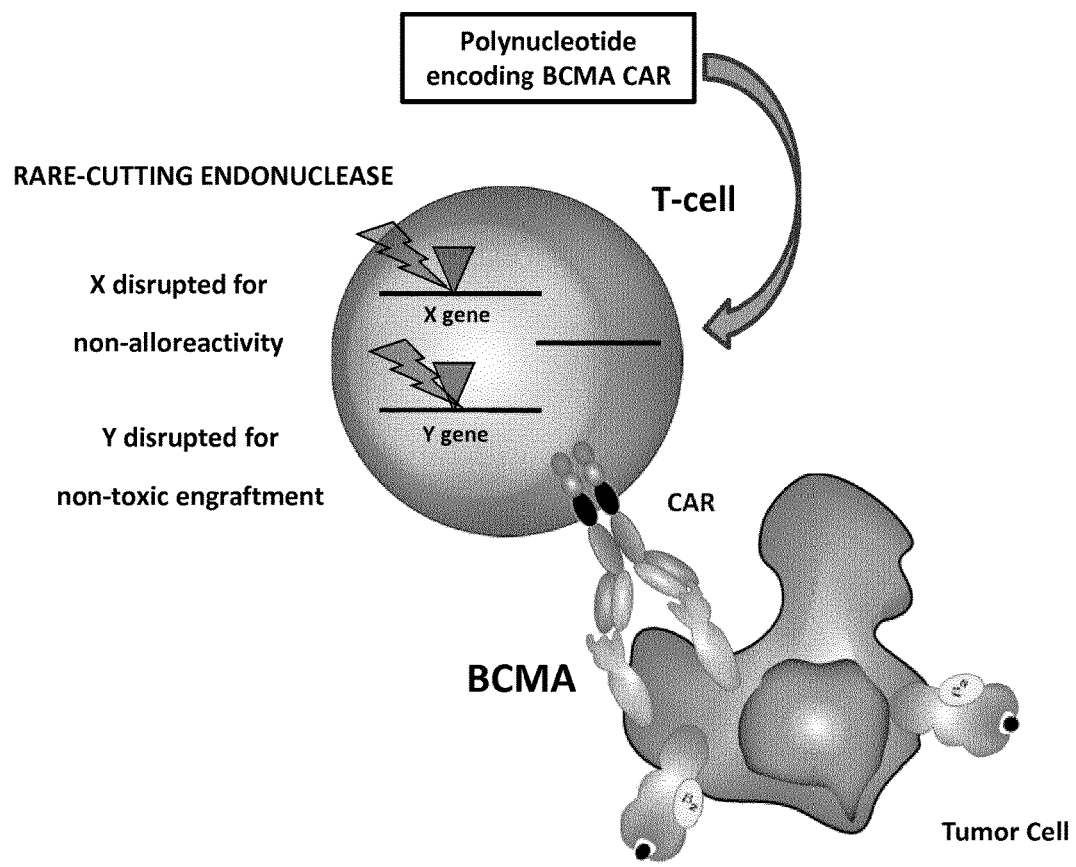
FIG. 1: Schematic representation of an engineered immune cell according to the invention. The engineered immune cell presented in this figure is a T-cell transduced with a retroviral polypeptide encoding CAR. This T-cell is further engineered to allow a better and safer engraftment into the patient, which is optional within the frame of the present invention. X gene may be for instance a gene expressing a component of TCR (TCRalpha or TCRbeta), Y may be a gene involved into the sensitivity of T-cells to immune-suppressive drugs like CD52 (with respect to Campath) or HPRT (with respect to 6-Thioguanine).

| Functional domains | SEQ ID # | Raw amino acid sequence |
|---|---|---|
| CD8α signal peptide | SEQ ID NO. 1 | MALPVTALLLPLALLLHAARP |
| Alternative signal peptide | SEQ ID NO. 2 | METDTLLLWVLLLWVPGSTG |
| FcγRIIIα hinge | SEQ ID NO. 3 | GLAVSTISSFFPPGYQ |
| CD8α hinge | SEQ ID NO. 4 | TTTPAPRPPTPAPTIASQPLSLRPEA CRPAAGGAVHTRGLDFACD |
| IgG1 hinge | SEQ ID NO. 5 | EPKSPDKTHTCPPCPAPPVAGPSV FLFPPKPKDTLMIARTPEVTCVVVD VSHEDPEVKFNWYVDGVEVHNAKT KPREEQYNSTYRVVSVLTVLHQDW LNGKEYKCKVSNKALPAPIEKTISKA KGQPREPQVYTLPPSRDELTKNQV SLTCLVKGFYPSDIAVEWESNGQPE NNYKTTPPVLDSDGSFFLYSKLTVD KSRWQQGNVFSCSVMHEALHNHY TQKSLSLSPGK |
| CD8α transmembrane domain | SEQ ID NO. 6 | IYIWAPLAGTCGVLLLSLVITLYC |
| 41BB transmembrane domain | SEQ ID NO. 7 | IISFFLALTSTALLFLLFFLTLRFSVV |
| 41BB intracellular domain | SEQ ID NO. 8 | KRGRKKLLYIFKQPFMRPVQTTQEE DGCSCRFPEEEEGGCEL |
| CD3ζ intracellular domain | SEQ ID NO. 9 | RVKFSRSADAPAYQQGQNQLYNEL NLGRREEYDVLDKRRGRDPEMGG KPRRKNPQEGLYNELQKDKMAEAY SEIGMKGERRRGKGHDGLYQGLST ATKDTYDALHMQALPPR |
| Linker | SEQ ID NO. 10 | GGGGSGGGGSGGGGS |

TABLE 2

Sequence of the different CAR components

| ScFv sequences | SEQ ID # | Raw amino acid sequence |
|---|---|---|
| BCMA-50 heavy chain variable region | SEQ ID NO. 11 | QVQLVQSGAEVKKPGASVKVSCKASG YSFPDYYINWVRQAPGQGLEWMGWIY FASGNSEYNQKFTGRVTMTRDTSINTA YMELSSLTSEDTAVYFCASLYDYDWYF DVWGQGTMVTVSS |
| BCMA-50 light chain variable region | SEQ ID NO. 12 | DIVMTQTPLSLSVTPGQPASISCKSSQS LVHSNGNTYLHWYLQKPGQSPQLLIYK VSNRFSGVPDRFSGSGSGTDFTLKISR VEAEDVGIYYCSQSSIYPWTFGQGTKL EIK |
| BCMA-30 heavy chain variable region | SEQ ID NO. 13 | QVQLVQSGAEVKKPGASVKVSCKASG YSFPDYYINWVRQAPGQGLEWMGWIY FASGNSEYNQKFTGRVTMTRDTSSST AYMELSSLRSEDTAVYFCASLYDYDWY FDVWGQGTMVTVSS |
| BCMA-30 light chain variable region | SEQ ID NO. 14 | DIVMTQTPLSLSVTPGEPASISCKSSQS LVHSNGNTYLHWYLQKPGQSPQLLIYK VSNRFSGVPDRFSGSGSGADFTLKISR VEAEDVGVYYCAETSHVPWTFGQGTK LEIK |
| C11D5.3 heavy chain variable | SEQ ID NO. 15 | QIQLVQSGPELKKPGETVKISCKASGYT FTDYSINWVKRAPGKGLKWMGWINTE |

TABLE 2-continued

Sequence of the different CAR components

| ScFv sequences | SEQ ID # | Raw amino acid sequence |
|---|---|---|
| region | | TREPAYAYDFRGRFAFSLETSASTAYL QINNLKYEDTATYFCALDYSYAMDYWG QGTSVTVSS |
| C11D5.3 light chain variable region | SEQ ID NO. 16 | DIVLTGSPPSLAMSLGKRATISCRASES VTILGSHLIHWYQQKPGQPPTLLIQLAS NVQTGVPARFSGSGSRTDFTLTIDPVE EDDVAVYYCLQSRTIPRTFGGGTKLEIK |
| C13F12.1 heavy chain variable region | SEQ ID NO. 17 | QIQLVQSGPELKKPGETVKISCKASGYT FTHYSMNWVKQAPGKGLKWMGRINTE TGEPLYADDFKGRFAFSLETSASTAYL VINNLKNEDTATFFCSNDYLYSCDYWG RGTTLTVSS |
| C13F12.1 light chain variable region | SEQ ID NO. 18 | DIVLTQSPPSLAMSLGKRATISCRASES VTILGSHLIYWYQQKPGQPPTLLIQLAS NVQTGVPARFSGSGSRTDFTLTIDPVE EDDVAVYYCLQSRTIPRTFGGGTKLEIK |

TABLE 3

CAR of structure V-1

| | CAR Structure | | | | | | |
|---|---|---|---|---|---|---|---|
| CAR Designation V-1 | signal peptide (optional) | VH | VL | FcγRIIIα hinge | CD8α TM | 41BB-IC | CD3ζ CD |
| BC50-1 (SEQ ID NO.19) | SEQ ID NO.1 | SEQ ID NO.11 | SEQ ID NO.12 | SEQ ID NO.3 | SEQ ID NO.6 | SEQ ID NO.8 | SEQ ID NO.9 |
| BC30-1 (SEQ ID NO.25) | SEQ ID NO.1 | SEQ ID NO.13 | SEQ ID NO.14 | SEQ ID NO.3 | SEQ ID NO.6 | SEQ ID NO.8 | SEQ ID NO.9 |
| C11D53-1 (SEQ ID NO.31) | SEQ ID NO.1 | SEQ ID NO.15 | SEQ ID NO.16 | SEQ ID NO.3 | SEQ ID NO.6 | SEQ ID NO.8 | SEQ ID NO.9 |
| C13F12-1 (SEQ ID NO.37) | SEQ ID NO.1 | SEQ ID NO.17 | SEQ ID NO.18 | SEQ ID NO.3 | SEQ ID NO.6 | SEQ ID NO.8 | SEQ ID NO.9 |

TABLE 4

CAR of structure V-2

| | CAR Structure | | | | | | |
|---|---|---|---|---|---|---|---|
| CAR Designation V-2 | signal peptide (optional) | VH | VL | FcγRIIIα hinge | 41BB-TM | 41BB-IC | CD3ζ CD |
| BC50-2 (SEQ ID NO.20) | SEQ ID NO.1 | SEQ ID NO.11 | SEQ ID NO.12 | SEQ ID NO.3 | SEQ ID NO.7 | SEQ ID NO.8 | SEQ ID NO.9 |
| BC30-2 (SEQ ID NO.26) | SEQ ID NO.1 | SEQ ID NO.13 | SEQ ID NO.14 | SEQ ID NO.3 | SEQ ID NO.7 | SEQ ID NO.8 | SEQ ID NO.9 |
| C11D53-2 (SEQ ID NO.32) | SEQ ID NO.1 | SEQ ID NO.15 | SEQ ID NO.16 | SEQ ID NO.3 | SEQ ID NO.7 | SEQ ID NO.8 | SEQ ID NO.9 |
| C13F12-2 (SEQ ID NO.38) | SEQ ID NO.1 | SEQ ID NO.17 | SEQ ID NO.18 | SEQ ID NO.3 | SEQ ID NO.7 | SEQ ID NO.8 | SEQ ID NO.9 |

TABLE 5

CAR of structure V-3

| CAR Designation V-3 | signal peptide (optional) | VH | VL | CD8α hinge | CD8α TM | 41BB-IC | CD3ζ CD |
|---|---|---|---|---|---|---|---|
| BC50-3 (SEQ ID NO.21) | SEQ ID NO.1 | SEQ ID NO.11 | SEQ ID NO.12 | SEQ ID NO.4 | SEQ ID NO.6 | SEQ ID NO.8 | SEQ ID NO.9 |
| BC30-3 (SEQ ID NO.27) | SEQ ID NO.1 | SEQ ID NO.13 | SEQ ID NO.14 | SEQ ID NO.4 | SEQ ID NO.6 | SEQ ID NO.8 | SEQ ID NO.9 |
| C11D53-3 (SEQ ID NO.33) | SEQ ID NO.1 | SEQ ID NO.15 | SEQ ID NO.16 | SEQ ID NO.4 | SEQ ID NO.6 | SEQ ID NO.8 | SEQ ID NO.9 |
| C13F12-3 (SEQ ID NO.39) | SEQ ID NO.1 | SEQ ID NO.17 | SEQ ID NO.18 | SEQ ID NO.4 | SEQ ID NO.6 | SEQ ID NO.8 | SEQ ID NO.9 |

TABLE 6

CAR of structure V-4

| CAR Designation V-4 | signal peptide (optional) | VH | VL | CD8α hinge | 41BB-TM | 41BB-IC | CD3ζ CD |
|---|---|---|---|---|---|---|---|
| BC50-4 (SEQ ID NO.22) | SEQ ID NO.1 | SEQ ID NO.11 | SEQ ID NO.12 | SEQ ID NO.4 | SEQ ID NO.7 | SEQ ID NO.8 | SEQ ID NO.9 |
| BC30-4 (SEQ ID NO.28) | SEQ ID NO.1 | SEQ ID NO.13 | SEQ ID NO.14 | SEQ ID NO.4 | SEQ ID NO.7 | SEQ ID NO.8 | SEQ ID NO.9 |
| C11D53-4 (SEQ ID NO.34) | SEQ ID NO.1 | SEQ ID NO.15 | SEQ ID NO.16 | SEQ ID NO.4 | SEQ ID NO.7 | SEQ ID NO.8 | SEQ ID NO.9 |
| C13F12-5 (SEQ ID NO.40) | SEQ ID NO.1 | SEQ ID NO.17 | SEQ ID NO.18 | SEQ ID NO.4 | SEQ ID NO.7 | SEQ ID NO.8 | SEQ ID NO.9 |

TABLE 7

CAR of structure V-5

| CAR Designation V-5 | signal peptide (optional) | VH | VL | IgG1 hinge | CD8α TM | 41BB-IC | CD3ζ CD |
|---|---|---|---|---|---|---|---|
| BC50-5 (SEQ ID NO.23) | SEQ ID NO.1 | SEQ ID NO.11 | SEQ ID NO.12 | SEQ ID NO.5 | SEQ ID NO.6 | SEQ ID NO.8 | SEQ ID NO.9 |
| BC30-5 (SEQ ID NO.29) | SEQ ID NO.1 | SEQ ID NO.13 | SEQ ID NO.14 | SEQ ID NO.5 | SEQ ID NO.6 | SEQ ID NO.8 | SEQ ID NO.9 |
| C11D53-5 (SEQ ID NO.35) | SEQ ID NO.1 | SEQ ID NO.15 | SEQ ID NO.16 | SEQ ID NO.5 | SEQ ID NO.6 | SEQ ID NO.8 | SEQ ID NO.9 |
| C13F12-5 (SEQ ID NO.41) | SEQ ID NO.1 | SEQ ID NO.17 | SEQ ID NO.18 | SEQ ID NO.5 | SEQ ID NO.6 | SEQ ID NO.8 | SEQ ID NO.9 |

TABLE 8

CAR of structure V-6

| CAR Designation V-6 | signal peptide (optional) | VH | VL | IgG1 hinge | 41BB-TM | 41BB-IC | CD3ζ CD |
|---|---|---|---|---|---|---|---|
| BC50-6 (SEQ ID NO.24) | SEQ ID NO.1 | SEQ ID NO.11 | SEQ ID NO.12 | SEQ ID NO.5 | SEQ ID NO.7 | SEQ ID NO.8 | SEQ ID NO.9 |
| BC30-6 (SEQ ID NO.30) | SEQ ID NO.1 | SEQ ID NO.13 | SEQ ID NO.14 | SEQ ID NO.5 | SEQ ID NO.7 | SEQ ID NO.8 | SEQ ID NO.9 |
| C11D53-6 (SEQ ID NO.36) | SEQ ID NO.1 | SEQ ID NO.15 | SEQ ID NO.16 | SEQ ID NO.5 | SEQ ID NO.7 | SEQ ID NO.8 | SEQ ID NO.9 |
| C13F12-6 (SEQ ID NO.42) | SEQ ID NO.1 | SEQ ID NO.17 | SEQ ID NO.18 | SEQ ID NO.5 | SEQ ID NO.7 | SEQ ID NO.8 | SEQ ID NO.9 |

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Cabs eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

BCMA specific Chimeric Antigen Receptors

The present invention relates to new designs of anti-BCMA chimeric antigen receptor (CAR) comprising an extracellular ligand-binding domain, a transmembrane domain and a signaling transducing domain.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. In a preferred embodiment, said extracellular ligand-binding domain comprises a single chain antibody fragment (scFv) comprising the light ($V_L$) and the heavy ($V_H$) variable fragment of a target antigen specific monoclonal anti BCMAantibody joined by a flexible linker. Said $V_L$ and $V_H$ are preferably selected from the antibodies referred to as BCMA-50, BCMA-30, C11D5.3 and C13F12.1 as indicated in Table 2. They are preferably linked together by a flexible linker comprising for instance the sequence SEQ ID NO.10.

In a more preferred embodiment Said $V_L$ and $V_H$ are preferably selected from the antibodies referred to as BCMA-50 (BC50) and BCMA-30 (BC30) as indicated in Table 2.

In some embodiments, the extracellular ligand-binding domain comprises a scFv comprising the light chain variable (VL) region and the heavy chain variable (VH) region of a BCMA specific monoclonal antibody joined by a flexible linker. Single chain variable region fragments are made by linking light and/or heavy chain variable regions by using a short linking peptide (Bird et al., Science 242:423-426, 1988).

In general, linkers of the present invention are short, flexible polypeptides and preferably comprised at least 20 or fewer amino acid residues. Linkers of the present invention can in turn be modified for additional functions, such as attachment of drugs or attachment to solid supports.

An example of a linking peptide is the GS linker having the amino acid sequence (GGGGS)$_3$ (SEQ ID NO:10), which bridges approximately 3.5 nm between the carboxy terminus of one variable region and the amino terminus of the other variable region. Linkers of other sequences have been designed and used (Bird et al., 1988, supra).

The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In other words, said CARs preferentially comprise an extracellular ligand-binding domain comprising a polypeptide sequence displaying at least 90%, 95%, 97% 99%, or 100% identity with an amino acid sequence selected from the group consisting of SEQ ID NO: 11 to SEQ ID NO: 18. In a more preferred embodiment, said CARs comprise an extracellular ligand-binding domain comprising a polypeptide sequence displaying at least 90%, 91%, 92%, 93% 94%, 95%, 96%, 97%, 98%, 99% or 100% identity with an amino acid sequence selected from the group consisting of SEQ ID NO: 11, SEQ ID NO 12, SEQ ID NO 13, SEQ ID NO: 14 and a combination thereof.

The signal transducing domain or intracellular signaling domain of a CAR according to the present invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% or 99% sequence identity with amino acid sequence selected from the group consisting of (SEQ ID NO: 9).

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to, an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transduction domain of the CAR of the present invention comprises a part of co-stimulatory signal molecule selected from the group consisting of fragment of 4-1BB (GenBank: AAA53133.) and CD28 (NP_006130.1). In particular the signal transduction domain of the CAR of the present invention comprises amino acid sequence which comprises at least 70%, preferably at least 80%, more preferably at least 90%, 95% 97% or 99% sequence identity with amino acid sequence selected from the group consisting of SEQ ID NO: 8.

A CAR according to the present invention is expressed on the surface membrane of the cell. Thus, such CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, γ or δ, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1) The transmembrane domain can further comprise a hinge region between said extracellular ligand-binding domain and said transmembrane domain. The term "hinge region" used herein generally means any oligo- or polypeptide that functions to link the transmembrane domain to the extracellular ligand-binding domain. In particular, hinge region are used to provide more flexibility and accessibility for the extracellular ligand-binding domain. A hinge region may comprise up to 300 amino acids, preferably 10 to 100 amino acids and most preferably 25 to 50 amino acids. Hinge region may be derived from all or part of naturally occurring molecules, such as from all or part of the extracellular region of CD8, CD4 or CD28, or from all or part of an antibody constant region. Alternatively the hinge region may be a synthetic sequence that corresponds to a naturally occurring hinge sequence, or may be an entirely synthetic hinge sequence. In a preferred embodiment said hinge domain comprises a part of human CD8 alpha chain, FcγRIIIα receptor or IgG1 respectively referred to in this specification as SEQ ID NO. 3, SEQ ID NO. 4 and SEQ ID NO.5, or hinge polypeptides which display preferably at least 80%, more preferably at least 90%, 95% 97% or 99% sequence identity with these polypeptides.

A car according to the invention generally further comprises a transmembrane domain (TM) more particularly selected from CD8α and 4-1BB, showing identity with the polypeptides of SEQ ID NO. 6 or 7, preferably with the polypeptide of SEQ ID NO 6.

A car according to the invention generally further comprises a transmembrane domain (TM) more particularly selected from CD8α, showing identity with the polypeptides of SEQ ID NO. 6, In a preferred embodiment, a CAR according to the invention further comprises a TM domain from CD8α with SEQ ID NO. 6 or showing at least 90%, 91%, 92%, 93%, 94%, 95%, 96%, 97%, 98%, 99% or 100% sequence identity with SEQ ID NO. 6

Downregulation or mutation of target antigens is commonly observed in cancer cells, creating antigen-loss escape variants. Thus, to offset tumor escape and render immune cell more specific to target, the BCMA specific CAR according to the invention can comprise another extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains. In particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

Figure 2:
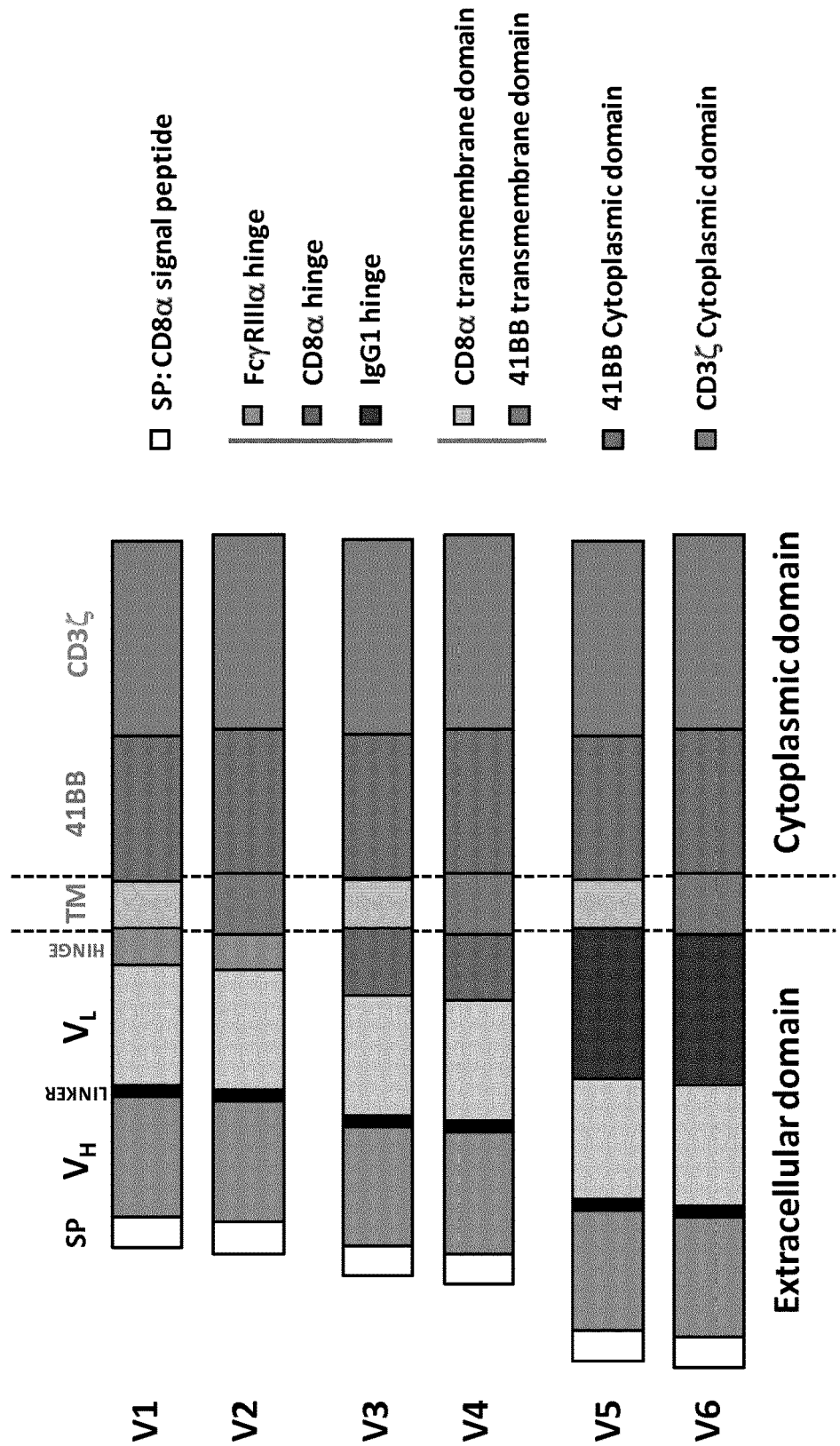
FIG. 2: Schematic representation of the different CAR Architecture (V1 to V6).

The present invention provides a BCMA specific chimeric antigen receptor (CAR) having one of the polypeptide structure selected from V1 to V6 as illustrated in FIG. 2, said structure comprising an extra cellular ligand binding-domain comprising VH and VL from a monoclonal anti-BCMA antibody, a hinge selected from a FcRIIIalpha(α) hinge, a CD8α hinge and an IgG1 hinge, a CD8α transmembrane domain and a cytoplasmic domain including a CD3 zeta signaling domain and a co-stimulatory domain from 4-1BB.

The present invention provides a BCMA specific chimeric antigen receptor (CAR) having one of the polypeptide structure selected from V1, V3 and V5 as illustrated in FIG. 2, said structure comprising an extra cellular ligand binding-domain comprising VH and VL from a monoclonal anti-BCMA antibody, a hinge selected from a FcRIIIα hinge, a CD8 alpha (α) hinge and an IgG1 hinge, a CD8α transmembrane domain and a cytoplasmic domain including a CD3 zeta signaling domain and a co-stimulatory domain from 4-1BB.

In particular, the present invention provides a BCMA specific chimeric antigen receptor (CAR) having one of the polypeptide structure selected from V1, V3 and V5 as illustrated in FIG. 2, said structure comprising an extra cellular ligand binding-domain derived from a VH and a VL from a monoclonal anti-BCMA antibody, a hinge selected from a FcRIIIα hinge, a CD8 alpha (α) hinge and an IgG1 hinge, a CD8α transmembrane domain and a cytoplasmic domain including a CD3 zeta signaling domain and a co-stimulatory domain from 4-1BB, more particularly the present invention provides a BCMA specific chimeric antigen receptor (CAR) having one of the polypeptide structure selected from V1, V3 and V5 as illustrated in FIG. 2, said structure comprising an extra cellular ligand binding-domain derived from a VH and a VL from a monoclonal anti-BCMA antibody selected from BC50 and BC30, a hinge selected from a FcRIIIα hinge, a CD8 alpha (α) hinge and an IgG1 hinge, a CD8α transmembrane domain and a cytoplasmic domain including a CD3 zeta signaling domain and a co-stimulatory domain from 4-1BB.

In a preferred embodiment, the present invention provides a BCMA specific chimeric antigen receptor (CAR) having one of the polypeptide structure selected from V1, V3 and V5 as illustrated in FIG. 2, said structure comprising an extra cellular ligand binding-domain derived from a VH having a sequence selected from SEQ ID NO.11, and SEQ ID NO.13, and a VL from a monoclonal anti-BCMA antibody having a sequence selected from SEQ ID NO.12, and SEQ ID NO.14, a hinge selected from a FcRIIIα hinge, a CD8 alpha (α) hinge and an IgG1 hinge, a CD8α transmembrane domain and a cytoplasmic domain including a CD3 zeta signaling domain and a co-stimulatory domain from 4-1BB.

In a preferred embodiment, the present invention provides a BCMA specific chimeric antigen receptor (CAR) having one of the polypeptide structure V5 as illustrated in FIG. 2, said structure comprising an extra cellular ligand binding-domain derived from a VH having a sequence selected from SEQ ID NO.11, and SEQ ID NO.13 and a VL from a monoclonal anti-BCMA antibody having a sequence selected from SEQ ID NO.12 and SEQ ID NO.14, an IgG1 hinge, a CD8α transmembrane domain and a cytoplasmic domain including a CD3 zeta signaling domain and a co-stimulatory domain from 4-1BB.

In another preferred embodiment, the present invention provides a BCMA specific chimeric antigen receptor (CAR) having one of the polypeptide structure V1 as illustrated in FIG. 2, said structure comprising an extra cellular ligand binding-domain derived from a VH having a sequence selected from SEQ ID NO.11, and SEQ ID NO.13 and a VL from a monoclonal anti-BCMA antibody having a sequence selected from SEQ ID NO.12 and SEQ ID NO.14, a FcRIIIα hinge, a CD8α transmembrane domain and a cytoplasmic domain including a CD3 zeta signaling domain and a co-stimulatory domain from 4-1BB.

In a more preferred embodiment, the present invention provides a BCMA specific chimeric antigen receptor (CAR) having one of the polypeptide structure V3 as illustrated in FIG. 2, said structure comprising an extra cellular ligand binding-domain derived from a VH having a sequence selected from SEQ ID NO.11, and SEQ ID NO.13 and a VL from a monoclonal anti-BCMA antibody having a sequence selected from SEQ ID NO.12 and SEQ ID NO.14, a CD8 alpha (α) hinge, a CD8α transmembrane domain and a cytoplasmic domain including a CD3 zeta signaling domain and a co-stimulatory domain from 4-1BB.

In one embodiment the present invention provides a BCMA specific chimeric antigen receptor (CAR) comprising one of the following polypeptide:

```
(BC50-1)
                                                      SEQ ID NO. 48
MALPVTALLLPLALLLHAARPQVQLVQSGAEVKKPGASVKVSCKASGYSFPDYYINWVRQA

PGQGLEWMGWIYFASGNSEYNQKFTGRVTMTRDTSINTAYMELSSLTSEDTAVYFCASLY

DYDWYFDVWGQGTMVTVSSGGGGSGGGGSGGGGSDIVMTQTPLSLSVTPGQPASISCK

SSQSLVHSNGNTYLHWYLQKPGQSPQLLIYKVSNRFSGVPDRFSGSGSGTDFTLKISRVEA

EDVGIYYCSQSSIYPWTFGQGTKLEIKGLAVSTISSFFPPGYQIYIWAPLAGTCGVLLLSLVITL

YCKRGRKKLLYIFKQPFMRPVQTTQEEDGCSCRFPEEEEGGCELRVKFSRSADAPAYQQG

QNQLYNELNLGRREEYDVLDKRRGRDPEMGGKPRRKNPQEGLYNELQKDKMAEAYSEG

MKGERRRGKGHDGLYQGLSTATKDTYDALHMQALPPR (BC50-3)
                                                      SEQ ID NO. 50
MALPVTALLLPLALLLHAARPQVQLVQSGAEVKKPGASVKVSCKASGYSFPDYYINWVRQA

PGQGLEWMGWIYFASGNSEYNQKFTGRVTMTRDTSINTAYMELSSLTSEDTAVYFCASLY

DYDWYFDVWGQGTMVTVSSGGGGSGGGGSGGGGSDIVMTQTPLSLSVTPGQPASISCK

SSQSLVHSNGNTYLHWYLQKPGQSPQLLIYKVSNRFSGVPDRFSGSGSGTDFTLKISRVEA

EDVGIYYCSQSSIYPWTFGQGTKLEIKTTTPAPRPPTPAPTIASQPLSLRPEACRPAAGGAV

HTRGLDFACDIYIWAPLAGTCGVLLLSLVITLYCKRGRKKLLYIFKQPFMRPVQTTQEEDGCS

CRFPEEEEGGCELRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTATKDTYDALH

MQALPPR (BC50-5)
                                                      SEQ ID NO. 52
MALPVTALLLPLALLLHAARPQVQLVQSGAEVKKPGASVKVSCKASGYSFPDYYINWVRQA

PGQGLEWMGWIYFASGNSEYNQKFTGRVTMTRDTSINTAYMELSSLTSEDTAVYFCASLY

DYDWYFDVWGQGTMVTVSSGGGGSGGGGSGGGGSDIVMTQTPLSLSVTPGQPASISCK

SSQSLVHSNGNTYLHWYLQKPGQSPQLLIYKVSNRFSGVPDRFSGSGSGTDFTLKISRVEA

EDVGIYYCSQSSIYPWTFGQGTKLEIKEPKSPDKTHTCPPCPAPPVAGPSVFLFPPKPKDTL

MIARTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSVMHEALH

NHYTQKSLSLSPGKIYIWAPLAGTCGVLLLSLVITLYCKRGRKKLLYIFKQPFMRPVQTTQEE

DGCSCRFPEEEEGGCELRVKFSRSADAPAYQQGQNQLYNELNLGRREEYDVLDKRRGRD
```

PEMGGKPRRKNPQEGLYNELQKDKMAEAYSEIGMKGERRRGKGHDGLYQGLSTATKDTY

DALHMQALPPR (BC30-1)
SEQ ID NO. 54
MALPVTALLLPLALLLHAARPQVQLVQSGAEVKKPGASVKVSCKASGYSFPDYYINWVRQA

PGQGLEWMGWIYFASGNSEYNQKFTGRVTMTRDTSSSTAYMELSSLRSEDTAVYFCASLY

DYDWYFDVWGQGTMVTVSSGGGGSGGGGSGGGGSDIVMTQTPLSLSVTPGEPASISCK

SSQSLVHSNGNTYLHWYLQKPGQSPQLLIYKVSNRFSGVPDRFSGSGSGADFTLKISRVEA

EDVGVYYCAETSHVPWTFGQGTKLEIKGLAVSTISSFFPPGYQIYIWAPLAGTCGVLLLSLVI

TLYCKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSE

IGMKGERRRGKGHDGLYQGLSTATKDTYDALHMQALPPR (BC30-3)
SEQ ID NO. 56
MALPVTALLLPLALLLHAARPQVQLVQSGAEVKKPGASVKVSCKASGYSFPDYYINWVRQA

PGQGLEWMGWIYFASGNSEYNQKFTGRVTMTRDTSSSTAYMELSSLRSEDTAVYFCASLY

DYDWYFDVWGQGTMVTVSSGGGGSGGGGSGGGGSDIVMTQTPLSLSVTPGEPASISCK

SSQSLVHSNGNTYLHWYLQKPGQSPQLLIYKVSNRFSGVPDRFSGSGSGADFTLKISRVEA

EDVGVYYCAETSHVPWTFGQGTKLEIKTTTPAPRPPTPAPTIASQPLSLRPEACRPAAGGA

VHTRGLDFACDIYIWAPLAGTCGVLLLSLVITLYCKRGRKKLLYIFKQPFMRPVQTTQEEDGC

SCRFPEEEEGGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLSTATKDTYDAL

HMQALPPR (BC30-5)
SEQ ID NO. 58
MALPVTALLLPLALLLHAARPQVQLVQSGAEVKKPGASVKVSCKASGYSFPDYYINWVRQA

PGQGLEWMGWIYFASGNSEYNQKFTGRVTMTRDTSSSTAYMELSSLRSEDTAVYFCASLY

DYDWYFDVWGQGTMVTVSSGGGGSGGGGSGGGGSDIVMTQTPLSLSVTPGEPASISCK

SSQSLVHSNGNTYLHWYLQKPGQSPQLLIYKVSNRFSGVPDRFSGSGSGADFTLKISRVEA

EDVGVYYCAETSHVPWTFGQGTKLEIKEPKSPDKTHTCPPCPAPPVAGPSVFLFPPKPKDT

LMIARTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSVMHEALH

NHYTQKSLSLSPGKIYIWAPLAGTCGVLLLSLVITLYCKRGRKKLLYIFKQPFMRPVQTTQEE

DGCSCRFPEEEEGGCELRVKFSRSADAPAYQQGQNQLYNELNLGRREEYDVLDKRRGRD

PEMGGKPRRKNPQEGLYNELQKDKMAEAYSEIGMKGERRRGKGHDGLYQGLSTATKDTY

DALHMQALPPR.

(BC50-3) In particular
SEQ ID NO. 50
MALPVTALLLPLALLLHAARPQVQLVQSGAEVKKPGASVKVSCKASGYSFPDYYINWVRQA

PGQGLEWMGWIYFASGNSEYNQKFTGRVTMTRDTSINTAYMELSSLTSEDTAVYFCASLY

```
DYDWYFDVWGQGTMVTVSS GGGGSGGGGSGGGGS DIVMTQTPLSLSVTPGQPASISCK

SSQSLVHSNGNTYLHWYLQKPGQSPQLLIYKVSNRFSGVPDRFSGSGSGTDFTLKISRVEA

EDVGIYYCSQSSIYPWTFGQGTKLEIK TTTPAPRPPTPAPTIASQPLSLRPEACRPAAGGAV

HTRGLDFACDIYIWAPLAGTCGVLLLSLVITLYCKRGRKKLLYIFKQPFMRPVQTTQEEDGCS

CRFPEEEEGGCELRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTATKDTYDALH

MQALPPR or (BC30-3)
                                                    SEQ ID NO. 56
MALPVTALLLPLALLLHAARP QVQLVQSGAEVKKPGASVKVSCKASGYSFPDYYINWVRQA

PGQGLEWMGWIYFASGNSEYNQKFTGRVTMTRDTSSSTAYMELSSLRSEDTAVYFCASLY

DYDWYFDVWGQGTMVTVSS GGGGSGGGGSGGGGS DIVMTQTPLSLSVTPGEPASISCK

SSQSLVHSNGNTYLHWYLQKPGQSPQLLIYKVSNRFSGVPDRFSGSGSGADFTLKISRVEA

EDVGVYYCAETSHVPWTFGQGTKLEIK TTTPAPRPPTPAPTIASQPLSLRPEACRPAAGGA

VHTRGLDFACDIYIWAPLAGTCGVLLLSLVITLYCKRGRKKLLYIFKQPFMRPVQTTQEEDGC

SCRFPEEEEGGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLSTATKDTYDAL

HMQALPPR.
```

In a more preferred embodiment an anti-BCMA CAR of the invention comprises one of the sequence above which is humanized.

As used herein, the term "humanized" or "conservative sequence modifications" or "humanization" is intended to refer to amino acid modifications that do not significantly affect or alter the characteristics of the CAR (as compared to that of a CAR constructed using the original anti-BCMA antibody or anti-BCMA scFv) and/or that do not significantly affect the activity of the CAR containing the modified amino acid sequence and reduce or abolish a possible human anti-mouse antibody (HAMA) response.

The humanized CAR of the invention does not induce an immune response (in particular HAMA) directed against the CAR when expressed in the context of a primary T cell. Such conservative modifications include amino acid substitutions, additions and deletions in said antibody fragment in said CAR and/or any of the other parts of said CAR molecule. Modifications can be introduced into an antibody, into an antibody fragment or in any of the other parts of the CAR molecule of the invention by standard techniques known in the art, such as site-directed mutagenesis, PCR-mediated mutagenesis or by employing optimized germline sequences. Accordingly, the present invention provides a (humanized) BCMA CAR, wherein VH has at least 80% identity with SEQ ID NO 11 or SEQ ID NO 13, and VL has at least 80% identity with SEQ ID NO 12 or SEQ ID NO14.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested for the ability to bind BCMA using the functional assays described herein.

In one embodiment, the present invention provides a BCMA specific chimeric antigen receptor comprising:
- a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.
- a VH domain separated to a VL domain by a linker, said VH and VL contributing to the binding to BCMA; preferably said linker is a polypeptide of SEQ ID NO.10.
- a Hinge derived from Fcgamma (γ) RIIIalpha(α) having an amino acid sequence with at least 80%, more preferably at least 90%, 95% 97%, 99% or 100% sequence identity with the polypeptide of SEQ ID NO. 3;
- a transmembrane domain derived from CD8alpha(α) having an amino acid sequence with at least 90%, 91%, 92%, 93%, 94%, 95%, 96%, 97%, 98%, 99% or 100% identity with the polypeptide of SEQ ID NO. 6;

a co-stimulatory signal molecule derived from 4-1BB having an amino acid sequence with at least 70%, preferably at least 80%, more preferably at least 90%, 95% 97%, 99% or 100% sequence identity with an amino acid of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with amino acid of SEQ ID NO: 9;

In one embodiment, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, said VH and VL contributing to the binding to BCMA; preferably said linker is a polypeptide of SEQ ID NO.10.

a Hinge derived from Fcgamma (γ) RIIIalpha (α) having an amino acid sequence with at least 80%, more preferably at least 90%, 95% 97%; 99% or 100% sequence identity with the polypeptide of SEQ ID NO. 3;

a transmembrane domain (TM) derived from 4-1BB having an amino acid sequence with at least 90%, 91%, 92%, 93%, 94%, 95%, 96%, 97%, 98%, 99% or 100% identity with the polypeptide of SEQ ID NO. 7;

a co-stimulatory signal molecule derived from 4-1BB having an amino acid sequence with at least 70%, preferably at least 80%, more preferably at least 90%, 95% 97%, 99% or 100% sequence identity with an amino acid of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with an amino acid sequence of SEQ ID NO: 9.

In one embodiment, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, said VH and VL contributing to the binding to BCMA; preferably said linker is a polypeptide of SEQ ID NO.10.

a Hinge derived from human CD8 alpha chain having an amino acid sequence with at least 80%, more preferably at least 90%, 95% 97%, 98%, 99% or 100% sequence identity with the polypeptide of SEQ ID NO. 4;

a transmembrane domain derived from CD8alpha(α) having an amino acid sequence with at least 90%, 91%, 92%, 93%, 94%, 95%, 96%, 97%, 98%, 99% or 100% identity with the polypeptide of SEQ ID NO. 6;

a co-stimulatory signal molecule derived from 4-1BB having an amino acid sequence with at least 70%, preferably at least 80%, more preferably at least 90%, 95% 97%, 99% or 100% sequence identity with an amino acid sequence of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with an amino acid sequence of SEQ ID NO: 9;

In one embodiment, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, said VH and VL contributing to the binding to BCMA; preferably said linker is a polypeptide of SEQ ID NO.10.

a Hinge derived from human CD8 alpha chain having an amino acid sequence with at least 80%, more preferably at least 90%, 95% 97% 99% or 100% sequence identity with the polypeptide of SEQ ID NO. 4;

a transmembrane domain (TM) derived from 4-1BB having an amino acid sequence with at least 90%, 91%, 92%, 93%, 94%, 95%, 96%, 97%, 98%, 99% or 100% identity with the polypeptide of SEQ ID NO. 7;

a co-stimulatory signal molecule derived from 4-1BB having an amino acid sequence with at least 70%, preferably at least 80%, more preferably at least 90%, 95% 97%, 99% or 100% sequence identity with an amino acid sequence of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with an amino acid sequence of SEQ ID NO: 9.

In one embodiment, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, said VH and VL contributing to the binding to BCMA; preferably said linker is a polypeptide of SEQ ID NO.10.

a Hinge derived from IgG1 having an amino acid sequence with at least 80%, more preferably at least 90%, 95% 97% 99% or 100% sequence identity with the polypeptide of SEQ ID NO. 5;

a transmembrane domain derived from CD8alpha(α) having an amino acid sequence with at least 90%, 91%, 92%, 93%, 94%, 95%, 96%, 97%, 98%, 99% or 100% identity with the polypeptide of SEQ ID NO. 6;

a co-stimulatory signal molecule derived from 4-1BB having an amino acid sequence with at least 70%, preferably at least 80%, more preferably at least 90%, 95% 97%, 99% or 100% sequence identity with an amino acid sequence of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with an amino acid sequence of SEQ ID NO: 9;

In one embodiment, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, said VH and VL contributing to the binding to BCMA; preferably said linker is a polypeptide of SEQ ID NO.10.

a Hinge derived from IgG1 having an amino acid sequence with at least 80%, more preferably at least 90%, 95% 97% 99% or 100% sequence identity with the polypeptide of SEQ ID NO. 5;

a transmembrane domain (TM) derived from 4-1BB having an amino acid sequence with at least 90%, 91%, 92%, 93%, 94%, 95%, 96%, 97%, 98%, 99% or 100% identity with the polypeptide of SEQ ID NO. 7;

a co-stimulatory signal molecule derived from 4-1BB having an amino acid sequence with at least 70%, preferably at least 80%, more preferably at least 90%, 95% 97%, 99% or 100% sequence identity with an amino acid sequence of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with an amino acid sequence of SEQ ID NO: 9.

In a preferred embodiment, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, said VH and VL contributing to the binding to BCMA; preferably said linker is a polypeptide of SEQ ID NO.10.

a Hinge derived from Fcgamma (γ) RIIIalpha (α) having an amino acid sequence with at least 80%, more preferably at least 90%, 95% 97% 99% or 100% sequence identity with the polypeptide of SEQ ID NO. 3;

a transmembrane domain derived from CD8alpha(α) having an amino acid sequence with at least 90%, 91%, 92%, 93%, 94%, 95%, 96%, 97%, 98%, 99% or 100% identity with the polypeptide of SEQ ID NO. 6;

a co-stimulatory signal molecule derived from 4-1BB having an amino acid sequence with at least 70%, preferably at least 80%, more preferably at least 90%, 95% 97%, 99% or 100% sequence identity with an amino acid of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with amino acid of SEQ ID NO: 9;

In a more preferred embodiment, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, said VH and VL contributing to the binding to BCMA; preferably said linker is a polypeptide of SEQ ID NO.10.

a Hinge derived from IgG1 having an amino acid sequence with at least 80%, more preferably at least 90%. 95% 97% 99% or 100% sequence identity with the polypeptide of SEQ ID NO. 5;

a transmembrane domain derived from CD8alpha(α) having an amino acid sequence with at least 90%, 91%, 92%, 93%, 94%, 95%, 96%, 97%, 98%, 99% or 100% identity with the polypeptide of SEQ ID NO. 6;

a co-stimulatory signal molecule derived from 4-1BB having an amino acid sequence with at least 70%, preferably at least 80%, more preferably at least 90%, 95% 97%, 99% or 100% sequence identity with an amino acid sequence of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with an amino acid sequence of SEQ ID NO: 9;

In an even more preferred embodiment, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, said VH and VL contributing to the binding to BCMA; preferably said linker is a polypeptide of SEQ ID NO.10.

a Hinge derived from human CD8 alpha chain having an amino acid sequence with at least 80%, more preferably at least 90%, 95% 97%, 98%, 99% or 100% sequence identity with the polypeptide of SEQ ID NO. 4;

a transmembrane domain derived from CD8alpha having an amino acid sequence with at least 90%, 91%, 92%, 93%, 94%, 95%, 96%, 97%, 98%, 99% or 100% identity with the polypeptide of SEQ ID NO. 6;

a co-stimulatory signal molecule derived from 4-1BB having an amino acid sequence with at least 70%, preferably at least 80%, more preferably at least 90%, 95% 97%, 99% or 100% sequence identity with an amino acid sequence of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with an amino acid sequence of SEQ ID NO: 9;

In particular, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, preferably said linker is a polypeptide of SEQ ID NO.10, said VH and VL contributing to the binding to BCMA; said VH having an amino acid sequence with at least 80%, more preferably at least 90%, 95%, 97%, 99% or 100% sequence identity with the polypeptide of SEQ ID NO. 11, and said VL having an amino acid sequence with at least 80%, more preferably at least 90%, 95%, 97%, 99% or 100% sequence identity with the polypeptide of SEQ ID NO. 12 a Hinge derived from human CD8 alpha chain having an amino acid sequence with at least 80%, more preferably at least 90%, 95% 97%, 98%, 99% or 100% sequence identity with the polypeptide of SEQ ID NO. 4;

a transmembrane domain derived from CD8alpha(α) having an amino acid sequence with at least 90%, 91%, 92%, 93%, 94%, 95%, 96%, 97%, 98%, 99% or 100% identity with the polypeptide of SEQ ID NO. 6;

a co-stimulatory signal molecule derived from 4-1BB having an amino acid sequence with at least 70%, preferably at least 80%, more preferably at least 90%, 95% 97%, 99% or 100% sequence identity with an amino acid sequence of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with an amino acid sequence of SEQ ID NO: 9;

In particular, the present invention provides a BCMA specific chimeric antigen receptor comprising:

a optional signal peptide having an amino acid sequence with at least 80%, more preferably at least 90%, 95%, 97%, 99% or 100% sequence identity with the polypeptide of SEQ ID NO. 1 or 2; preferably the optional signal peptide has an amino acid sequence with at least 80%, more preferably at least 90%, 95%, 97%, 99% or 100% sequence identity with the polypeptide of SEQ ID NO 1. Preferably, the signal peptide is present.

a VH domain separated to a VL domain by a linker, preferably said linker is a polypeptide of SEQ ID NO.10, said VH and VL contributing to the binding to BCMA; said VH having an amino acid sequence with at least 80%, more preferably at least 90%, 95%, 97%, 99% or 100% sequence identity with the polypeptide of SEQ ID NO. 13, and said VL having an amino acid sequence with at least 80%, more preferably at least 90%, 95%, 97%, 99% or 100% sequence identity with the polypeptide of SEQ ID NO. 14 a Hinge derived from human CD8 alpha chain having an amino acid sequence with at least 80%, more preferably at least 90%, 95% 97%, 98%, 99% or 100% sequence identity with the polypeptide of SEQ ID NO. 4;

a transmembrane domain derived from CD8alpha(α) having an amino acid sequence with at least 90%, 91%, 92%, 93%, 94%, 95%, 96%, 97%, 98%, 99% or 100% identity with the polypeptide of SEQ ID NO. 6.

a co-stimulatory signal molecule derived from 4-1BB having an amino acid sequence with at least 70%, preferably at least 80%, more preferably at least 90%, 95% 97%, 99% or 100% sequence identity with an amino acid sequence of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with an amino acid sequence of SEQ ID NO: 9.

In one preferred embodiment, said CARs comprise a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 48, In one preferred embodiment, said CARs comprise a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO 50, In one preferred embodiment, said CARs comprise a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 52

In one preferred embodiment, said CARs comprise a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 54, In one preferred embodiment, said CARs comprise a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 56, In one preferred embodiment, said CARs comprise a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 58.

In a more preferred embodiment, said CARs comprise a polypeptide sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity with an amino acid sequence of SEQ ID NO: 50 or a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 56.

Human anti-BCMA antibodies (or scFv) can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

Polynucleotides, Vectors:

The present invention also relates to polynucleotides, vectors encoding the above described CAR according to the invention.

In one embodiment, the present invention provides polynucleotides, vectors encoding a BCMA CAR comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 48, In one preferred embodiment, the present invention provides polynucleotides, vectors encoding a BCMA CAR comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO 50, In one embodiment, the present invention provides polynucleotides, vectors encoding a BCMA CAR comprising a polypeptide sequence having at least 80%, 81%, 82%, 83%, 84%, 85%, 86%, 87%, 88%, 89%, 90%, 91%, 92%, 93%94%, 95%, 96%, 97%, 98%, 99% or 100% identity with an amino acid sequence of SEQ ID NO: 52.

In one embodiment, the present invention provides polynucleotides, vectors encoding a BCMA CAR comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 54, In one embodiment, the present invention provides polynucleotides, vectors encoding a BCMA CAR comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 56, In one embodiment, the present invention provides polynucleotides, vectors encoding a BCMA CAR comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 58.

In a more preferred embodiment, the present invention provides polynucleotides, vectors encoding a BCMA CAR comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 50 or polynucleotides, vectors encoding a BCMA CAR comprising polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 56.

The polynucleotides of this invention can be obtained using chemical synthesis, recombinant methods, or PCR.

Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

A polynucleotide encoding a BCMA specific CAR disclosed herein may exist in an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell). In some embodiments, a polynucleotide or vector can include a nucleic acid sequence encoding ribosomal skip sequences such as, for example without limitation, a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons [see (Donnelly and Elliott 2001; Atkins, Wills et al. 2007; Doronina, Wu et al. 2008)]. By "codon" is meant three nucleotides on an mRNA (or on the sense strand of a DNA molecule) that are translated by a ribosome into one amino acid residue. Thus, two polypeptides can be synthesized from a single, contiguous open reading frame within an imRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptides into the secretory pathway of a host cell, in some embodiments, a secretory signal sequence (also known as a leader sequence, prepro sequence or pre sequence) is provided in a polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5 to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830).

Those skilled in the art will recognize that, in view of the degeneracy of the genetic code, considerable sequence variation is possible among these polynucleotide molecules. In some embodiments, nucleic acid sequences of the invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the amino acid sequence SEQ ID NO: 1 and 2.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods of Engineering Immune Cells Endowed with CARs:

The present invention encompasses the method of preparing immune cells for immunotherapy comprising introducing ex-vivo into said immune cells the polynucleotides or vectors encoding one of the BCMA CAR as previously described.

In a preferred embodiment, said polynucleotides are included in lentiviral vectors in view of being stably expressed in the immune cells.

According to further embodiments, said method further comprises the step of genetically modifying said cell to make them more suitable for allogeneic transplantation.

According to a first aspect, the immune cell can be made less allogeneic, for instance, by inactivating at least one gene expressing one or more component of T-cell receptor (TCR) as described in WO 2013/176915, which can be combined with the inactivation of a gene encoding or regulating HLA or β2 m protein expression. Accordingly the risk of graft versus host syndrome and graft rejection is significantly reduced. In a preferred embodiment knock out TCR T cells are prepared by deleting said TCR by a method for engineering the immune cells described herein.

According to another aspect, the immune cells can be further genetically engineered to improve their resistance to immunosuppressive drugs or chemotherapy treatments, which are used as standard care for treating BCMA positive malignant cells. For instance, CD52 and glucocorticoid receptors (GR), which are drug targets of Campath (alemtuzumab) and glucocorticoids treatments, can be inactivated to make the cells resistant to these treatments and give them a competitive advantage over patient's own T-cells not endowed with specific BCMA CARs. Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblasic leukemia.

According to further aspect of the invention, the immune cells can be further manipulated to make them more active or limit exhaustion, by inactivating genes encoding proteins that act as "immune checkpoints" that act as regulators of T-cells activation, such as PDCD1 or CTLA-4. Examples of genes, which expression could be reduced or suppressed are indicated in Table 9.

TABLE 9

List of genes encoding immune checkpoint proteins.

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA (cd272) | BTLA |
| | CD160 (by55) | CD160 |
| | IgSF family | TIGIT |
| | | CD96 |
| | | CRTAM |
| | LAIR1 (cd305) | LAIR1 |
| | SIGLECs | SIGLEC7 |
| | | SIGLEC9 |
| | CD244 (2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL65T |
| Prevention of TCR signalling | | CSK, PAG1 SIT1 |
| Induced Treg Transcription factors controlling exhaustion | induced Treg transcription factors controlling exhaustion | FOXP3 PRDM1 (= blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

In a preferred embodiment said method of further engineering the immune cells involves introducing into said T cells polynucleotides, in particular mRNAs, encoding specific rare-cutting endonuclease to selectively inactivate the genes, as those mentioned above, by DNA cleavage. In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice for producing of the engineered immune cells on a large scale with a constant turn-over.

Expression of Drug Resistance Genes in Anti-BCMA CAR-Expressing Immune Cells

According to further aspects of the invention, the immune cells can be further manipulated to make them resistant to the most commonly used drugs or chemotherapy agents, for example cyclophosphamide (Cytoxan, Neosar), doxorubicin (Adriamycin), vincristine (Vincasar, Oncovin), or prednisone (multiple brand names).

Chemotherapy used as anti-cancer drugs are usually injected into a vein or taken by mouth. These drugs enter the bloodstream and reach almost all areas of the body, making this treatment very useful for lymphoma.

BCMA CAR T cells of the invention are further engineered to be able to survive and proliferate in the presence of said anticancer drugs.

In a particular embodiment, said drug resistance can be conferred to the T-cell by the expression of at least one drug resistance gene. Said drug resistance gene refers to a nucleic acid sequence that encodes "resistance" to an agent, such as a chemotherapeutic agent (e.g. methotrexate). In other words, the expression of the drug resistance gene in a cell permits proliferation of the cells in the presence of the agent to the same or greater extent than the proliferation of a corresponding cell without the drug resistance gene. The expression of the drug resistance gene in a cell permits proliferation of the cells in the presence of the agent and does not affect its activity. A drug resistance gene of the invention can encode resistance to anti-metabolite, methotrexate, vinblastine, cisplatin, alkylating agents, anthracyclines, cytotoxic antibiotics, anti-immunophilins, their analogs or derivatives, and the like.

Examples of such anti-cancer chemotherapy may be
An Alkylating agent selected from
    Cyclophosphamide (Cytoxan®)
    Chlorambucil
    Bendamustine (Treanda®)
    Ifosfamide (Ifex®), or a combination thereof
A Corticosteroid such as
    Prednisone or
    Dexamethasone (Decadron®)
A Platinum drug selected from
    Cisplatin
    Carboplatin
    Oxaliplatin, or combination thereof
A Purine analog selected from
    Fludarabine (Fludara®)
    Pentostatin (Nipent®)
    Cladribine (2-CdA, Leustatin®), or a combination thereof
An Anti-metabolites selected from
    Cytarabine (ara-C)
    Gemcitabine (Gemzar®)
    Methotrexate
    Pralatrexate (Folotyn®), or a combination thereof
Others drugs selected from
    Vincristine (Oncovin®)
    Doxorubicin (Adriamycin®)
    Mitoxantrone
    Etoposide (VP-16)
    Bleomycin, or a combination thereof For this purpose the present invention provides a method comprising the following step:
    (i) at least gene(s) conferring resistance to a said drug or to several drugs is introduced into BCMA CAR T cells or
    (ii) the expression of at least one gene (conferring sensitivity or resistance) is inhibited or increased into BCMA CAR T cells.

In one embodiment, a drug resistance gene of the invention can confer resistance to a drug (or an agent), in particular an anti-cancer drug selected from Aracytine, Cytosine Arabinoside, amsacrine, Daunorubicine, Idarubicine, Novantrone, Mitoxantrone, Vepeside, Etoposide (VP16), arsenic trioxyde, transretinoic acid, combination of arsenic trioxyde, transretinoic acid, mechlorethamine, procarbazine, chlorambucil, cytarabine, anthracyclines, 6-thioguanine, hydroxyurea, prednisone, and combination thereof.

Several drug resistance genes have been identified that can potentially be used to confer drug resistance to anti-BCMA CAR T cells of the invention (Takebe, Zhao et al. 2001; Sugimoto, Tsukahara et al. 2003; Zielske, Reese et al. 2003; Nivens, Felder et al. 2004; Bardenheuer, Lehmberg et al. 2005; Kushman, Kabler et al. 2007).

One example of drug resistance gene can also be a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance gene according to the present invention can be a nucleic acid sequence encoding a mutant form of human wild type DHFR (GenBank: AAH71996.1) which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 (Schweitzer, Dicker et al. 1990); International application WO94/24277; U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide set forth in GenBank: AAH71996.1. In a particular embodiment, the serine residue at position 15 is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

As used herein, "antifolate agent" or "folate analogs" refers to a molecule directed to interfere with the folate metabolic pathway at some level. Examples of antifolate agents include, e.g., methotrexate (MTX); aminopterin; trimetrexate (Neutrexin); edatrexate; N10-propargyl-5,8-dideazafolic acid (CB3717); ZD1694 (Tumodex), 5,8-dideazaisofolic acid (IAHQ); 5,10-dideazatetrahydrofolic acid (DDATHF); 5-deazafolic acid; PT523 (N alpha-(4-amino-4-deoxypteroyl)-N delta-hemiphthaloyl-L-ornithine); 10-ethyl-10-deazaaminopterin (DDATHF, lomatrexol); piritrexim; 10-EDAM; ZD1694; GW1843; Pemetrexate and PDX (10-propargyl-10-deazaaminopterin).

Another example of drug resistance gene can also be a mutant or modified form of ionisine-5'-monophosphate dehydrogenase II (IMPDH2), a rate-limiting enzyme in the de novo synthesis of guanosine nucleotides. The mutant or modified form of IMPDH2 is an IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (NP_000875.2) that lead to a significantly increased resistance to IMPDH inhibitor. The mutations are preferably at positions T333 and/or S351 (Yam, Jensen et al. 2006; Sangiolo, Lesnikova et al. 2007; Jonnalagadda, Brown et al. 2013). In a particular embodiment, the threonine residue at position 333 is replaced with an isoleucine residue and the serine residue at position 351 is replaced with a tyrosine residue. Correspondence of amino acid positions described herein is frequently expressed in terms of the positions of the amino acids of the form of wild-type human IMPDH2 polypeptide set forth in NP_000875.2.

Another drug resistance gene is the mutant form of calcineurin. Calcineurin (PP2B), an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin, Mancao et al. 2009). The drug resistance gene of the present invention can be a nucleic acid sequence encoding a mutant form of calcineurin resistant to calcineurin inhibitor such as FK506 and/or CsA. In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagines residue, the leucine at position 354 can be replaced with an alanine residue; the lysine at position 360 can be replaced with an alanine or phenylalanine residue of a sequence corresponding to GenBank: ACX34092.1. Correspondence of amino acid positions described herein is frequently expressed in terms of the positions of the amino acids of the form of wild-type human calcineurin heterodimer a polypeptide set forth in (GenBank: ACX34092.1).

In another particular embodiment, said mutant form can comprise at least one mutated amino acid of the wild type calcineurin heterodimer bat positions: V120, N123, L124 or K125, preferably double mutations at positions L124 and K125. In a particular embodiment, the valine at position 120 can be replaced with a serine, an aspartic acid, phenylalanine or leucine residue; the asparagine at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence corresponding to GenBank: ACX34095.1. Correspondence of amino acid positions described herein is frequently expressed in terms of the positions of the amino acids of the form of wild-type human calcineurin heterodimer b polypeptide set forth in (Gen-Bank: ACX34095.1).

Another example of drug resistance gene is 0(6)-methyl-guanine methyltransferase (MGMT) encoding human alkyl guanine transferase (hAGT). ACT is a DNA repair protein that confers resistance to the cytotoxic effects of alkylating agents, such as nitrosoureas and temozolomide (TMZ). 6-benzylguanine (6-BG) is an inhibitor of ACT that potentiates nitrosourea toxicity and is co-administered with TMZ to potentiate the cytotoxic effects of this agent. Several mutant forms of MGMT that encode variants of ACT are highly resistant to inactivation by 6-BG, but retain their ability to repair DNA damage (Maze, Kurpad et al. 1999). In a particular embodiment, ACT mutant form can comprise a mutated amino acid of the wild type ACT position P140, in the amino acid sequence SEQ ID NO: 18 (UniProtKB: P16455). In a preferred embodiment, said proline at position 140 is replaced with a lysine residue.

Another example of drug resistance gene is multidrug resistance protein 1 (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents.

Overexpressing multidrug resistance protein 1 has been described to confer resistance to drugs such as Mitoxantrone (Charles S. Morrow, Christina Peklak-Scott, Bimjhana Bishwokarma, Timothy E. Kute, Pamela K. Smitherman, and Alan J. Townsend. Multidrug Resistance Protein 1 (MRP1, ABCC1) Mediates Resistance to Mitoxantrone via Glutathione-Dependent Drug Efflux *Mol Pharmacol* April 2006 69:1499-1505).

Thus, drug resistance can be conferred to anti-BCMA CAR T cells of the invention by enhancing the expression of nucleic acid sequence that encodes MDR-1 (NP_000918).

Still another way of preparing drug resistant cells is to prepare cells with specific mutation (s) such as mutations at Arg486 and Glu571 in the Human Topoisomerase II gene, to confer resistance to amsacrine (S. PATEL, B. A. KELLER, and L. M. FISHER. 2000. MOLECULAR PHARMACOLOGY. Vol 57: p 784-791 (2000).

Still another way of preparing drug resistant cells is to prepare cells overexpressing microRNA-21 to confer resistance to daunorubicine (Involvement of miR-21 in resistance to daunorubicin by regulating PTEN expression in the leukaemia K562 cell line Bai, Haitao et al. FEBS Letters, Volume 585, Issue 2, 402-408).

Drug resistance gene can also confer resistance to cytotoxic antibiotics, and can be ble gene or mcrA gene. Ectopic expression of ble gene or mcrA in an immune cell gives a selective advantage when exposed to the chemotherapeutic agent, respectively the bleomycine or the mitomycin C.

A very practical approach to gene therapy is the addition of a gene to engineer T-cell by using efficient gene delivery with vectors, preferably viral vector. Thus, in a particular embodiment, said drug resistance gene can be expressed in the cell by introducing a transgene preferably encoded by at least one vector into a cell.

In one embodiment, cells bearing a drug resistance gene or a modified gene conferring resistance to a drug also comprise an inducible suicide gene—the induction of which provokes cell death—allowing their selective destruction.

The random insertion of genes into the genome may lead to the inappropriate expression of the inserted gene or the gene near the insertion site. Specific gene therapy using homologous recombination of exogenous nucleic acid comprising endogenous sequences to target genes to specific sites within the genome can allow engineering secure T-cells. As described above, the genetic modification step of the method can comprise a step of introduction into cells of an exogenous nucleic acid comprising at least a sequence encoding the drug resistance gene and a portion of an endogenous gene such that homologous recombination occurs between the endogenous gene and the exogenous nucleic acid. In a particular embodiment, said endogenous gene can be the wild type "drug resistance" gene, such that after homologous recombination, the wild type gene is replaced by the mutant form of the gene which confers resistance to the drug.

Endonucleolytic breaks are known to stimulate the rate of homologous recombination. Thus, in a particular embodiment, the method of the invention further comprises the step of expressing in the cell a rare-cutting endonuclease which is able to cleave a target sequence within an endogenous gene. Said endogenous gene can encode for examples DHFR, IMPDH2, calcineurin or ACT. Said rare-cutting endonuclease can be a TALE-nuclease, a Zinc finger nuclease, a CRISPR/Cas9 endonuclease, a MBBBD-nuclease or a meganuclease.

Inactivation of Drug Sensitizing Genes in Anti-BCMA CAR-Expressing Immune Cells

In another particular embodiment, said drug resistance can be conferred to the cell of the invention, anti-BCMA CAR expressing immune cell, by the inactivation of a drug sensitizing gene.

The inventor sought to inactivate potential drug sensitizing gene to engineer T-cell for immunotherapy, in particular to engineer anti-BCMA CAR expressing immune cell that can be used in combination with a therapeutic agent (anti-cancer drug).

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. In a particular embodiment, the step of inactivating at least one drug sensitizing gene comprises introducing into the cell a rare-cutting endonuclease able to disrupt at least one drug sensitizing gene. In a more particular embodiment, said cells are transformed with nucleic acid encoding a rare-cutting endonuclease capable of disrupting a drug sensitizing gene, and said rare-cutting endonuclease is expressed into said cells. Said rare-cutting endonuclease can be a meganuclease, a Zinc finger nuclease, CRISPR/Cas9 nuclease, A MBBBD-nuclease or a TALE-nuclease. In a preferred embodiment, said rare-cutting endonuclease is a TALE-nuclease.

In a preferred embodiment, drug sensitizing gene which can be inactivated to confer drug resistance to the T-cell is the human deoxycytidine kinase (dCK) gene. This enzyme is required for the phosphorylation of the deoxyribonucleosides deoxycytidine (dC), deoxyguanosine (dG) and deoxyadenosine (dA). Purine nucleotide analogs (PNAs) are metabolized by dCK into mono-, di- and tri-phosphate PNA. Their triphosphate forms and particularly clofarabine triphosphate compete with ATP for DNA synthesis, acts as proapoptotic agent and are potent inhibitors of ribonucleotide reductase (RNR) which is involved in trinucleotide production.

Preferably, the inactivation of dCK in T cells is mediated by TALE nuclease. To achieve this goal, several pairs of dCK TALE-nuclease have been designed, assembled at the polynucleotide level and validated by sequencing. Examples of TALE-nuclease pairs which can be used according to the invention are depicted in PCT/EP2014/075317.

This dCK inactivation in T cells confers resistance to purine nucleoside analogs (PNAs) such as clofarabine and fludarabine.

In another preferred embodiment, the dCK inactivation in T cells is combined with an inactivation of TRAC genes rendering these double knock out (KO) T cells both resistant to drug such as clofarabine and less allogeneic. This double features is particularly useful for a therapeutic goal, allowing "off-the-shelf" allogeneic cells for immunotherapy in conjunction with chemotherapy to treat patients with cancer. This double KO inactivation dCK/TRAC can be performed simultaneously or sequentially. One example of TALE-nuclease dCK/TRAC pairs which gave success in the invention is described in PCT/EP2014/075317, in particular, the target sequences in the 2 loci (dCK and TRAC).

Another example of enzyme which can be inactivated is human hypoxanthine-guanine phosphoribosyl transferase (HPRT) gene (Genbank: M26434.1). In particular HPRT can be inactivated in engineered T-cells to confer resistance to a cytostatic metabolite, the 6-thioguanine (6TG) which is converted by HPRT to cytotoxic thioguanine nucleotide and which is currently used to treat patients with cancer, in particular leukemias (Hacke, Treger et al. 2013). Guanines analogs are metabolized by HPRT transferase that catalyzes addition of phosphoribosyl moiety and enables the formation of TGMP Guanine analogues including 6 mercapthopurine (6MP) and 6 thioguanine (6TG) are usually used as lymphodepleting drugs to treat ALL. They are metabolized by HPRT (hypoxanthine phosphoribosyl transferase that catalyzes addition of phosphoribosyl moiety and enables formation TGMP. Their subsequent phosphorylations lead to the formation of their triphosphorylated forms that are eventually integrated into DNA. Once incorporated into DNA, thio GTP impairs fidelity of DNA replication via its thiolate groupment and generate random point mutation that are highly deleterious for cell integrity.

In another embodiment, the inactivation of the CD3 normally expressed at the surface of the T-cell can confer resistance to anti-CD3 antibodies such as teplizumab.

The terms "therapeutic agent", "chemotherapeutic agent", or "drug" or "anti-cancer drug" as used herein refers to a medicament, preferably a compound or a derivative thereof that can interact with a cancer cell, thereby reducing the proliferative status of the cell and/or killing the cell. Examples of chemotherapeutic agents or "anti-cancer drug" include, but are not limited to, alkylating agents (e.g. Busulfan•Carboplatine•Chlorambucil•Cisplatine•Cyclophosphamide•Ifosfamide•Melphalan•Mechlorethamine•Oxaliplatine•Uramustine•Temozolomide•Fotemustine), metabolic antagonists (e.g., purine nucleoside antimetabolite such as clofarabine, fludarabine or 2'-deoxyadenosine, methotrexate (MTX), 5-fluorouracil or derivatives thereof, Azathioprine•Capecitabine•Cytarabine•Floxuridine•Fluorouracile•Gemcitabine•Methotrexate•Pemetrexed), antitumor antibiotics (e.g., mitomycin, Adriamycin, Bleomycine•Daunorubicine•Doxorubicine•Epirubicine•Hydroxyurea•Idarubicine•Mitomycin C•Mitoxantrone), plant-derived antitumor agents (e.g., vincristine, vindesine, Taxol, Vinblastine•(Vinorelbine)•Docetaxel•Paclitaxel), topoisomerase inhibitor (Irinotecan•Topotecan•Etoposide), In a preferred embodiment, a therapeutic agent, a chemotherapy drug as used herein refers to a compound or a derivative thereof that may be used to treat cancer, in particular to treat a hematopoietic cancer cell and more particularly AML, thereby reducing the proliferative status of the cancer cell and/or killing the cancer cell. Examples of chemotherapeutic agents include, but are not limited to Aracytine, Cytosine Arabinoside, Amsacrine, Daunorubicine, Idarubicine, Novantrone, Mitoxantrone, Vepeside, Etoposide (VP16), arsenic trioxyde, transretinoic acid, mechlorethamine, procarbazine, chlorambucil, and combination thereof.

In other embodiments of the present invention, cells of the invention are administered to a patient in conjunction with a drug (or an agent) selected from Aracytine, Cytosine Arabinoside, amsacrine, Daunorubicine, Idarubicine, Novantrone, Mitoxantrone, Vepeside, Etoposide (VP16), arsenic trioxyde, transretinoic acid, cytarabine, anthracyclines, 6-thioguanine, hydroxyurea, prednisone, and combination thereof.

Such agents may further include, but are not limited to, the anti-cancer agents TRIMETHOTRIXATE (TMTX), TEMOZOLOMIDE, RALTRITREXED, S-(4-Nitrobenzyl)-6-thioinosine (NBMPR), 6-benzyguanidine (6-BG), bis-chloronitrosourea (BCNU) and CAMPTOTHECIN, or a therapeutic derivative of any thereof.

In a more preferred embodiment an anti-BCMA CAR of SEQ ID No. 50 or of SEQ ID No. 56 expressing T cell, is administered to a patient, in combination with at least one therapeutic agent selected from Aracytine, Cytosine Arabinoside, Amsacrine, Daunorubicine, Idarubicine, Novantrone, Mitoxantrone, Vepeside, Etoposide (VP16), arsenic trioxyde, transretinoic acid and combination thereof.

As used herein, a cell which is "resistant or tolerant" to an agent means a cell which has been genetically modified so that the cell proliferates in the presence of an amount of an agent that inhibits or prevents proliferation of a cell without the modification.

Preparing Multiple Drug Resistant Anti-BCMA CAR-Expressing Immune Cells

In another particular embodiment, the inventors sought to develop an "off-the shelf" immunotherapy strategy, using allogeneic T-cells, in particular allogenic anti-BCMA CAR expressing T-cell resistant to multiple drugs to mediate selection of engineered T-cells when the patient is treated with different drugs. The therapeutic efficiency can be significantly enhanced by genetically engineering multiple drug resistance allogeneic T-cells. Such a strategy can be particularly effective in treating tumors that respond to drug combinations that exhibit synergistic effects. Moreover multiple resistant engineered T-cells can expand and be selected using minimal dose of drug agents.

Thus, the method according to the present invention can comprise modifying T-cell to confer multiple drug resistance to said T-cell. Said multiple drug resistance can be conferred by either expressing more than one drug resistance gene or by inactivating more than one drug sensitizing gene. In another particular embodiment, the multiple drug resistance can be conferred to said T-cell by expressing at least one drug resistance gene and inactivating at least one drug sensitizing gene. In particular, the multiple drug resistance can be conferred to said T-cell by expressing at least one drug resistance gene such as mutant form of DHFR, mutant form of IMPDH2, mutant form of calcineurin, mutant form of MGMT, the ble gene, and the mcrA gene and inactivating at least one drug sensitizing gene such as HPRT gene. In a preferred embodiment, multiple drug resistance can be conferred by inactivating HPRT gene and expressing a mutant form of DHFR; or by inactivating HPRT gene and expressing a mutant form of IMPDH2; or by inactivating HPRT gene and expressing a mutant form of calcineurin; by inactivating HPRT gene and expressing a mutant form of MGMT; by inactivating HPRT gene and expressing the ble gene; by inactivating HPRT gene and expressing the mcrA gene.

In one embodiment, the present invention provides anti-BCMA CAR expressing T-cell wherein TCR expression is affected and which is expressing more than one drug resistance gene and/or wherein more than one drug sensitizing gene is inactivated.

Suicide Genes in Anti-BCMA CAR-Expressing Immune Cells

In one embodiment, a suicide polypeptide may be expressed at the surface of a CAR-T cell of the invention (TCR KO and resistant to at least on anticancer chemotherapy); binding of rituximab to the R epitopes of the polypeptide causes lysis of the cell. Thus, the suicide polypeptide may comprise a signal peptide at the amino terminus. More than one molecule of rituximab may bind per polypeptide expressed at the cell surface. Each R epitope of the polypeptide may bind a separate molecule of rituximab. Deletion of BCMA specific CAR-T cells may occur in vivo, for example by administering rituximab to a patient. The decision to delete the transferred cells may arise from undesirable effects being detected in the patient which are attributable to the transferred cells, such as for example, when unacceptable levels of toxicity are detected.

In some instances, since engineered T-cells can expand and persist for years after administration, it can be desirable to include a safety mechanism to allow selective deletion of administrated T-cells. Thus, in some embodiments, the method of the invention can comprises the transformation of said T-cells with a recombinant suicide gene. Said recombinant suicide gene is used to reduce the risk of direct toxicity and/or uncontrolled proliferation of said T-cells once administrated in a subject (Quintarelli C, Vera F, blood 2007; Tey S K, Dotti G., Rooney C M, boil blood marrow transplant 2007). Suicide genes enable selective deletion of transformed cells in vivo. In particular, the suicide gene has the ability to convert a non-toxic pro-drug into cytotoxic drug or to express the toxic gene expression product. In other words, "Suicide gene" is a nucleic acid coding for a product, wherein the product causes cell death by itself or in the presence of other compounds.

A representative example of such a suicide gene is one which codes for thymidine kinase of herpes simplex virus. Additional examples are thymidine kinase of varicella zoster virus and the bacterial gene cytosine deaminase which can convert 5-fluorocytosine to the highly toxic compound 5-fluorouracil. Suicide genes also include as non limiting examples caspase-9 or caspase-8 or cytosine deaminase. Caspase-9 can be activated using a specific chemical inducer of dimerization (CID). Suicide genes can also be polypeptides that are expressed at the surface of the cell and can make the cells sensitive to therapeutic monoclonal antibodies. As used herein "prodrug" means any compound useful in the methods of the present invention that can be converted to a toxic product. The prodrug is converted to a toxic product by the gene product of the suicide gene in the method of the present invention. A representative example of such a prodrug is ganciclovir which is converted in vivo to a toxic compound by HSV-thymidine kinase. The ganciclovir derivative subsequently is toxic to tumor cells. Other representative examples of prodrugs include acyclovir, FIAU [1-(2-deoxy-2-fluoro-β-D-arabinofuranosyI)-5-iodouracil], 6-methoxypurine arabinoside for VZV-TK, and 5-fluorocytosine for cytosine deaminase.

One preferred suicide gene system employs a recombinant antigenic polypeptide comprising antigenic motif recognized by the anti-CD20 mAb Rituximab, especially QBen10, such as in the so-called RQR8 polypeptide described in WO2013153391. Rituximab, an authorized antibody drug, can then be used for cell depletion when needed.

In one embodiment, the present invention provides allogenic anti-BCMA CAR expressing T-cell expressing more than one drug resistance gene or wherein more than one drug sensitizing gene is inactivated, and a suicide gene, preferably RQR8 allowing said cells to be destroyed.

The suicide gene expression may be inducible for example by doxycyclin-such as in Cenlivre M et al., 2014; Gene Therapy (2010) 17: 14-25 adapted to human cells.

The present invention provides an anti-BCMA CAR-T cells comprising the polynucleotide encoding a polypeptide having at least 80% identity with a polypeptide comprising SEQ ID NO 50 or SEQ ID NO 56, the suicide polypeptide is expressed at the surface of a CAR-T cell. In some embodiments, the suicide polypeptide comprises the amino acid sequence shown in (SEQ ID NO. 60).

In one preferred embodiment a suicide gene is introduced into BCMA CAR T cells, in particular a RQR8 gene See, e.g., WO2013153391A, which is hereby incorporated by reference in its entirety.

Clofarabine Resistant Anti-BCMA CAR-Expressing Immune Cells

The invention encompasses the manufacture of T cells for therapeutic use with a deficient TCR, which are resistant to a drug such as to Clofarabine. They can be obtained by inactivation of the dCK gene such as previously explained. According to a preferred embodiment, the T-cells are made resistant to chemotherapy and less allogeneic by combining inactivation of dCK and TCR genes as described above.

Thus, the present invention provides an anti-BCMA CAR expressing cell, in particular an anti-BCMA CAR expressing T cell wherein the CAR is derived from BC30 or BC50 (comprising a SEQ ID N050 or SEQ ID NO. 56, optionally humanized) and wherein the dCK gene is inactivated.

BCMA+/luc+ drug resistant H929 cells for testing the cytotoxicity of drug resistant allogenic CAR T cells The present invention encompasses also a method for manufacturing target cells which express both a surface receptor specific to the CAR T cells and a resistance gene. These target cells are particularly useful for testing the cytotoxicity of CAR T cells. These cells are readily resistant to clinically relevant dose of clofarabine and harbor luciferase activity. This combination of features enable traking them in vivo in a mice model or destroy them when required.

More particularly, they can be used to assess the cytotoxicity properties drug resistant T cells in mice in the presence of clofarabine or other PNAs. Clofarabine resistant H929 cells mimick the physiological state of acute lymphoblastic leukemia (ALL) patients relapsing form induction therapy, that harbor drug resistant B cell malignancies. Thus, these cells are of great interest to evaluate the reliability and cytotoxicity of drug resistant CAR T cells. Preferably, these target cells are BCMA+ Luciferase+ H929 cells.

Isolated Cell

The present invention relates to an isolated cell expressing a CAR of the invention which binds to BCMA. Thus, the invention relates to an isolated anti-BCMA CAR expressing cell. In a particular embodiment, said anti-BCMA CAR expressing cell is resistant to at least one drug and is endowed with a suicide gene and/or comprises at least one disrupted gene encoding a T-cell receptor component.

In a preferred embodiment, said anti-BCMA CAR T-cell expresses at least one drug resistance gene, preferably ble gene or mcrA gene or gene encoding a mutant DHFR, a mutant IMPDH2, a mutant ACT or a mutant calcineurin.

In another particular embodiment, said anti-BCMA CAR expressing T cell comprises at least one disrupted drug sensitizing gene such as dCK or HPRT gene. In a more particular embodiment, said isolated anti-BCMA CAR T-cell comprises a disrupted HPRT gene and express a DHFR mutant; said isolated anti-BCMA CAR T-cell comprises a disrupted HPRT gene and express a IMPDH2 mutant; said isolated anti-BCMA CAR T-cell comprises a disrupted HPRT gene and express a calcineurin mutant; said isolated anti-BCMA CAR T-cell comprises a disrupted HPRT gene and express a ACT mutant.

Anti-BCMA CAR T-Cell Resistant to a Drug for its Use in Immunotherapy

In particular, the present invention relates to an allogeneic TCR KO T-cell, in particular an TCR KO allogeneic anti-BCMA CAR expressing T-cell, and preferably a TCR KO allogeneic anti-BCMA CAR expressing T-cell comprising a peptide having 80% to 100% identity with scfv from BC 30 or BC 50, said allogeneic anti-BCMA CAR expressing T-cell comprising a peptide having 80% to 100% identity with scfv from BC30 or BC50 is more particularly resistant to a drug, and specifically suitable for immunotherapy.

In a preferred embodiment, said TCR KO allogeneic anti-BCMA CAR expressing T-cell comprises a peptide having 80% to 100% identity with SEQ ID NO.50 or 56 and is more particularly resistant to a drug, and specifically suitable for immunotherapy.

In one embodiment, the present invention provides a composition comprising said anti-BCMA CAR expressing cells, said composition comprising said anti-BCMA CAR expressing T cell of the invention, preferably said anti-BCMA CAR is of SEQ ID NO. 50 or of SEQ ID NO. 56, preferably humanized and at least one drug cited as anti-cancer or anti inflammatory disease chemotherapy.

The resistance of a drug can be conferred by inactivation of drug sensitizing genes or by expression of drug resistance genes. Some examples of drugs which suit to the invention are chemotherapy such as Melphalan, Vincristine (Oncovin®), Cyclophosphamide (Cytoxan®), Etoposide (VP-16), Doxorubicin (Adriamycin®), Liposomal doxorubicin (Doxil®), Bendamustine (Treanda®), Corticosteroids such as dexamethasone and prednisone.

Immunomodulating agents such as
Thalidomide (Thalomid®) Lenalidomide (Revlimid®) Pomalidomide (Pomalyst®)
Proteasome inhibitors such as
Bortezomib (Velcade®), Carfilzomib (Kyprolis®)
Histone deacetylase (HDAC) inhibitors such as Panobinostat (Farydak®)
Examples of combination drugs used with the anti-BCMA CAR T cells of the invention may be the following:
  Melphalan and prednisone (MP), with or without thalidomide or bortezomib,
  Vincristine, doxorubicin (Adriamycin), and dexamethasone,
  Thalidomide (or lenalidomide) and dexamethasone,
  Bortezomib, doxorubicin, and dexamethasone,
  Bortezomib, dexamethasone, and thalidomide (or lenalidomide),
  Liposomel doxorubicin, vincristine, dexamethasone,
  Carfilzomib, lenalidomide, and dexamethasone,
  Dexamethasone, cyclophosphamide, etoposide, and cisplatin (called DCEP),
  Dexamethasone, thalidomide, cisplatin, doxorubicin, cyclophosphamide, and etoposide (called DT-PACE), with or without bortezomib,
  Panobinostat, bortezomib, and dexamethasone.

In one aspect, the present invention provides methods for engineering immune cells to make them resistant to purine nucleotide analogs (PNA), such a clorofarabine or fludarabine, so that they can be used in cancer immunotherapy treatments in patients pre-treated with these conventional chemotherapies or combinations of chemotherapies.

The resistance to drugs can be conferred to the T-cells by inactivating one or more gene(s) responsible for the cell's sensitivity to the drug (drug sensitizing gene(s), such as the dcK and/or HPRT genes.

According to another aspect, the resistance to drugs can be conferred to an anti-BCMA T-cell by expressing a drug resistance gene. Variant alleles of several genes such as dihydrofolate reductase (DHFR), inosine monophosphate dehydrogenase 2 (IMPDH2), calcineurin or methylguanine transferase (MGMT) have been identified to confer drug resistance to a cell according to the invention.

For instance, CD52 and glucocorticoid receptors (GR), which are drug targets of Campath (alemtuzumab) or rituximab and glucocorticoids treatments, can be inactivated to make the cells resistant to these treatments and give them a competitive advantage over patient's own T-cells not endowed with specific BCMA CARs. Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of multiple myeloma.

According to further aspect of the invention, the immune cells can be further manipulated to make them more active or limit exhaustion, by inactivating genes encoding proteins that act as "immune checkpoints" that act as regulators of T-cells activation, such as the following gene selected from CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL65T, CSK, PAG1, SIT1, FOXP3, PRDM1 (orblimp1), BATF, GUCY1A2, GUCY1A3, GUCY1B2, GUCY1B3, preferably, said gene is PDCD1 or CTLA-4. Examples of genes, which expression could be reduced or suppressed are indicated in Table 9.

In one embodiment said gene is a gene that acts as a regulator of T-cells activation coding the beta 2 microglobulin protein.

According to a further aspect of the invention, the anti-BCMA CAR-immune cells of the invention can be further manipulated to make them resistant to a drug, in particular to a drug used during chemotherapy against cancer, in particular a BCMA-expressing cell-mediated cancer such as AML. This can be achieved by introducing a gene conferring resistance to said drug. This same gene may be turned on and off by using a gene inducible inhibition/expression system as previously described (Garcia E L, Mills A A (2002) Getting around lethality with inducible Cre-mediated excision. Semin Cell Dev Biol 13:151-8, Lewandoski M (2001) Conditional control of gene expression in the mouse. Nat Rev Genet 2:743-55; Scharfenberger L, Hennerici T, Kirly G et al. (2014) Transgenic mouse technology in skin biology: Generation of complete or tissue-specific knockout mice. J. Invest Dermatol 134:e16; Schwenk F, Kuhn R, Angrand P O et al. (1998) Temporally and spatially regulated somatic mutagenesis in mice. Nucleic Acids Res 26:1427-32

Thus, anti-BCMA CAR-expressing drug resistant immune cell, wherein (i) at least one gene expressing one or more component of T-cell receptor (TCR) is inactivated (ii) at least one gene conferring resistance to a drug is incorporated or a gene conferring sensitivity to said drug is deleted or mutated to be inactivated (iii) optionally another gene selected from the gene disclosed in table 9 is inactivated—is an object of the present invention.

The present invention encompasses the isolated anti-BCMA CAR-immune cells or cell lines obtainable by the method of the invention, more particularly isolated cells comprising any of the proteins, polypeptides, allelic variants, altered or deleted genes or vectors described herein.

The immune cells of the present invention or cell lines can further comprise exogenous recombinant polynucleotides, in particular CARs or suicide genes or they can comprise altered or deleted genes coding for checkpoint proteins or ligands thereof that contribute to their efficiency as a therapeutic product, ideally as an "off the shelf" product. In another aspect, the present invention concerns the method for treating or preventing cancer in the patient by administrating at least once an engineered immune cell obtainable by the above methods.

Delivery Methods

The different methods described above involve introducing CAR into a cell. As non-limiting example, said CAR can be introduced as transgenes encoded by one plasmid vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Engineered Immune Cells

The present invention encompasses the method of preparing immune cells for immunotherapy comprising introducing ex-vivo into said immune cells the polynucleotides or vectors encoding the BCMA CAR of the invention. A method of preparing immune cells for immunotherapy is described in WO2014/130635, WO2013176916, WO2013176915 and incorporated herein by reference.

Similarly, possible individual steps for preparing engineered immune cells are disclosed in patents Nos. WO/2014/039523, WO/2014/184741, WO/2014/191128, WO/2014/184744, and WO/2014/184143, and incorporated herein by reference.

The present invention also relates to isolated cells or cell lines susceptible to be obtained by said method to engineer cells. In particular said isolated cell comprises at least one CAR as described above. In another embodiment, said isolated cell comprises a population of CARs each one comprising different extracellular ligand binding domains. In particular, said isolated cell comprises exogenous polynucleotide sequence encoding CAR. Genetically modified immune cells of the present invention are activated and proliferate independently of antigen binding mechanisms.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptive immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

As a preferred embodiment, the present invention provides T-cells or a population of T-cells endowed with a BCMA CAR as described above, that do not express functional TCR and that a reactive towards BCMA positive cells, for their allogeneic transplantation into patients.

As a more preferred embodiment, the present invention provides T-cells or a population of T-cells endowed with a BCMA CAR as described above, that are further resistant to at least one drug used for the treatment of BCMA-expressing cancer cell and/or a suicide gene such as RQR8, for their allogeneic transplantation into patients.

In one embodiment the present invention provides T-cells or a population of T-cells endowed with a BCMA CAR as described above comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 48.

In one preferred embodiment, the present invention provides T-cells or a population of T-cells endowed with a BCMA CAR as described above comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO 50.

In one embodiment, the present invention provides T-cells or a population of T-cells endowed with a BCMA CAR as described above comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 52.

In one embodiment, the present invention provides T-cells or a population of T-cells endowed with a BCMA CAR as described above comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 54.

In one preferred embodiment, In one embodiment, the present invention provides T-cells or a population of T-cells as described above endowed with a BCMA CAR comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 56.

In one embodiment, the present invention provides T-cells or a population of T-cells endowed with a BCMA CAR as described above comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 58.

In a more preferred embodiment, the present invention provides T-cells or a population of T-cells endowed with a BCMA CAR as described above comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 50 or comprising a polypeptide sequence having at least 80%, 81%, 82%, 83%, 84%, 85%, 86%, 87%, 88%, 89%, 90%, 91%, 92%, 93% 94%, 95%, 96%, 97%, 98%, 99% or 100% identity with an amino acid sequence of SEQ ID NO: 56.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, -10, -2, IL-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics.

In another particular embodiment, said cells can be expanded by co-culturing with tissue or cells. Said cells can also be expanded in vivo, for example in the subject's blood after administrating said cell into the subject.

Therapeutic Applications

In another embodiment, isolated cell obtained by the different methods or cell line derived from said isolated cell as previously described can be used as a medicament. In another embodiment, said medicament can be used for treating cancer, particularly for the treatment of B-cell lymphomas and leukemia in a patient in need thereof. In another embodiment, said isolated cell according to the invention or cell line derived from said isolated cell can be used in the manufacture of a medicament for treatment of a cancer in a patient in need thereof.

In another aspect, the present invention relies on methods for treating patients in need thereof, said method comprising at least one of the following steps:

(a) providing an immune-cell obtainable by any one of the methods previously described;
(b) Administrating said transformed immune cells to said patient, On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor.

By allogeneic is meant that the cells or population of cells used for treating patients are not originating from said patient but from a donor.

Cells that can be used with the disclosed methods are described in the previous section.

Thus, in one aspect the present invention provides an engineered immune cell according to the invention comprising a specific BCMA CAR according to the invention for use as a medicament.

In a preferred embodiment, the present invention provides an engineered immune cell comprising a specific BCMA CAR according to the invention for use as a medicament for the prevention or the treatment of a pathological condition.

In the present invention, said pathological condition is directly or indirectly induced by BCMA or a BCMA expressing cell.

In one embodiment said pathological condition is an inflammatory disease or an auto immune disease.

In another embodiment said pathological condition is a pre-malignant or malignant cancer condition.

A treatment according to the invention can be used to treat patients diagnosed wherein a pre-malignant or malignant cancer condition (a cancer) characterized by BCMA-expressing cells, especially by an overabundance of BCMA-expressing cells.

In some embodiments, the cancer is multiple myeloma malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, or another B-cell related lymphomas.

Preferably a pathological condition treated using the anti-BCMA CAR T cell of the invention is systemic Lupus Erythematosus, Sjögren syndrome, multiple sclerosis and rheumatoid arthritis, B-cell malignancies, chronic lymphocytic leukaemia (CLL), non-Hodgkins lymphoma (NHL) and Multiple myeloma (MM).

More preferably a pathological condition treated using the anti-BCMA CAR T cell of the invention is relapsing or refractory B-cell malignancies, relapsing or refractory chronic lymphocytic leukaemia (CLL), relapsing or refractory non-Hodgkins lymphoma (NHL) and relapsing or refractory Multiple myeloma (MM)

In some embodiments, an isolated cell according to the invention, or cell line derived from the isolated cells, can be used in the manufacture of a medicament for treatment of a condition as above in a patient in need thereof, in particular a pathological condition.

Also provided herein are methods for treating patients. In some embodiments the method comprises providing an immune cell of the invention to a patient in need thereof. In some embodiments, the method comprises a step of administrating BCMA CAR expressing immune cells of the invention to a patient in need thereof.

Such conditions are found in hematologic cancers, such as leukemia or malignant lymphoproliferative disorders.

Leukemia can be acute myelogenous leukemia, chronic myelogenous leukemia, melodysplastic syndrome, acute lymphoid leukemia, chronic lymphoid leukemia, and myelodysplastic syndrome.

Lymphoproliferative disorder can be lymphoma, in particular multiple myeloma, non-Hodgkin's lymphoma, Burkitt's lymphoma, and follicular lymphoma (small cell and large cell).

Cancers that may be treated may comprise nonsolid tumors (such as hematological tumors, including but not limited to pre-B ALL (pediatric indication), adult ALL, mantle cell lymphoma, diffuse large B-cell lymphoma and the like. Types of cancers to be treated with the CARs of the invention include, but are not limited leukemia or lymphoid malignancies. Adult tumors/cancers and pediatric tumors/cancers are also included.

Adult tumors/cancers and pediatric tumors/cancers may be solid cancers such as urothelial bladder cancer and squamous cell carcinoma, relapsing or refractory forms of these cancers.

In a preferred embodiment, an isolated cell according to the invention, or cell line derived from the isolated cells, can be used for preventing or altering cancer metastasis. The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

The treatment with the engineered immune cells according to the invention may be a combination with anti-BCMA CAR one or more of the following agent, an alkylating agent, a corticosteroid, a platinum drug, a purine analog, an anti-metabolite and another chemotherapy drug.

Alkylating agents include Cyclophosphamide (Cytoxan®) Chlorambucil, Bendamustine (Treanda®), Ifosfamide (Ifex®)

Corticosteroids include Prednisone, Dexamethasone (Decadron®), Platinum drugs include, Cisplatin, Carboplatin, Oxaliplatin Purine analogs include Fludarabine (Fludara®), Pentostatin (Nipent®), Cladribine (2-CdA, Leustatin®).

Anti-metabolites include Cytarabine (ara-C), Gemcitabine (Gemzar®), Methotrexat, Pralatrexate (Folotyn®).

Chemotherapy drugs include, Vincristine (Oncovin®), Doxorubicin (Adriamycin®), Mitoxantrone, Etoposide (VP-16), Bleomycin.

In certain embodiments of the present invention, anti-BCMA CAR expressing cells are administered to a patient in conjunction (e.g., before, simultaneously or following)

with a drug selected from Aracytine, Cytosine Arabinoside, amsacrine, Daunorubicine, Idarubicine, Novantrone, Mitoxantrone, Vepeside, Etoposide (VP16), arsenic trioxide, transretinoic acid, mechlorethamine, procarbazine, chlorambucil, and combination thereof. In these embodiments anti-BCMA CAR expressing T cells may be resistant to the particular drug or combination of drugs that is (are) administered in conjunction with anti-BCMA CAR expressing cells.

In other embodiments of the present invention, anti-BCMA CAR expressing cells are administered to a patient in conjunction with a drug selected from cytarabine, anthracyclines, 6-thioguanine, hydroxyurea, prednisone, and combination thereof and anti-BCMA CAR expressing cells are resistant to at least one drug selected from cytarabine, anthracyclines, 6-thioguanine, hydroxyurea, prednisone.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administered in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Other Definitions

Unless otherwise specified, "a," "an," "the," and "at least one" are used interchangeably and mean one or more than one.—Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity. One example of CAR used in the present invention is a CAR directing against BCMA antigen and can comprise as non-limiting example the amino acid sequences: SEQ ID NO: 19 to 42. Preferably said anti-BCMA CAR is of SEQ ID NO. 48 to SEQ ID NO.59 and more preferably said anti-BCMA CAR is having at least 80% identity with the amino acid sequences selected from SEQ ID NO 48 to SEQ ID NO. 59.

By V1 structure is intended molecules that combine
  a CD8alpha signal peptide,
  a VH domain separated to a VL domain by a linker, said VH and VL contributing to the binding to BCMA,
  a Hinge from Fcgamma RIIIalpha
  a transmembrane domain derived from CD8alpha
  a cytoplasmic domain derived from 41BB and CD3 zeta By V2 structure is intended molecules with a V1 structure and wherein the transmembrane domain derived from 41BB By V3 structure is intended molecules that combine
  a CD8alpha signal peptide,
  a VH domain separated to a VL domain by a linker, said VH and VL contributing to the binding to BCMA,
  a Hinge from CD8alpha
  a transmembrane domain derived from CD8alpha
  a cytoplasmic domain derived from 41BB and CD3 zeta By V4 structure is intended molecules with a V3 structure and wherein the transmembrane domain derived from 41BB.

By V5 structure is intended molecules that combine
  a CD8alpha signal peptide,
  a VH domain separated to a VL domain by a linker, said VH and VL contributing to the binding to BCMA,
  a Hinge from IgG1
  a transmembrane domain derived from CD8alpha
  a cytoplasmic domain derived from 41BB and CD3 zeta.

By V6 structure is intended molecules with a V5 structure and wherein the transmembrane domain derived from 41BB.

The CAR structures of the invention are illustrated in FIG. 2.

The term "chemotherapy" refers to any therapy using a chemical, in particular those used against cancer.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a Cas9 endonuclease from CRISPR system (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YC for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Bock, Scholze et al. 2009; Moscou and Bogdanove 2009; Christian, Cermak et al. 2010; Li, Huang et al. 2011). Custom-made TAL-nucleases are commercially available under the trade name TALEN (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the proto-spacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By "recombinant antibody" as used herein, is meant an antibody or antibody fragment which is generated using recombinant DNA technology, such as, for example, an antibody or antibody fragment expressed by a bacteriophage, a yeast expression system or a mammalian cell expression system. The term should also be construed to mean an antibody or antibody fragment which has been generated by the synthesis of a DNA molecule encoding the antibody or antibody fragment and which DNA molecule expresses an antibody or antibody fragment protein, or an amino acid sequence specifying the antibody or antibody fragment, wherein the DNA or amino acid sequence has been obtained using recombinant or synthetic DNA or amino acid sequence technology which is available and well known in the art.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

An amino acid can be anyone of the amino acid, for example alanine, asparagine, aspartic acid, cysteine, glutamine, glutamic acid, glycine histidine, isoleucine, leucine, lysine, methionine, phenylalanine, proline, serine, threonine, tryptophan, tyrosine, valine, aspartic acid, glutamic acid.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The term "treatment" is an approach for obtaining beneficial or desired clinical results. For purposes of this invention, beneficial or desired clinical results include, but are not limited to, one or more of the following: reducing the number and/or proliferation of neoplastic or cancerous cells, inhibiting metastasis of neoplastic cells, decreasing the size of BCMA expressing tumor, in particular in urothelial bladder cancer and squamous cell carcinoma, preventing or altering cancer metastasis, remission of a BCMA associated disease (e.g., cancer), decreasing symptoms resulting from a BCMA associated disease (e.g., cancer), increasing the quality of life of those suffering from a BCMA associated disease (e.g., cancer), decreasing the dose of other medications required to treat a BCMA associated disease (e.g., cancer), delaying the progression of a BCMA associated disease (e.g., cancer), curing a BCMA associated disease (e.g., cancer), and/or prolong survival of patients having a BCMA associated disease (e.g., cancer).

"Ameliorating" means a lessening or improvement of one or more symptoms as compared to not administering a BCMA antibody or a BCMA antibody conjugate. "Ameliorating" also includes shortening or reduction in duration of a symptom. The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

General Methods:

Inactivation of Specific Gene(s) in Primary T Cells

Inactivation of specific gene(s) in primary T cells may be performed before or after CAR introduction into T cells.

At least one gene, one gene or two genes may be inactivated in one step or in successive steps. In a preferred embodiment two genes may be inactivated at once, preferably TCRalpha gene and a drug sensitivity gene. Inactivation of a drug sensitivity gene confers resistance to said drug. Alternatively, (over)expression of a drug resistance gene confers resistance to said drug.

In general, heterodimeric nuclease, in particular TALE-Nuclease targeting two long sequences (called half targets) separated by a spacer within a target gene is designed and produced.

Each TALE-nuclease construct may be cloned in an appropriate mammalian expression vector. mRNA encoding TALE-nuclease cleaving a targeted genomic sequence may be synthesized from plasmid carrying the coding sequence downstream a promoter.

Cells are purified T cells preactivated with anti-CD3/CD28 coated beads. Cells are transfected with each of the 2 mRNAs encoding both half TALE-nucleases, in particular both half TALE-nucleases and spacer.

Cells may be reactivated with soluble anti-CD28 to measure cell proliferation and the activation marker CD25 detected to assess the activation state of the cells.

Chimeric Antigen Receptors

Nucleic Acids—Vectors

An acid nucleic (mRNA or lentiviral vector) encoding a CAR of the invention is constructed.

A lentiviral vectors may be prepared for example as previously described in the art (eg in WO2013176915, WO2013176916, or in WO2014130635 and incorporated herein by reference). Lentiviral vectors are produced by Vectalys SA (Toulouse, France) by transfecting genomic and helper plasmids in HEK-293 cells.

CAR mRNAs may be produced using T7 mRNA polymerase and transfections done using Cytopulse technology.

Screening and Selection of CAR

Primary T-Cell Cultures

T cells are purified from Buffy coat samples provided by EFS (Etablissement Français du Sang, Paris, France) using Ficoll gradient density medium. The PBMC layer is recovered and T cells purified using a commercially available T-cell enrichment kit. Purified T cells are activated in X-Vivo-15 medium (Lonza) using Human IL-2 and Dynabeads Human T activator CD3/CD28.

CAR mRNA Transfection

Transfections of CAR mRNAs_encoding the different CAR constructs are performed at Day 4 or Day 11 after T-cell purification and activation.

CAR Transduction

T-cell transduction with recombinant lentiviral vectors allowing the expression of CAR Transduction of T-cells with recombinant lentiviral vectors are carried out three days after T-cell purification/activation. Transductions may be carried out at various multiplicity of infection (MOI), in particular at a MOI of 5. CAR detection at the surface of T-cells is performed using a recombinant protein consisting on the extracellular domain of the protein to which the CAR of the invention is binding, fused together with a murine IgG1 Fc fragment (produced by LakePharma).

Binding of this protein to the CAR molecule is detected with a PE-conjugated secondary antibody (Jackson Immunoresearch) targeting the mouse Fc portion of the protein, and Degranulation Assay (CD107a Mobilization)

T-cells are incubated together with an equal amount of cells expressing various levels of the protein targeted by the CAR of the invention (BCMA). Co-cultures are maintained for at least 6 hours. CD107a staining is performed during cell stimulation, by the addition of a fluorescent anti-CD107a antibody at the beginning of the co-culture. After the 6 h incubation period, cells are stained with a fixable viability dye and fluorochrome-conjugated anti-CD8 and analyzed by flow cytometry. The degranulation activity is determined as the % of CD8+/CD107a+ cells, and by determining the mean fluorescence intensity signal (MFI) for CD107a staining among CD8+ cells.

Degranulation assays are carried out 24 h after mRNA transfection.

IFN Gamma Release Assay 24 h after mRNA transfection, CAR expressing T-cells are incubated together with cell lines expressing various levels of the BCMA protein for 24 hours at 37° C. The supernatants are recovered and IFN gamma detection in the cell culture supernatants is done by ELISA assay.

Cytotoxicity Assay

CAR expressing T-cells are incubated together with target cells or (control) cells in the same well. Target and control cells are labelled with fluorescent intracellular dyes (eg. CFSE or Cell Trace Violet), before co-culture with for 4 hours at 37° C. After this incubation period, cells are labelled with a fixable viability dye and analyzed by flow cytometry. Viability of each cellular population (target cells or control cells) is determined and the % of specific cell lysis is calculated. Cytotoxicity assays are carried out 48 h after mRNA transfection.

Anti-Tumor Mouse Model

Immuno deficient NOG mice are intravenously (iv) injected with—Luciferase cells expressing the targeted protein (recognized by the CAR). Optionally, mice receive an anticancer treatment at various doses before injection with CAR T-cells. Mice are then iv injected (eg either 2 or 7 days after injection of the tumor cell line) with different doses of CAR+ T-cells of the invention to be tested, or with T-cells that were not transduced with the CAR lentiviral vector. Bioluminescent signals are determined at the day of T-cell injection (DO), at D7, 14, 21, 28 and 40 after T-cell injection in order to follow tumoral progression in the different animals. Mice which survived were then treated with an inducer to selectively destroy CAR expressing immune cells Having generally described this invention, a further understanding can be obtained by reference to certain specific examples, which are provided herein for purposes of illustration only, and are not intended to be limiting unless otherwise specified.

EXAMPLES

Example 1: Preparation of TCR KO T Cells

Proliferation of TCRalpha Inactivated Cells Expressing a BCMA-CAR.

Heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in Table 10.

TABLE 10

TAL-nucleases targeting TCRalpha gene

| Target | Target sequence | Repeat sequence | Half TALE-nuclease |
|---|---|---|---|
| TRAC_T01 | TTGTCCCACAGATATCC Agaaccctgaccctg CCGTGTACCAGCTGAGA (SEQ ID NO: 43) | Repeat TRAC_T01-L (SEQ ID NO: 44) Repeat TRAC_T01-R (SEQ ID NO: 45) | TRAC_T01-L TALEN (SEQ ID NO: 46) TRAC_T01-R TALEN (SEQ ID NO: 47) |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with anti-CD3/CD28 coated beads were transfected with each of the 2 mRNAs encoding both half TRAC_T01 TALE-nucleases. 48 hours post-transfection, different groups of T cells from the same donor were respectively transduced with a lentiviral vector encoding one of the BCMA CAR previously described (SEQ ID NO: 19 to 42). 2 days post-transduction, $CD3_{NEG}$ cells were purified using anti-CD3 magnetic beads and 5 days post-transduction cells were reactivated with soluble anti-CD28 (5 µg/ml). Alternatively, BCMA CAR expression and TCR inactivation can be performed at the same time, in one step by transduction of appropriate vectors.

The present invention provides therefore TCR KO T cells that proliferate.

Cell proliferation was followed for up to 30 days after reactivation by counting cell 2 times per week. Increased proliferation in TCR alpha inactivated cells expressing the BCMA CARs, especially when reactivated with anti-CD28, was observed compared to non-transduced cells.

To investigate whether the human T cells expressing the BCMA CAR display activated state, the expression of the activation marker CD25 are analyzed by FACS 7 days post transduction. The purified cells transduced with the lentiviral vector encoding BCMA CAR assayed for CD25 expression at their surface in order to assess their activation in comparison with the non-transduced cells. Increased CD25 expression is expected both in CD28 reactivation or no reactivation conditions.

Example 2: Screening of BCMA CARs According to the Invention 4 different scFv's from C11D5.3, C13F12.1, BC30 and BC50 antibody were constructed and used to generate Chimeric Antigen Receptors (CARs) and screen for their degranulation activity towards BCMA+ cells.

Different architectures of each CAR were designed (namely V1, V3 and V5) and their activity was determined upon transient expression in human primary T-cells.

Primary T-Cell Cultures

T cells were purified from Buffy coat samples provided by EFS (Etablissement Français du Sang, Paris, France) using Ficoll gradient density medium (Ficoll Paque PLUS/GE Healthcare Life Sciences). The PBMC layer was recovered and T cells were purified using a commercially available T-cell enrichment kit (Stem Cell Technologies). Purified T cells were activated in X-Vivo-15 medium (Lonza) supplemented with 20 ng/mL Human IL-2 (Miltenyi Biotech), 5% Human Serum (Sera Laboratories), and Dynabeads Human T activator CD3/CD28 at a bead:cell ratio 1:1 (Life Technologies). After activation cells were grown and maintained in X-Vivo-15 medium (Lonza) supplemented with 20 ng/mL Human IL-2 (Miltenyi Biotec) and 5% Human Serum (Sera Laboratories).

CAR mRNA Transfection

Transfections were done at Day 4 or Day 11 after T-cell purification and activation. 5 millions of cells were transfected with 15 μg of mRNA encoding the different CAR constructs. CAR mRNAs were produced using the mMESSAGE mMACHINE T7 Kit (Life Technologies) and purified using RNeasy Mini Spin Columns (Qiagen). Transfections were done using Cytopulse technology, by applying two 0.1 mS pulses at 3000V/cm followed by four 0.2 mS pulses at 325V/cm in 0.4 cm gap cuvettes in a final volume of 200 μl of "Cytoporation buffer T" (BTX Harvard Apparatus). Cells were immediately diluted in X-Vivo[n]-15 media (Lonza) and incubated at 37° C. with 5% $CO_2$. IL-2 (from Miltenyi Biotec was added 2 h after electroporation at 20 ng/mL.

Degranulation Assay (CD107a Mobilization)

T-cells were incubated in 96-well plates (40,000 cells/well), together with an equal amount of cells expressing or not the BCMA protein. Co-cultures were maintained in a final volume of 100 μl of X-Vivo-15 medium (Lonza) for 6 hours at 37° C. with 5% $CO_2$. CD107a staining was done during cell stimulation, by the addition of a fluorescent anti-CD107a antibody (APC conjugated, from Miltenyi Biotec) at the beginning of the co-culture, together with 1 μg/ml of anti-CD49d (BD Pharmingen), 1 μg/ml of anti-CD28 (Miltenyi Biotec), and 1× Monensin solution (eBioscience). After the 6 h incubation period, cells were stained with a fixable viability dye (eFluor 780, from eBioscience) and fluorochrome-conjugated anti-CD8 (PE conjugated Miltenyi Biotec) and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24 h after mRNA transfection. The example on FIG. 3 shows degranulation activity of CARs from the 4 different scFv's, when CAR+ T-cells were co-cultured for 6 hours with BCMA expressing cells (RPMI8226 or H929), or with cells that do not express BCMA (K562).

Three different architectures were tested for the BC30 and BC50 scFv's (v1, v3 and v5), and two were tested for the two other scFv's C11D5.3 and C13F12.1 (v3 and v5).

Figure 3:
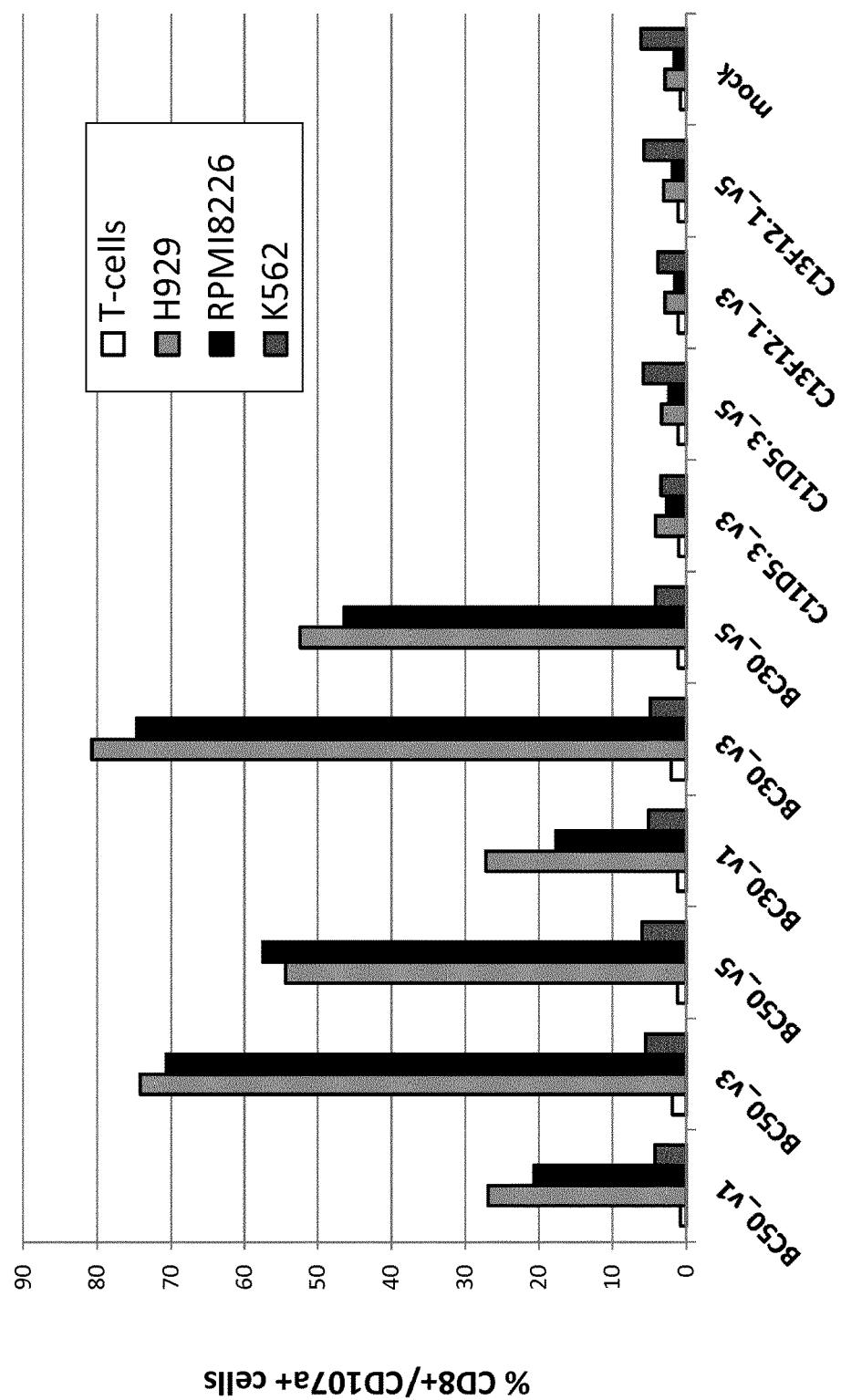
FIG. 3: Degranulation activity of CARs from the 4 different scFv's, when CAR+ T-cells were co-cultured for 6 hours with BCMA expressing cells (RPMI8226 or H929), or with cells that do not express BCMA (K562). Three different architectures were tested for the BC30 and BC50 scFv's (v1, v3 and v5), while only two were tested for the two other scFv's C11D5.3 and C13F12.1 (v3 and v5).

The results in FIG. 3 indicate that BC30 and BC50 derived CARs T cells are active against BCMA expressing cancer cells, while no activity is detected in CARs T cells wherein said CAR is derived from the C11D5.3 or C13F12.1 scFv's (FIG. 3).

The engineered T-cells of the invention display increased selectivity in vitro and increased cytolytic activity as compared to T-cells expressing a BCMA CAR derived from C11D5.3 or C13F12.1 scFv's.

Example 3: Activity of BCMA CAR Expressing T Cells Towards BCMA Expressing Cancer Cells Among all the CAR molecules generated, 6 active molecules were selected for further activity tests.

For this, T-cells were isolated from buffy-coat samples and activated using CD3/CD28 beads as described above. Cells were transiently transfected with mRNAs encoding the different candidates at D11 after activation. CAR activity was assessed by measuring their degranulation capacity, the IFNgamma release, and the cytotoxic activity when co-cultured with cells expressing or not BCMA.

Figure 4:
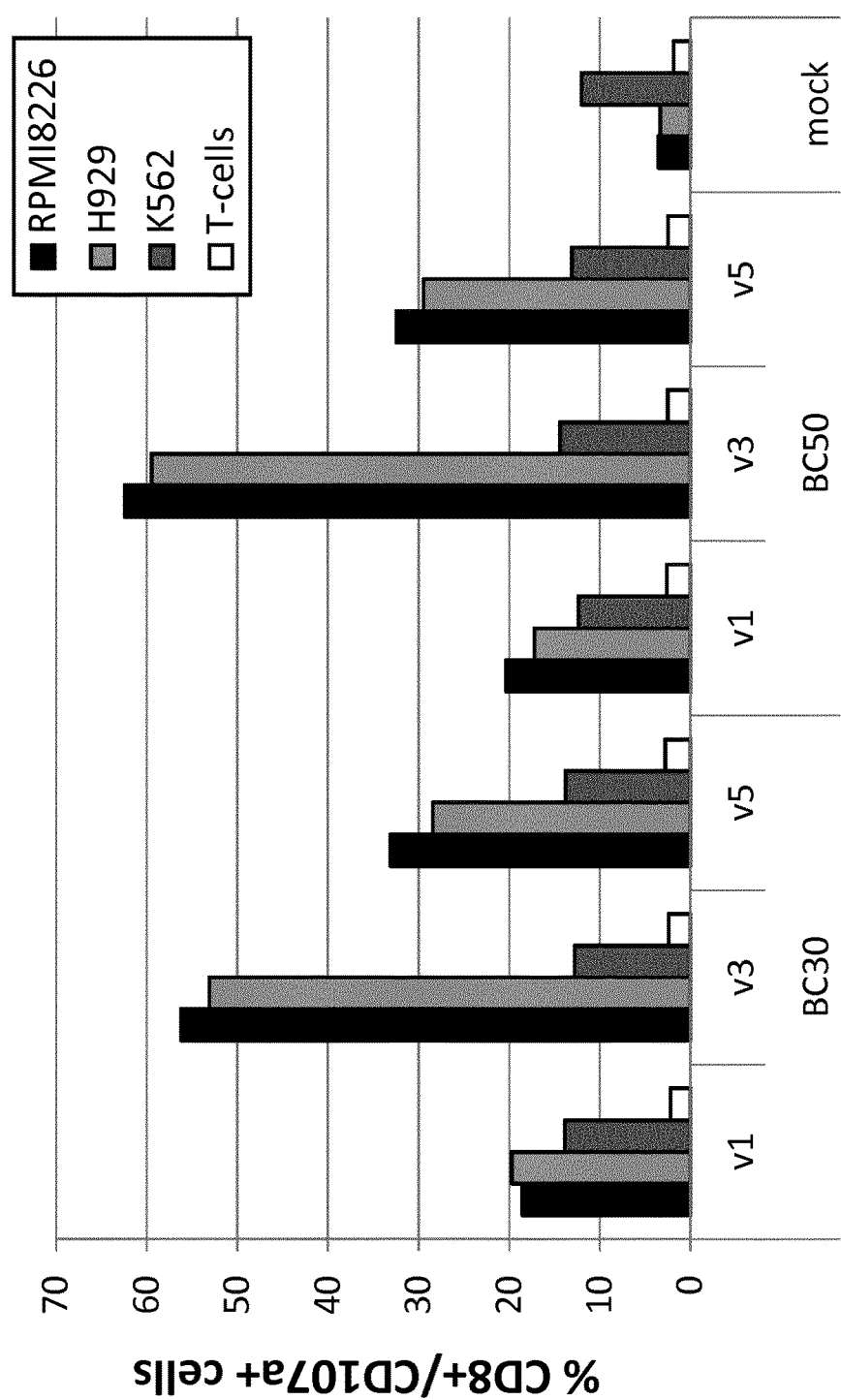
FIG. 4: Degranulation activity (CD107a+ cells) of CAR T-cells after 6 h co-cultures with BCMAneg cells (K562) or cells expressing BCMA (RPMI8226 and NCI-H929). Co-cultures were started 24 h after CAR mRNA electroporation. Three different architectures were tested for the BC30 and BC50 scFv's (v1, v3 and v5). The results represent the mean values of three independent experiments.

FIG. 4 shows the degranulation activity (CD107a+ cells) of CAR T-cells after 6 h co-cultures with BCMA neg cells (K562) or cells expressing BCMA (RPMI8226 and NCI-H929). Co-cultures were started 24 h after CAR mRNA electroporation. The results represent the mean values of three independent experiments.

The results in FIG. 4 confirmed the degranulation activity of BC30 and BC50 derived CARs expressed in T cells.

Figure 5:
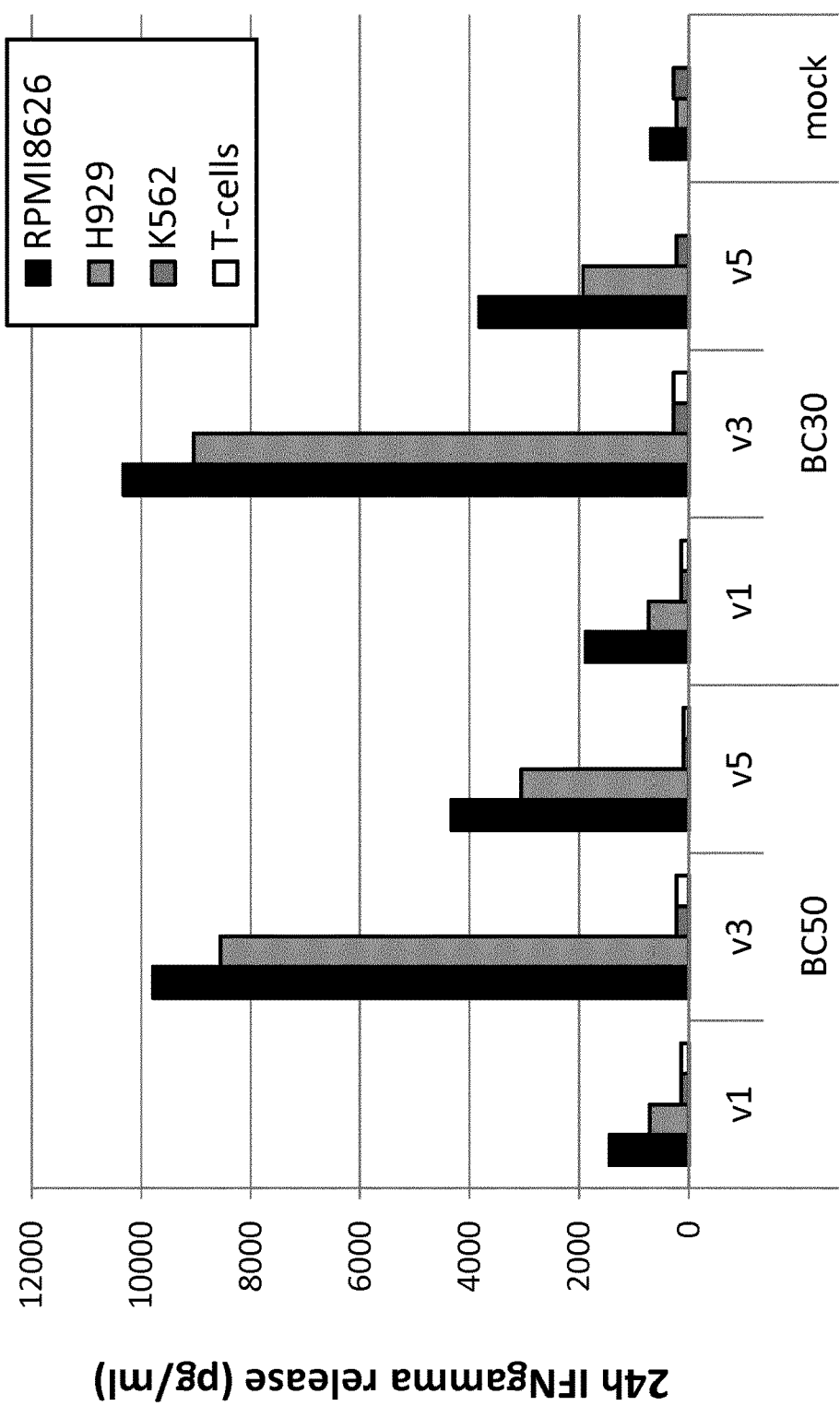
FIG. 5: IFNgamma released by T-cells when co-cultured for 24 h with cells expressing BCMA (NCI-H929 or RPMI8226), or with cells that do not express BCMA (K562). IFNgamma release from T-cells cultured alone, in the same conditions that the co-cultures, is also shown. Three different architectures were tested for the BC30 and BC50 scFv's (v1, v3 and v5). The experiments were done for three independent donors.

The amount of IFNgamma released by CAR T-cells was measured when co-cultured for 24 h with cells expressing BCMA (NCI-H929 or RPMI8226), or with cells that do not express BCMA (K562). IFNgamma release from T-cells cultured alone, in the same conditions that the co-cultures, is also shown in FIG. 5. The experiments were done for three independent donors.

Figure 6:
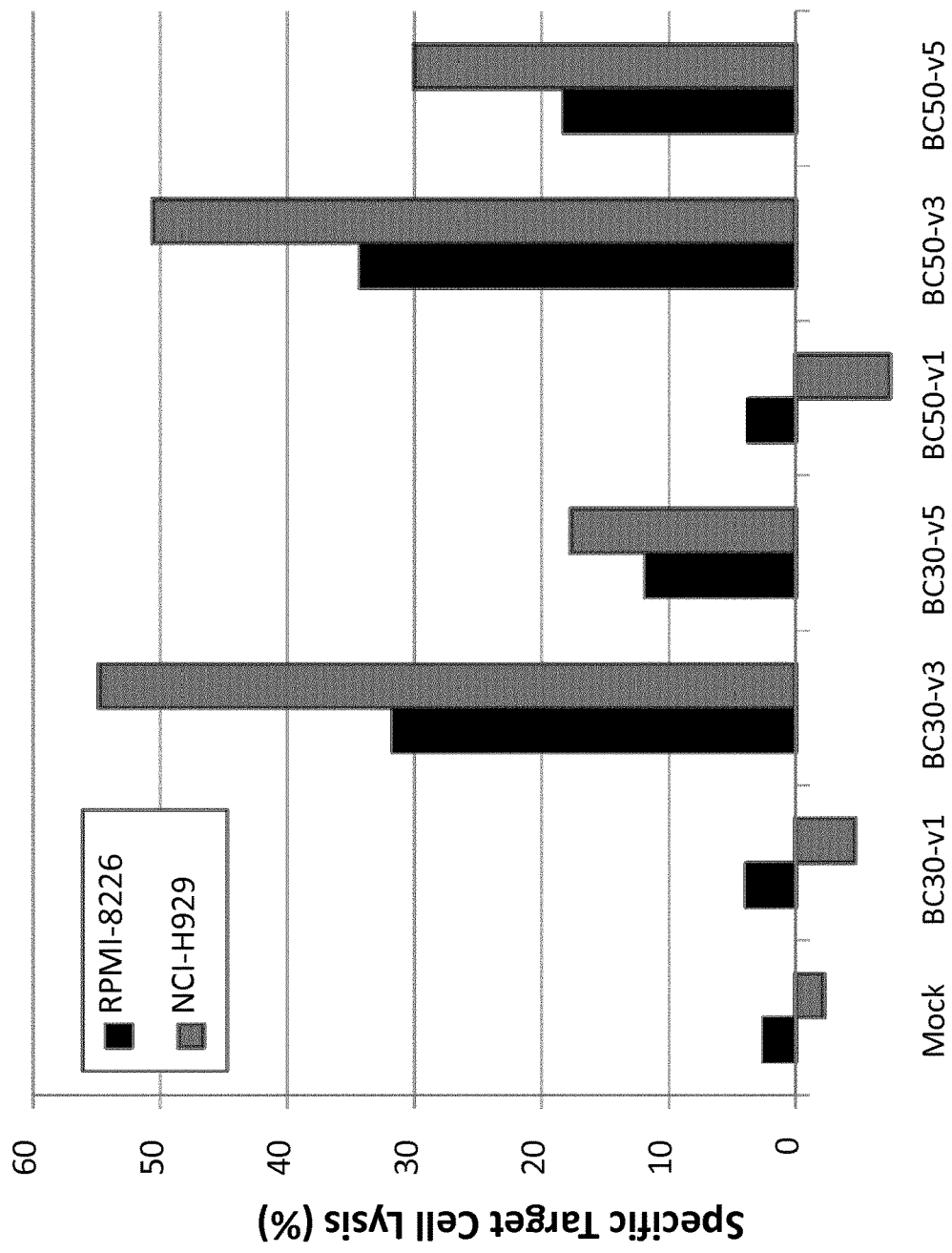
FIG. 6: Specific cytolytic activity of CAR-T cells. Three different architectures were tested for the BC30 and BC50 scFv's (v1, v3 and v5). Assays were done 48 h after CAR mRNA transfection. T-cells were co-cultured with K562+RPMI8226 or K562+NCIH929 cells for 4 hours. Cellular viability for each of the cell lines was determined at the end of the co-cultured and a specific cell lysis percentage was calculated.

The specific cytolytic activity of CAR-T cells was measured (FIG. 6). Assays were done 48 h after CAR mRNA transfection. T-cells were co-cultured with K562+RPMI8226 or K562+NCIH929 cells for 4 hours. Cellular viability for each of the cell lines was determined at the end of the co-cultured and a specific cell lysis percentage was calculated.

The results obtained in the three activity tests allowed identifying BC30-v3 and BC50-v3 as the most active candidates, with the v5 or V1 versions of both scFv's derived CARs displaying also good activities, tough lower than the corresponding v3 candidates with a lower IFNgamma release.

The BC30 and BC50 derived CAR of the invention confer T cells specificity and activity against BCMA expressing cancer cells.

IFNgamma Release Assay

T-cells were incubated in 96-well plates (40,000 cells/well), together with an equal amount of cells expressing or not the BCMA protein. Co-cultures were maintained in a final volume of 100 μl of X-Vivo-15 medium (Lonza) for 6 hours at 37° C. with 5% $CO_2$. CD107a staining was done during cell stimulation, by the addition of a fluorescent anti-CD107a antibody (APC conjugated, from Miltenyi Biotec) at the beginning of the co-culture, together with 1 μg/ml of anti-CD49d (BD Pharmingen), 1 μg/ml of anti-CD28 (Miltenyi Biotec), and 1× Monensin solution (eBioscience). After the 6 h incubation period, cells were stained with a fixable viability dye (eFluor 780, from eBioscience) and fluorochrome-conjugated anti-CD8 (PE conjugated Miltenyi Biotec) and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24 h after mRNA transfection.

Cytotoxicity Assay

T-cells were incubated in 96-well plates (100,000 cells/well), together with 10,000 target cells (expressing BCMA NCI-H929 or RPMI-8226 cells) and 10,000 control (BCMA neg K562) cells in the same well. Target and control cells were labelled with fluorescent intracellular dyes (CFSE or Cell Trace Violet, from Life Technologies) before co-culturing them with CAR+ T-cells. The co-cultures were incubated for 4 hours at 37° C. with 5% $CO_2$. After this incubation period, cells were labelled with a fixable viability dye (eFluor 780, from eBioscience) and analyzed by flow cytometry. Viability of each cellular population (target cells or BCMAneg control cells) was determined and the % of specific cell lysis was calculated. Cytotoxicity assays were carried out 48 h after mRNA transfection. The BCMA30 and BCMA50 derived CARs of the invention were then transduced into primary TCR KO primary T cells and tested in vivo against BCMA expressing cancer cells.

The results demonstrate a significant reduction of the amount of BCMA expressing cancer cells even in the presence of anti-cancer drug (corticoids, bortezomib). In addition, mice exhibited much less signs of graft versus host rejection when inoculated with TCR negative T cells, than when inoculated with TCR expressing cells.

100 days after implantation of BCMA T cells in mice, RQR8 positive BCMA T cells were still detectable. Injection of Rituximab into mice resulted in an undetectable level of cells. Mice recovered properly.

The present invention provides therefore anti-BCMA CAR expressing T cells, originally allogenic, in particular BCMA30 or BCMA50 derived CAR expressing T cells for their use as a medicament against different BCMA expressing cancer cells which are well tolerated and can be eliminated.

Examples of CAR Polypeptide Sequences:

Framed sequences correspond to preferred VH and VL sequences. VH and VL may be swapped to improve CAR efficiency.

In one embodiment the present invention provides a BCMA specific chimeric antigen receptor (CAR) comprising one of the following polypeptide, optionally humanized.

```
BC50-1
                                          (SEQ ID NO. 1 + SEQ ID NO. 19)
MALPVTALLLPLALLLHAARP QVQLVQSGAEVKKPGASVKVSCKASGYSFPDYYINWVRQA

PGQGLEWMGWIYFASGNSEYNQKFTGRVTMTRDTSINTAYMELSSLTSEDTAVYFCASLY

DYDWYFDVWGQGTMVTVSS GGGGSGGGGSGGGGS DIVMTQTPLSLSVTPGQPASISCK

SSQSLVHSNGNTYLHWYLQKPGQSPQLLIYKVSNRFSGVPDRFSGSGSGTDFTLKISRVEA

EDVGIYYCSQSSIYPWTFGQGTKLEIK GLAVSTISSFFPPGYQIYIWAPLAGTCGVLLLSLVITL

YCKRGRKKLLYIFKQPFMRPVQTTQEEDGCSCRFPEEEEGGCELRVKFSRSADAPAYQQG

QNQLYNELNLGRREEYDVLDKRRGRDPEMGGKPRRKNPQEGLYNELQKDKMAEAYSEIG

MKGERRRGKGHDGLYQGLSTATKDTYDALHMQALPPR

BC50-2
                                          (SEQ ID NO. 1 + SEQ ID NO. 20)
MALPVTALLLPLALLLHAARP QVQLVQSGAEVKKPGASVKVSCKASGYSFPDYYINWVRQA

PGQGLEWMGWIYFASGNSEYNQKFTGRVTMTRDTSINTAYMELSSLTSEDTAVYFCASLY

DYDWYFDVWGQGTMVTVSS GGGGSGGGGSGGGGS DIVMTQTPLSLSVTPGQPASISCK

SSQSLVHSNGNTYLHWYLQKPGQSPQLLIYKVSNRFSGVPDRFSGSGSGTDFTLKISRVEA

EDVGIYYCSQSSIYPWTFGQGTKLEIK GLAVSTISSFFPPGYQIISFFLALTSTALLFLLFFLTLR

FSWKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSE

IGMKGERRRGKGHDGLYQGLSTATKDTYDALHMQALPPR

BC50-3
                                          (SEQ ID NO. 1 + SEQ ID NO. 21)
MALPVTALLLPLALLLHAARP QVQLVQSGAEVKKPGASVKVSCKASGYSFPDYYINWVRQA

PGQGLEWMGWIYFASGNSEYNQKFTGRVTMTRDTSINTAYMELSSLTSEDTAVYFCASLY

DYDWYFDVWGQGTMVTVSS GGGGSGGGGSGGGGS DIVMTQTPLSLSVTPGQPASISCK

SSQSLVHSNGNTYLHWYLQKPGQSPQLLIYKVSNRFSGVPDRFSGSGSGTDFTLKISRVEA

EDVGIYYCSQSSIYPWTFGQGTKLEIK TTTPAPRPPTPAPTIASQPLSLRPEACRPAAGGAV

HTRGLDFACDIYIWAPLAGTCGVLLLSLVITLYCKRGRKKLLYIFKQPFMRPVQTTQEEDGCS
```

CRFPEEEEGGCELRVKFSRSADAPAYQQGQNQLYNELNLGRREEYDVLDKRRGRDPEMG
GKPRRKNPQEGLYNELQKDMAEAYSEIGMKGERRRGKGHDGLYQGLSTATKDTYDALH
MQALPPR

BC50-4

(SEQ ID NO. 1 + SEQ ID NO. 22)

MALPVTALLLPLALLLHAARPQVQLVQSGAEVKKPGASVKVSCKASGYSFPDYYINWVRQA
PGQGLEWMGWIYFASGNSEYNQKFTGRVTMTRDTSINTAYMELSSLTSEDTAVYFCASLY
DYDWYFDVWGQGTMVTVSSGGGGSGGGGSGGGGSDIVMTQTPLSLSVTPGQPASISCK
SSQSLVHSNGNTYLHWYLQKPGQSPQLLIYKVSNRFSGVPDRFSGSGSGTDFTLKISRVEA
EDVGIYYCSQSSIYPWTFGQGTKLEIKTTTPAPRPPTPAPTIASQPLSLRPEACRPAAGGAV
HTRGLDFACDIISFFLALTSTALLFLLFFLTLRFSVVKRGRKKLLYIFKQPFMRPVQTTQEEDG
CSCRFPEEEEGGCELRVKFSRSADAPAYQQGQNQLYNELNLGRREEYDVLDKRRGRDPE
MGGKPRRKNPQEGLYNELQKDMAEAYSEIGMKG ERRRGKGHDGLYQGLSTATKDTYDA
LHMQALPPR

BC50-5

(SEQ ID NO. 1 + SEQ ID NO. 23)

MALPVTALLLPLALLLHAARPQVQLVQSGAEVKKPGASVKVSCKASGYSFPDYYINWVRQA
PGQGLEWMGWIYFASGNSEYNQKFTGRVTMTRDTSINTAYMELSSLTSEDTAVYFCASLY
DYDWYFDVWGQGTMVTVSSGGGGSGGGGSGGGGSDIVMTQTPLSLSVTPGQPASISCK
SSQSLVHSNGNTYLHWYLQKPGQSPQLLIYKVSNRFSGVPDRFSGSGSGTDFTLKISRVEA
EDVGIYYCSQSSIYPWTFGQGTKLEIKEPKSPDKTHTCPPCPAPPVAGPSVFLFPPKPKDTL
MIARTPEVTCVWVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALH
NHYTQKSLSLSPGKIYIWAPLAGTCGVLLLSLVITLYCKRGRKKLLYIFKQPFMRPVQTTQEE
DGCSCRFPEEEEGGCELRVKFSRSADAPAYQQGQNQLYNELNLGRREEYDVLDKRRGRD
PEMGGKPRRKNPQEGLYNELQKDMAEAYSEIGMKGERRRGKGHDGLYQGLSTATKDTY
DALHMQALPPR

BC50-6

(SEQ ID NO. 1 + SEQ ID NO. 24)

MALPVTALLLPLALLLHAARPQVQLVQSGAEVKKPGASVKVSCKASGYSFPDYYINWVRQA
PGQGLEWMGWIYFASGNSEYNQKFTGRVTMTRDTSINTAYMELSSLTSEDTAVYFCASLY
DYDWYFDVWGQGTMVTVSSGGGGSGGGGSGGGGSDIVMTQTPLSLSVTPGQPASISCK
SSQSLVHSNGNTYLHWYLQKPGQSPQLLIYKVSNRFSGVPDRFSGSGSGTDFTLKISRVEA
EDVGIYYCSQSSIYPWTFGQGTKLEIKEPKSPDKTHTCPPCPAPPVAGPSVFLFPPKPKDTL
MIARTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALH
NHYTQKSLSLSPGKIISFFLALTSTALLFLLFFLTLRFSWKRGRKKLLYIFKQPFMRPVQTTQ
EEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKGHDGLYQGLSTATKD
TYDALHMQALPPR

BC30-1

(SEQ ID NO. 1 + SEQ ID NO. 25)

MALPVTALLLPLALLLHAARPQVQLVQSGAEVKKPGASVKVSCKASGYSFPDYYINWVRQA
PGQGLEWMGWIYFASGNSEYNQKFTGRVTMTRDTSSSTAYMELSSLRSEDTAVYFCASLY
DYDWYFDVWGQGTMVTVSSGGGGSGGGGSGGGGSDIVMTQTPLSLSVTPGEPASISCK
SSQSLVHSNGNTYLHWYLQKPGQSPQLLIYKVSNRFSGVPDRFSGSGSGADFTLKISRVEA
EDVGVYYCAETSHVPWTFGQGTKLEIKGLAVSTISSFFPPGYQIYIWAPLAGTCGVLLLSLVI
TLYCKRGRKKLLYIFKQPFMRPVQTTQEEDGCSCRFPEEEEGGCELRVKFSRSADAPAYQ
QGQNQLYNELNLGRREEYDVLDKRRGRDPEMGGKPRRKNPQEGLYNELQKDKMAEAYSE
IGMKGERRRGKGHDGLYQGLSTATKDTYDALHMQALPPR

BC30-2

(SEQ ID NO. 1 + SEQ ID NO. 26)

MALPVTALLLPLALLLHAARPQVQLVQSGAEVKKPGASVKVSCKASGYSFPDYYINWVRQA
PGQGLEWMGWIYFASGNSEYNQKFTGRVTMTRDTSSSTAYMELSSLRSEDTAVYFCASLY
DYDWYFDVWGQGTMVTVSSGGGGSGGGGSGGGGSDIVMTQTPLSLSVTPGEPASISCK
SSQSLVHSNGNTYLHWYLQKPGQSPQLLIYKVSNRFSGVPDRFSGSGSGADFTLKISRVEA
EDVGVYYCAETSHVPWTFGQGTKLEIKGLAVSTISSFFPPGYQIISFFLALTSTALLFLLFFLTL
RFSWKRGRKKLLYIFKQPFMRPVQTTQEEDGCSCRFPEEEEGGCELRVKFSRSADAPAY
QQGQNQLYNELNLGRREEYDVLDKRRGRDPEMGGKPRRKNPQEGLYNELQKDKMAEAY
SEIGMKGERRRGKGHDGLYQGLSTATKDTYDALHMQALPPR

BC30-3

(SEQ ID NO. 1 + SEQ ID NO. 27)

MALPVTALLLPLALLLHAARPQVQLVQSGAEVKKPGASVKVSCKASGYSFPDYYINWVRQA
PGQGLEWMGWIYFASGNSEYNQKFTGRVTMTRDTSSSTAYMELSSLRSEDTAVYFCASLY
DYDWYFDVWGQGTMVTVSSGGGGSGGGGSGGGGSDIVMTQTPLSLSVTPGEPASISCK
SSQSLVHSNGNTYLHWYLQKPGQSPQLLIYKVSNRFSGVPDRFSGSGSGADFTLKISRVEA
EDVGVYYCAETSHVPWTFGQGTKLEIKTTTPAPRPPTPAPTIASQPLSLRPEACRPAAGGA
VHTRGLDFACDIYIWAPLAGTCGVLLLSLVITLYCKRGRKKLLYIFKQPFMRPVQTTQEEDGC
SCRFPEEEEGGCELRVKFSRSADAPAYQQGQNQLYNELNLGRREEYDVLDKRRGRDPEM
GGKPRRKNPQEGLYNELQKDKMAEAYSEIGMKGERRRGKGHDGLYQGLSTATKDTYDAL
HMQALPPR

BC30-4

(SEQ ID NO. 1 + SEQ ID NO. 28)

MALPVTALLLPLALLLHAARPQVQLVQSGAEVKKPGASVKVSCKASGYSFPDYYINWVRQA
PGQGLEWMGWIYFASGNSEYNQKFTGRVTMTRDTSSSTAYMELSSLRSEDTAVYFCASLY
DYDWYFDVWGQGTMVTVSSGGGGSGGGGSGGGGSDIVMTQTPLSLSVTPGEPASISCK
SSQSLVHSNGNTYLHWYLQKPGQSPQLLIYKVSNRFSGVPDRFSGSGSGADFTLKISRVEA
EDVGVYYCAETSHVPWTFGQGTKLEIKTTTPAPRPPTPAPTIASQPLSLRPEACRPAAGGA
VHTRGLDFACDIISFFLALTSTALLFLLFFLTLRFSVVKRGRKKLLYIFKQPFMRPVQTTQEED

-continued

GCSCRFPEEEEGGCELRVKFSRSADAPAYQQGQNQLYNELNLGRREEYDVLDKRRGRDP

EMGGKPRRKNPQEGLYNELQKDKMAEAYSEIGMKGERRRGKHDGLYQGLSTATKDTYD

ALHMQALPPR

BC30-5

(SEQ ID NO. 1 + SEQ ID NO. 29)
MALPVTALLLPLALLLHAARPQVQLVQSGAEVKKPGASVKVSCKASGYSFPDYYINWVRQA

PGQGLEWMGWIYFASGNSEYNQKFTGRVTMTRDTSSSTAYMELSSLRSEDTAVYFCASLY

DYDWYFDVWGQGTMVTVSSGGGGSGGGGSGGGGSDIVMTQTPLSLSVTPGEPASISCK

SSQSLVHSNGNTYLHWYLQKPGQSPQLLIYKVSNRFSGVPDRFSGSGSGADFTLKISRVEA

EDVGVYYCAETSHVPWTFGQGTKLEIKEPKSPDKTHTCPPCPAPPVAGPSVFLFPPKPKDT

LMIARTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSVMHEALH

NHYTQKSLSLSPGKIYIWAPLAGTCGVLLLSLVITLYCKRGRKKLLYIFKQPFMRPVQTTQEE

DGCSCRFPEEEEGGCELRVKFSRSADAPAYQQGQNQLYNELNLGRREEYDVLDKRRGRD

PEMGGKPRRKNPQEGLYNELQKDKMAEAYSEIGMKGERRRGKHDGLYQGLSTATKDTY

DALHMQALPPR

BC30-6

(SEQ ID NO. 1 + SEQ ID NO. 30)
MALPVTALLLPLALLLHAARPQVQLVQSGAEVKKPGASVKVSCKASGYSFPDYYINWVRQA

PGQGLEWMGWIYFASGNSEYNQKFTGRVTMTRDTSSSTAYMELSSLRSEDTAVYFCASLY

DYDWYFDVWGQGTMVTVSSGGGGSGGGGSGGGGSDIVMTQTPLSLSVTPGEPASISCK

SSQSLVHSNGNTYLHWYLQKPGQSPQLLIYKVSNRFSGVPDRFSGSGSGADFTLKISRVEA

EDVGVYYCAETSHVPWTFGQGTKLEIKEPKSPDKTHTCPPCPAPPVAGPSVFLFPPKPKDT

LMIARTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSVMHEALH

NHYTQKSLSLSPGKIISFFLALTSTALLFLLFFLTLRFSVVKRGRKKLLYIFKQPFMRPVQTTQ

EEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKHDGLYQGLSTATKD

TYDALHMQALPPR

C11D53-1

(SEQ ID NO. 1 + SEQ ID NO. 31)
MALPVTALLLPLALLLHAARPQIQLVQSGPELKKPGETVKISCKASGYTFTDYSINWVKRAPG

KGLKWMGWINTETREPAYAYDFRGRFAFSLETSASTAYLQINNLKYEDTATYFCALDYSYA

MDYWGQGTSVTVSSGGGGSGGGGSGGGGSDIVLTGSPPSLAMSLGKRATISCRASESVTI

LGSHLIHWYQQKPGQPPTLLIQLASNVQTGVPARFSGSGSRTDFTLTIDPVEEDDVAVYYCL

QSRTIPRTFGGGTKLEIKGLAVSTISSFFPPGYQIYIWAPLAGTCGVLLLSLVITLYCKRGRKK

LLYIFKQPFMRPVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSEIGMKGERRRG

KGHDGLYQGLSTATKDTYDALHMQALPPR

-continued

C11D53-2
(SEQ ID NO. 1 + SEQ ID NO. 32)
MALPVTALLLPLALLLHAARP QIQLVQSGPELKKPGETVKISCKASGYTFTDYSINWVKRAPG
KGLKWMGWINTETREPAYAYDFRGRFAFSLETSASTAYLQINNLKYEDTATYFCALDYSYA
MDYWGQGTSVTVSS GGGGSGGGGSGGGGS DIVLTGSPPSLAMSLGKRATISCRASESVTI
LGSHLIHWYQQKPGQPPTLLIQLASNVQTGVPARFSGSGSRTDFTLTIDPVEEDDVAVYYCL
QSRTIPRTFGGGTKLEIK GLAVSTISSFFPPGYQIISFFLALTSTALLFLLFFLTLRFSVVKRGR
KKLLYIFKQPFMRPVQTTQEEDGCSCRFPEEEEGGCELRVKFSRSADAPAYQQGQNQLYN
ELNLGRREEYDVLDKRRGRDPEMGGKPRRKNPQEGLYNELQKDKMAEAYSEIGMKGERR
RGKGHDGLYQGLSTATKDTYDALHMQALPPR

C11D53-3
(SEQ ID NO. 1 + SEQ ID NO. 33)
MALPVTALLLPLALLLHAARP QIQLVQSGPELKKPGETVKISCKASGYTFTDYSINWVKRAPG
KGLKWMGWINTETREPAYAYDFRGRFAFSLETSASTAYLQINNLKYEDTATYFCALDYSYA
MDYWGQGTSVTVSS GGGGSGGGGSGGGGS DIVLTGSPPSLAMSLGKRATISCRASESVTI
LGSHLIHWYQQKPGQPPTLLIQLASNVQTGVPARFSGSGSRTDFTLTIDPVEEDDVAVYYCL
QSRTIPRTFGGGTKLEIK TTTPAPRPPTPAPTIASQPLSLRPEACRPAAGGAVHTRGLDFAC
DIYIWAPLAGTCGVLLLSLVITLYCKRGRKKLLYIFKQPFMRPVQTTQEEDGCSCRFPEEEEG
GCELRVKFSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHMQALPPR

C11D53-4
(SEQ ID NO. 1 + SEQ ID NO. 34)
MALPVTALLLPLALLLHAARP QIQLVQSGPELKKPGETVKISCKASGYTFTDYSINWVKRAPG
KGLKWMGWINTETREPAYAYDFRGRFAFSLETSASTAYLQINNLKYEDTATYFCALDYSYA
MDYWGQGTSVTVSS GGGGSGGGGSGGGGS DIVLTGSPPSLAMSLGKRATISCRASESVTI
LGSHLIHWYQQKPGQPPTLLIQLASNVQTGVPARFSGSGSRTDFTLTIDPVEEDDVAVYYCL
QSRTIPRTFGGGTKLEIK TTTPAPRPPTPAPTIASQPLSLRPEACRPAAGGAVHTRGLDFAC
DIISFFLALTSTALLFLLFFLTLRFSVVKRGRKKLLYIFKQPFMRPVQTTQEEDGCSCRFPEEE
EGGCELRVKFSRSADAPAYQQGQNQLYNELNLGRREEYDVLDKRRGRDPEMGGKPRRKN
PQEGLYNELQKDKMAEAYSEIGMKGERRRGKGHDGLYQGLSTATKDTYDALHMQALPPR

C11D53-5
(SEQ ID NO. 1 + SEQ ID NO. 35)
MALPVTALLLPLALLLHAARP QIQLVQSGPELKKPGETVKISCKASGYTFTDYSINWVKRAPG
KGLKWMGWINTETREPAYAYDFRGRFAFSLETSASTAYLQINNLKYEDTATYFCALDYSYA
MDYWGQGTSVTVSS GGGGSGGGGSGGGGS DIVLTGSPPSLAMSLGKRATISCRASESVTI
LGSHLIHWYQQKPGQPPTLLIQLASNVQTGVPARFSGSGSRTDFTLTIDPVEEDDVAVYYCL
QSRTIPRTFGGGTKLEIK EPKSPDKTHTCPPCPAPPVAGPSVFLFPPKPKDTLMIARTPEVTC
VVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLS
LSPGKIYIWAPLAGTCGVLLLSLVITLYCKRGRKKLLYIFKQPFMRPVQTTQEEDGCSCRFPE

```
EEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPP

R

C11D53-6
                                         (SEQ ID NO. 1 + SEQ ID NO. 36)
MALPVTALLLPLALLLHAARP QIQLVQSGPELKKPGETVKISCKASGYTFTDYSINWVKRAPG

KGLKWMGWINTETREPAYAYDFRGRFAFSLETSASTAYLQINNLKYEDTATYFCALDYSYA

MDYWGQGTSVTVSS GGGGSGGGGSGGGGS DIVLTGSPPSLAMSLGKRATISCRASESVTI

LGSHLIHWYQQKPGQPPTLLIQLASNVQTGVPARFSGSGSRTDFTLTIDPVEEDDVAVYYCL

QSRTIPRTFGGGTKLEIK EPKSPDKTHTCPPCPAPPVAGPSVFLFPPKPKDTLMIARTPEVTC

VVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKSLS

LSPGKIISFFLALTSTALLFLLFFLTLRFSVVKRGRKKLLYIFKQPFMRPVQTTQEEDGCSCRF

PEEEEGGCELRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHMQA

LPPR

C13F12-1
                                         (SEQ ID NO. 1 + SEQ ID NO. 37)
MALPVTALLLPLALLLHAARP QIQLVQSGPELKKPGETVKISCKASGYTFTHYSMNWVKQAP

GKGLKWMGRINTETGEPLYADDFKGRFAFSLETSASTAYLVINNLKNEDTATFFCSNDYLYS

CDYWGRGTTLTVSS GGGGSGGGGSGGGGS DIVLTQSPPSLAMSLGKRATISCRASESVTI

LGSHLIYWYQQKPGQPPTLLIQLASNVQTGVPARFSGSGSRTDFTLTIDPVEEDDVAVYYCL

QSRTIPRTFGGGTKLEIK GLAVSTISSFFPPGYQIYIWAPLAGTCGVLLLSLVITLYCKRGRKK

LLYIFKQPFMRPVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSEIGMKGERRRG

KGHDGLYQGLSTATKDTYDALHMQALPPR

C13F12-2
                                         (SEQ ID NO. 1 + SEQ ID NO. 38)
MALPVTALLLPLALLLHAARP QIQLVQSGPELKKPGETVKISCKASGYTFTHYSMNWVKQAP

GKGLKWMGRINTETGEPLYADDFKGRFAFSLETSASTAYLVINNLKNEDTATFFCSNDYLYS

CDYWGRGTTLTVSS GGGGSGGGGSGGGGS DIVLTQSPPSLAMSLGKRATISCRASESVTI

LGSHLIYWYQQKPGQPPTLLIQLASNVQTGVPARFSGSGSRTDFTLTIDPVEEDDVAVYYCL

QSRTIPRTFGGGTKLEIK GLAVSTISSFFPPGYQIISFFLALTSTALLFLLFFLTLRFSVVKRGR

KKLLYIFKQPFMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYSEIGMKGERR

RGKGHDGLYQGLSTATKDTYDALHMQALPPR

C13F12-3
                                         (SEQ ID NO. 1 + SEQ ID NO. 39)
MALPVTALLLPLALLLHAARP QIQLVQSGPELKKPGETVKISCKASGYTFTHYSMNWVKQAP

GKGLKWMGRINTETGEPLYADDFKGRFAFSLETSASTAYLVINNLKNEDTATFFCSNDYLYS
```

-continued

CDYWGRGTTLTVSSGGGGSGGGGSGGGGSDIVLTQSPPSLAMSLGKRATISCRASESVTI

LGSHLIYWYQQKPGQPPTLLIQLASNVQTGVPARFSGSGSRTDFTLTIDPVEEDDVAVYYCL

QSRTIPRTFGGGTKLEIKTTTPAPRPPTPAPTIASQPLSLRPEACRPAAGGAVHTRGLDFAC

DIYIWAPLAGTCGVLLLSLVITLYCKRGRKKLLYIFKQPFMRPVQTTQEEDGCSCRFPEEEEG

GCELRVKFSRSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALPPR

C13F12-4

(SEQ ID NO. 1 + SEQ ID NO. 40)

MALPVTALLLPLALLLHAARPQIQLVQSGPELKKPGETVKISCKASGYTFTHYSMNWVKQAP

GKGLKWMGRINTETGEPLYADDFKGRFAFSLETSASTAYLVINNLKNEDTATFFCSNDYLYS

CDYWGRGTTLTVSSGGGGSGGGGSGGGGSDIVLTQSPPSLAMSLGKRATISCRASESVTI

LGSHLIYWYQQKPGQPPTLLIQLASNVQTGVPARFSGSGSRTDFTLTIDPVEEDDVAVYYCL

QSRTIPRTFGGGTKLEIKTTTPAPRPPTPAPTIASQPLSLRPEACRPAAGGAVHTRGLDFAC

DIISFFLALTSTALLFLLFFLTLRFSVVKRGRKKLLYIFKQPFMRPVQTTQEEDGCSCRFPEEE

EGGCELRVKFSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDALHMQALPPR

C13F12-5

(SEQ ID NO. 1 + SEQ ID NO. 41)

MALPVTALLLPLALLLHAARPQIQLVQSGPELKKPGETVKISCKASGYTFTHYSMNWVKQAP

GKGLKWMGRINTETGEPLYADDFKGRFAFSLETSASTAYLVINNLKNEDTATFFCSNDYLYS

CDYWGRGTTLTVSSGGGGSGGGGSGGGGSDIVLTQSPPSLAMSLGKRATISCRASESVTI

LGSHLIYWYQQKPGQPPTLLIQLASNVQTGVPARFSGSGSRTDFTLTIDPVEEDDVAVYYCL

QSRTIPRTFGGGTKLEIKEPKSPDKTHTCPPCPAPPVAGPSVFLFPPKPKDTLMIARTPEVTC

VVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKSLS

LSPGKIYIWAPLAGTCGVLLLSLVITLYCKRGRKKLLYIFKQPFMRPVQTTQEEDGCSCRFPE

EEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPP

R

C13F12-6

(SEQ ID NO. 1 + SEQ ID NO. 42)

MALPVTALLLPLALLLHAARPQIQLVQSGPELKKPGETVKISCKASGYTFTHYSMNWVKQAP

GKGLKWMGRINTETGEPLYADDFKGRFAFSLETSASTAYLVINNLKNEDTATFFCSNDYLYS

CDYWGRGTTLTVSSGGGGSGGGGSGGGGSDIVLTQSPPSLAMSLGKRATISCRASESVTI

LGSHLIYWYQQKPGQPPTLLIQLASNVQTGVPARFSGSGSRTDFTLTIDPVEEDDVAVYYCL

QSRTIPRTFGGGTKLEIKEPKSPDKTHTCPPCPAPPVAGPSVFLFPPKPKDTLMIARTPEVTC

VVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKSLS

LSPGKIISFFLALTSTALLFLLFFLTLRFSVVKRGRKKLLYIFKQPFMRPVQTTQEEDGCSCRF

```
PEEEEGGCELRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHMQA

LPPR
```

The following objects, subject matter and embodiments are provided in the present invention:

A BCMA (CD269) specific chimeric antigen receptor (CAR) having one of the polypeptide structure selected from V1 to V6 as illustrated in FIG. 2, said structure comprising an extra cellular ligand binding-domain comprising VH and VL from a monoclonal anti-BCMA antibody, a hinge, a transmembrane domain and a cytoplasmic domain including a CD3 zeta signaling domain and a co-stimulatory domain from 4-1BB.

A BCMA specific CAR as above, wherein said structure V1 comprises a Fc☐RIIIα hinge and CD8α transmembrane domain.

A BCMA specific CAR as above, wherein said structure V2 comprises a Fc☐RIIIα hinge and a 4-1BB transmembrane domain.

A BCMA specific CAR as above wherein said structure V3 comprises a CD8α hinge and a CD8α transmembrane domain.

A BCMA specific CAR as above, wherein said structure V4 comprises a CD8α hinge and a 4-1BB transmembrane domain.

A BCMA specific CAR as above, wherein said structure V6 comprises a IgG1 hinge and a CD8α transmembrane domain.

A BCMA specific CAR as above wherein said structure V6 comprises a IgG1 hinge and a 4-1BB transmembrane domain.

A BCMA specific CAR as above wherein said VH and VL have at least 80% identity with a polypeptide sequence selected from SEQ ID NO. 11 to 18.

A BCMA specific CAR according to any the embodiments above, wherein co-stimulatory domain from 4-1BB has at least 80% identity with SEQ ID NO.8.

A BCMA specific CAR according to any of the embodiments above, wherein said CD3 zeta signaling domain has at least 80% identity with SEQ ID NO. 9.

A BCMA specific CAR as above, wherein said Fc☐RIIIα hinge has at least 80% identity with SEQ ID NO.3.

A BCMA specific CAR according to any of the embodiments above wherein said CD8α hinge has at least 80% identity with SEQ ID NO.4.

A BCMA specific CAR according to the above wherein said IgG1 hinge has at least 80% identity with SEQ ID NO.5.

A BCMA specific CAR as above, wherein said CD8α transmembrane domain has at least 80% identity with SEQ ID NO.6.

A BCMA specific CAR as above, wherein said 4-1BB transmembrane domain has at least 80% identity with SEQ ID NO.7.

A BCMA specific CAR as above further comprising another extracellular ligand binding domain which is not specific for BCMA.

A BCMA specific CAR of structure V1 as above, which comprises a polypeptide sequence having at least 80% identity with SEQ ID NO. 19, SEQ ID NO.25, SEQ ID NO.31 and SEQ ID NO.37.

A BCMA specific CAR of structure V2 as above, which comprises a polypeptide sequence having at least 80% identity with SEQ ID NO. 20, SEQ ID NO.26, SEQ ID NO.32 and SEQ ID NO.38.

A BCMA specific CAR of structure V3 as above, which comprises a polypeptide sequence having at least 80% identity with SEQ ID NO. 21, SEQ ID NO.27, SEQ ID NO.33 and SEQ ID NO.39.

A BCMA specific CAR of structure V4 as above, which comprises a polypeptide sequence having at least 80% identity with SEQ ID NO. 22, SEQ ID NO.28, SEQ ID NO.34 and SEQ ID NO.40.

A BCMA specific CAR of structure V5 as above, which comprises a polypeptide sequence having at least 80% identity with SEQ ID NO. 23, SEQ ID NO.29, SEQ ID NO.35 and SEQ ID NO.41.

A BCMA specific CAR of structure V6 as above, which comprises a polypeptide sequence having at least 80% identity with SEQ ID NO. 24, SEQ ID NO.30, SEQ ID NO.36 and SEQ ID NO.42.

A BCMA specific CAR as above, further comprising a signal peptide.

A BCMA specific CAR as above, wherein said signal peptide has at least 80% sequence identity with SEQ ID NO.1 or SEQ ID NO.2.

A polynucleotide encoding a chimeric antigen receptor according to any of the above embodiment.

An expression vector comprising a nucleic acid as above.

An engineered immune cell expressing at the cell surface membrane a BCMA specific chimeric antigen receptor as above.

An engineered immune cell as above, derived from inflammatory T lymphocytes, cytotoxic T-lymphocytes, regulatory T-lymphocytes or helper T lymphocytes.

An engineered immune cell as above, wherein it is derived from a NK cell.

An engineered cell as above for use in therapy.

An engineered cell as above for use in human therapy.

An engineered cell for use in therapy as above wherein the condition is a pre-malignant or malignant cancer condition characterized by BCMA-expressing cells.

An engineered cell according as above for use in therapy, wherein the condition is a condition which is characterized by an overabundance of BCMA-expressing cells.

An engineered cell according to any one the above for use in therapy, wherein the condition is a haematological cancer condition.

An engineered cell according to any one of the above for use in therapy, wherein the haematological cancer condition is leukemia.

36. An engineered cell according to the above embodiments for use in therapy, wherein the haematological cancer condition is multiple myeloma (MM).

An engineered cell according to any one of the above for use in therapy, wherein said hematologic cancer is a malignant lymphoproliferative disorder.

An engineered cell according to any one the above for use in therapy, wherein said leukemia is selected from the group consisting of acute myelogenous leukemia, chronic myelogenous leukemia and myelodysplastic syndrome.

An engineered cell according to any one of the above, wherein expression of TCR is suppressed in said immune cell.

An engineered cell according to any one the above, wherein expression of at least one MHC protein, preferably γ2 m or HLA, is suppressed in said immune cell.

An engineered cell according to any one the above, wherein said cell is mutated to confer resistance to at least one immune suppressive or chemotherapy drug.

A method of impairing a hematologic cancer cell comprising contacting said cell with an engineered cell according to any one of the above in an amount effective to cause impairment of said cancer cell.

A method of engineering an immune cell comprising:
(a) Providing an immune cell,
(b) Expressing at the surface of said cell at least one BCMA specific chimeric antigen receptor according to any one of the above.

The method of engineering an immune cell as above comprising:
(a) Providing an immune cell,
(b) Introducing into said cell at least one polynucleotide encoding said BCMA specific chimeric antigen receptor,
(c) Expressing said polynucleotide into said cell.

The method of engineering an immune cell as above comprising:
(a) Providing an immune cell,
(b) Introducing into said cell at least one polynucleotide encoding said BCMA specific chimeric antigen receptor,
(c) Introducing at least one other chimeric antigen receptor which is not specific for BCMA.

A method of treating a subject in need thereof comprising:
(a) Providing an immune cell expressing at the surface a BCMA specific Chimeric Antigen Receptor according to any one of the above;
(b) Administrating said immune cells to said patient.

A method according to the above wherein said immune cell is provided from a donor.

A method according to the above wherein said immune cell is provided from the patient himself.

REFERENCES

Arimondo, P. B., C. J. Thomas, et al. (2006). "Exploring the cellular activity of camptothecin-triple-helix-forming oligonucleotide conjugates." *Mol Cell Biol* 26(1): 324-33.

Atkins, J. F., N. M. Wills, et al. (2007). "A case for "StopGo": reprogramming translation to augment codon meaning of GGN by promoting unconventional termination (Stop) after addition of glycine and then allowing continued translation (Go)." *Rna* 13(6): 803-10.

Bierer, B. E., G. Hollander, et al. (1993). "Cyclosporin A and FK506: molecular mechanisms of immunosuppression and probes for transplantation biology." *Curr Opin Immunol* 5(5): 763-73.

Boch, J., H. Scholze, et al. (2009). "Breaking the code of DNA binding specificity of TAL-type III effectors." *Science* 326(5959): 1509-12.

Choulika, A., A. Perrin, et al. (1995). "Induction of homologous recombination in mammalian chromosomes by using the I-SceI system of *Saccharomyces cerevisiae*." *Mol Cell Biol* 15(4): 1968-73.

Christian, M., T. Cermak, et al. (2010). "Targeting DNA double-strand breaks with TAL effector nucleases." *Genetics* 186(2): 757-61.

Cong, L., F. A. Ran, et al. (2013). "Multiplex genome engineering using CRISPR/Cas systems." *Science* 339 (6121): 819-23.

Cros, E. et al. (2004). "Problems related to resistance to cytarabine in acute myeloid leukemia". *Leukemia & Lymphoma.* 45(6):1123-1132.

Deltcheva, E., K. Chylinski, et al. (2011). "CRISPR RNA maturation by trans-encoded small RNA and host factor RNase III." *Nature* 471(7340): 602-7.

Donnelly, M. and G. Elliott (2001). "Nuclear localization and shuttling of herpes simplex virus tegument protein VP13/14." *J Virol* 75(6): 2566-74.

Doronina, V. A., C. Wu, et al. (2008). "Site-specific release of nascent chains from ribosomes at a sense codon." *Mol Cell Biol* 28(13): 4227-39.

Eisenschmidt, K., T. Lanio, et al. (2005). "Developing a programmed restriction endonuclease for highly specific DNA cleavage." *Nucleic Acids Res* 33(22): 7039-47.

Gardin, C. et al. (2007). "Postremission treatment of elderly patients with acute myeloid leukemia in first complete remission after intensive induction chemotherapy: results of the multicenter randomized Acute Leukemia French Association (ALFA) 9803 trial". *Blood.* 109(12):5129-5135.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Henderson, D. J., I. Naya, et al. (1991). "Comparison of the effects of FK-506, cyclosporin A and rapamycin on IL-2 production." *Immunology* 73(3): 316-21.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

June, C. H. et al. (2011). "T Cells with Chimeric Antigen Receptors Have Potent Antitumor Effects and Can Establish Memory in Patients with Advanced Leukemia". *Sci. Transl. Med.* 3(95):ra73.

Kalish, J. M. and P. M. Glazer (2005). "Targeted genome modification via triple helix formation." *Ann N Y Acad Sci* 1058: 151-61.

Li, T., S. Huang, et al. (2011). "TAL nucleases (TALNs): hybrid proteins composed of TAL effectors and FokI DNA-cleavage domain." *Nucleic Acids Res* 39(1): 359-72.

Liu, J., M. W. Albers, et al. (1992). "Inhibition of T cell signaling by immunophilin-ligand complexes correlates with loss of calcineurin phosphatase activity." *Biochemistry* 31(16): 3896-901.

Lonial S, Mitsiades C. S., Richardson P. G., (2011) "Treatment options for relapsed and refractory multiple myeloma". *Clin Cancer Res.* 17:1264-77.

Mali, P., L. Yang, et al. (2013). "RNA-guided human genome engineering via Cas9." *Science* 339(6121): 823-6.

Moscou, M. J. and A. J. Bogdanove (2009). "A simple cipher governs DNA recognition by TAL effectors." *Science* 326(5959): 1501.

Novak A. J., Darce J. R., Arendt B. K., Harder B., Henderson K., Kindsvogel W., et al. (2004) "Expression of BCMA, TAC, and BAFF-R in multiple myeloma: a mechanism for growth and survival". *Blood.* 103:689-94

Paques, F. and P. Duchateau (2007). "Meganucleases and DNA double-strand break-induced recombination: perspectives for gene therapy." *Curr Gene Ther* 7(1): 49-66.

Park, T. S., S. A. Rosenberg, et al. (2011). "Treating cancer with genetically engineered T cells." *Trends Biotechnol* 29(11): 550-7.

Peipp, M., D. Saul, et al. (2004). "Efficient eukaryotic expression of fluorescent scFv fusion proteins directed against CD antigens for FACS applications." *J Immunol Methods* 285(2): 265-80.

Perrin, A., M. Buckle, et al. (1993). "Asymmetrical recognition and activity of the I-ScеI endonuclease on its site and on intron-exon junctions." *Embo J* 12(7): 2939-47.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Rouet, P., F. Smih, et al. (1994). "Introduction of double-strand breaks into the genome of mouse cells by expression of a rare-cutting endonuclease." *Mol Cell Biol* 14(12): 8096-106.

Sorek, R., C. M. Lawrence, et al. (2013). "CRISPR-mediated Adaptive Immune Systems in Bacteria and Archaea." *Annu Rev Biochem.*

Stoddard, B. L. (2005). "Homing endonuclease structure and function." *Q Rev Biophys* 38(1): 49-95.

Van De Donk, N. W. C. J., Kamps S., Mutis, T., Lokhorst, H. M. (2012) "Monoclonal antibody-based therapy as a new treatment strategy in multiple myeloma". *Leukemia.* 26:199-213.

The invention claimed is:

1. A method for treating a pathological condition related to a B-cell maturation antigen (BCMA)-expressing cancer cell in a patient in need thereof, the method comprising:
administering to the patient a therapeutically effective amount of a composition comprising an engineered T cell comprising a cell surface-expressed BCMA specific Chimeric Antigen Receptor (CAR), wherein the BCMA specific CAR comprises:
(a) an extracellular ligand binding-domain comprising a VH and a VL from a monoclonal anti-BCMA antibody, wherein said VH comprises SEQ ID NO. 68 and said VL comprises SEQ ID NO. 69; said VH comprises SEQ ID NO. 11 and said VL comprises SEQ ID NO. 12; or said VH comprises SEQ ID NO. 13 and said VL comprises SEQ ID NO. 14;
(b) a FcγRIIIα hinge, a CD8α hinge or an IgG1 hinge comprising a sequence having at least 90% sequence identity with SEQ ID NOs. 3, 4, and 5, respectively;
(c) a CD8α transmembrane domain; and
(d) an intracellular cytoplasmic domain comprising a CD3 zeta signaling domain and a co-stimulatory domain from 4-1BB;
wherein said BCMA specific CAR-expressing T cell treats the pathological condition related to the BCMA-expressing cancer cell by inducing cytolytic activity in the cancer cell in the patient.

2. The method according to claim 1, wherein the BCMA-expressing cancer cell expresses elevated levels of BCMA.

3. The method according to claim 1, wherein the BCMA-expressing cancer cell is a haematological cancer cell.

4. The method according to claim 1, wherein the CAR comprises a polypeptide sequence comprising at least 90% amino acid sequence identity to SEQ ID NO. 20 or SEQ ID NO. 26.

5. The method according to claim 1, wherein the CAR comprises a polypeptide sequence comprising at least 90% amino acid sequence identity to SEQ ID NO. 19 or SEQ ID NO. 25.

6. The method according to claim 1, wherein the monoclonal anti-BCMA antibody is a humanized antibody.

7. The method according to claim 1, wherein the CAR comprises a polypeptide sequence comprising at least 90% amino acid sequence identity to SEQ ID No. 21 or SEQ ID NO. 27.

8. The method according to claim 1, wherein the CAR comprises a polypeptide sequence comprising at least 90% amino acid sequence identity to SEQ ID NO. 23 or SEQ ID NO. 29.

9. The method according to claim 1, wherein the extracellular domain further comprises an extracellular ligand binding domain that does not bind BCMA.

10. The method according to claim 1, wherein the engineered T cell comprises at least one of the following:
at least one genetic modification to suppress at least one MHC protein;
at least one genetic modification to confer resistance to at least one immune suppressive drug or at least one chemotherapy drug;
at least one genetic modification to inactivate a T-Cell receptor (TCR) by knocking out a TCR subunit; or
any combination thereof.

11. The method according to claim 1, wherein the CD3 zeta signaling domain comprises the polypeptide of SEQ ID NO. 9 or an amino acid sequence having at least 90% sequence identity to SEQ ID NO. 9.

12. The method according to claim 1, wherein the co-stimulatory domain from 4-1BB comprises the polypeptide of SEQ ID NO. 8 or an amino acid sequence having at least 90% sequence identity to SEQ ID NO. 8.

13. The method according to claim 1, wherein said CD8α transmembrane domain comprises the polypeptide of SEQ ID NO. 6 or an amino acid sequence having at least 90% sequence identity to SEQ ID NO. 6.

14. The method according to claim 1, wherein the BCMA specific CAR further comprises a signal peptide comprising SEQ ID NOs. 1 or 2.

15. The method according to claim 10, wherein the at least one genetic modification to suppress at least one MHC protein comprises suppression of an MHC associated β2m.

16. The method according to claim 1, wherein the engineered T cell further comprises a suicide gene.

17. The method according to claim 1, wherein the BCMA specific CAR is encoded by a lentivirus vector construct or an adeno-associated virus vector construct.

18. The method according to claim 10, wherein the engineered T cell comprises a genetic modification to inactivate the alpha beta T-Cell receptor (TCR) by knocking out a TCR alpha subunit.

19. The method according to claim 10, wherein the engineered T cell comprises a genetic modification to inactivate a CD52 gene.

20. A method of treating a pathological condition related to a B-cell maturation antigen (BCMA)-expressing cancer cell in a patient in need thereof, the method comprising:
administering to said patient a composition comprising an engineered T cell expressing a BCMA specific Chimeric Antigen Receptor (CAR) at the cell surface, said CAR comprising:
(a) an extracellular ligand binding-domain comprising VH and VL from a monoclonal anti-BCMA antibody, wherein the VH comprises at least one CDR sequence selected from the group consisting of SEQ ID NOs. 61, 62, and 63 and wherein the VL comprises at least one CDR sequence selected from the group consisting of SEQ ID NOs. 64, 65, 66, and 67;
(b) a FcγRIIIα hinge, a CD8α hinge or an IgG1 hinge comprising a sequence having at least 90% sequence identity with SEQ ID NOs. 3, 4, and 5, respectively;
(c) a CD8α transmembrane domain; and
(d) an intracellular cytoplasmic domain comprising a CD3 zeta signaling domain and a co-stimulatory domain from 4-1BB;
wherein said BCMA specific CAR-expressing T cell treats the pathological condition related to the BCMA-expressing cancer cell by inducing cytolytic activity in the cancer cell in the patient.

* * * * *